US008003101B2

(12) United States Patent
Life et al.

(10) Patent No.: US 8,003,101 B2
(45) Date of Patent: *Aug. 23, 2011

(54) INFLAMMATORY MEDIATOR ANTAGONISTS

(75) Inventors: Paul F. Life, Stevenage (GB); Edward S. Rees, Stevenage (GB); Andrew D. Rhodes, Stevenage (GB)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/746,090

(22) Filed: May 9, 2007

(65) Prior Publication Data

US 2008/0044409 A1 Feb. 21, 2008

Related U.S. Application Data

(63) Continuation of application No. 11/260,844, filed on Oct. 27, 2005, now Pat. No. 7,291,332, which is a continuation of application No. 10/442,289, filed on May 21, 2003, now abandoned, which is a continuation of application No. 09/276,147, filed on Mar. 25, 1999, now Pat. No. 6,706,266.

(30) Foreign Application Priority Data

Mar. 26, 1998 (GB) .................................. 9806530.3

(51) Int. Cl.
*A61K 39/395* (2006.01)
*A61K 39/00* (2006.01)
*A61K 39/38* (2006.01)
(52) U.S. Cl. ................ 424/139.1; 424/184.1; 424/278.1
(58) Field of Classification Search .................. None
See application file for complete search history.

(56) References Cited

U.S. PATENT DOCUMENTS

| 5,426,048 | A | 6/1995 | Gearing |
| 5,451,411 | A | 9/1995 | Gombotz et al. |
| 5,559,012 | A | 9/1996 | Brailly et al. |
| 5,571,513 | A | 11/1996 | Burstein |
| 5,618,715 | A | 4/1997 | Shoyab et al. |
| 6,706,266 | B1 | 3/2004 | Life |

FOREIGN PATENT DOCUMENTS

| EP | 0 290 948 | 11/1988 |
| EP | 0 451 612 | 10/1991 |
| EP | 0 485 961 | 5/1992 |
| EP | 0 748 870 | 12/1996 |
| EP | 0 450 742 | 5/1997 |
| EP | 0572 118 | 7/1998 |
| WO | WO 90/12585 | 11/1990 |
| WO | WO 91/09057 | 6/1991 |
| WO | WO 93/05169 | 3/1993 |
| WO | WO 94/04190 | 3/1994 |
| WO | WO 94/05318 | 3/1994 |
| WO | WO 95/00852 | 1/1995 |
| WO | WO 95/09005 | 4/1995 |
| WO | WO 95/13393 | 5/1995 |
| WO | WO 95/33059 | 12/1995 |
| WO | WO 96/09382 | 3/1996 |
| WO | WO 97/16202 | 5/1997 |
| WO | WO 98/18483 | 5/1998 |
| WO | WO 99/48523 | 9/1999 |

OTHER PUBLICATIONS

Colman Res. in Immunol. 1994, 145, 33-36.*
Ward et al., Therap. Immunol. 1994, 1, 165-171.*
U.S. Appl. No. 09/646,727, filed Sep. 21, 2000, Life.
Barton et al., "Oncostatin M stimulates HepG2 and B9 cells: Possible role in plasmacytoma development" (1994) *FASEB Journal* 8: Abst 2766.
Bell et al., "Oncostatin M induces leukocyte infiltration and cartilage proteoglycan degradation in vivo in goat joints" *Arthritis and Rheumatism* (1999) 4:2543-1511.
Bonifati et al, "Leukemia inhibitory factor (LIF) and oncostatin M (OSM) hemopoietins, are increased in organ culture supernatant of lesional psoriatic skin" *Australas J Dermatol* (1999) 38:Abst 2437.
Boutten et al., "Oncostatin M is a potent stimulator of $\alpha_1$-antitrypsin secretion in lung epithelial cells: Modulation by transforming growth factor-$\beta$ and interferon-$\gamma$"*Am J. Reps Cell & Mol Biol* (1998)18:511-520.
Brown et al., "Regulation of MHC expression by oncostatin M" *J Cell Biochem* (1994) 18:Abstract O 103.
Cai et al., "Oncostatin-M is an autocrine growth factor in Kaposi's sarcoma" Am J Pathol (1994) 145:74-79.
Cao et al., "Oncostatin M inhibits type 1 plasminogen activator inhibitor synthesis in cultured human endothelium" Thrombosis and Haemostatis (1995) 73: Abst 874.
Carrere et al., "The interleukin-1$\alpha$ and oncostatin M co-operation in cartilage degradation requires two proximal AP-1 sites in the MMP-1 promoter" *14th European League Against Rheumatism Congress*, (1999) Abst 972 Glasgow.
Carroll et al, "Antagonism of the Il-6 cytokine subfamily—a potential strategy for more effective therapy in rheumatoid arthritis" *Inflamm Res* (1999) 47:1-7.
Cawston et al., "The regulation of MMPs and TIMPs in cartilage turnover" Ann NY Acad Sci (1999) 878:120-129.
Cawston et al., "Interleukin-1 and Oncostatin M in combination promote the release of collagen fragments from bovine nasal cartilage in culture" *Biochem Biophys Res Comm* (1999) 215:377-385.
Cawston et al., "The role of oncostatin M in animal and human conective tissue collagen turnover and its localization with the rheumatoid joint" *Arthritis & Rheumatism*(1998) 41:1760-1771.
Cichy et al., "Regulation of the type II oncostatin M receptor expression in lung-derived epithelial cells" *FEBS Lett* (1998) 429:412-416.

(Continued)

Primary Examiner — Michail Belyavskyi
(74) Attorney, Agent, or Firm — Jason C. Fedon; William T. Han

(57) ABSTRACT

The present invention relates to methods of reducing cartilage degradation in a patient comprising administering to a patient in need thereof an effective amount of an antibody antagonist to the mature form of OSM.

9 Claims, 29 Drawing Sheets

OTHER PUBLICATIONS

Figure 1A:
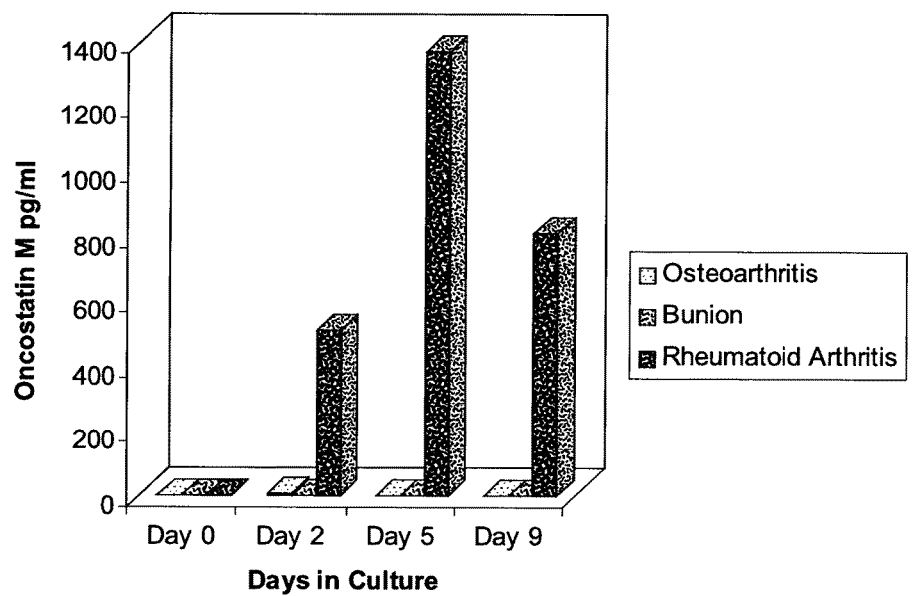

Chauhan et al., "Oncostatin M induces association of GRB2 with janus kinase JAK2 in multiple myeloma cells" *Blood* (1995) 86:Abst 214.

Cleaver et al., "Interleukin-13 blocks the release of collagen fragments from bovine nasal cartilage treated with interleukin-α and oncostatin M" *14th European League Against Rheumatism Congress* (1999) Abst 966.

Duncan et al., "Oncostatin M stimulates collagen and glycosaminoglycan production by cultured normal dermal fibroblasts: Insensitivity of sclerodermal and keloidal fibroblasts" *J Invest Dermatol* (1995)104:128-133.

Ensoli et al., "Inflammatory cytokines and HIV-1-associated neurodegeneration: Oncostatin-M produced by mononuclear cells from HIV-1-infected individuals induces apoptosis of primary neurons" *J Immunol* (1999)162:6268-6277.

Este et al., "Oncostatin M inhibits HIV-TAT mediated transactivation in HeLa-TAT cells" *10th International Conference on AIDS* (1994) Abst PB0283.

Faris et al "The Oncostatin M response in Kaposi's Sarcoma Cells Involves JAKs, Adaptor Proteins, Raf-1 and MEK-1" *FASEB Journal* (1995) 9:Abst 1175.

Friend et al., "Interaction of oncostatin-M with both shared and specific receptors defined by structure/function studies" *Cytokine* (1995) 7:Abst A286.

Gearing et al., "Proliferative responses and binding properties of hematopoietic cells transfected with low-affinity receptors for leukemia inhibitory factor, oncostatin-M, and cillary neurotorphic factor" *Proc Natl Acad Sci USA* (1994) 91:1119-1123.

Geisterfer et al., "Cytokines oncostatin M and interleukin 1 regulate the expression of the IL-6 receptor (gp80, gpl 130)" *Cytokine* (1995) 7:503-509.

Grenier et al., "Oncostatin M production and regulation in human polymorphonuclear neutrophils" *Cytokine* (1997) 9:Abst 129.

Guillen et al., "Oncostatin M down-regulates basal and induced cytochromes P450 in human hepatocytes " *J Pharm Exp Therap* (1998) 285:127-134.

Herbert et al., "Effect of ciprofibrate on fibrinogen synthesis in vitro on hepatoma cells and in vivo in genetically obese Zucker rats"*Blood Coag Fibrinol* (1999) 10:234-244.

Heymann et al., "Human interleukin for DA cells/leukemia inhibitory factor and oncostatin M enhance membrane expression of intercellular adhesion molecule-1 on melanoma cells but not the shedding of its soluble form" *Cytokine* (1995) 7:111-117.

Heymann et al., "Upmodulation of αvβ1 integrin on human tumor cells by leukemia inhibitory factor (LIF) and oncostatin M(OSM)" *Bulletin du Cancer* (1995) 83:13-21.

Heymann et al., "Modulation of the expression of αvβ1 integrin on the surface of human cancer cells by leukaemia inhibitory factor (LIF) and oncostatin M (OSM)" *Bulletin du Cancer* (1995) 83:13-21.

Hui et al., "Transforming growth factor-β1 blocks the release of collagen fragments from bovine nasal cartilage stimulated by interleukin-1α in combination with oncostatin M"*4th European League Against Rheumatism Congress* (1999)Abst 973.

Ichihara et al., "Murine oncostatin M transduces signals only through its specific receptor but not through LIF receptor/GP130 complex" *Exp Hematol* (1995) 23:Abst 364.

Ichihara et al., "Oncostatin M and leukemia inhibitory factor do not use the same functional receptor in mice" *Blood* (1997) 90:165-173.

Komine et al., "Th-1 and Th-2 lymphocytes differently regtulated epidermal keratin gene expression" *J Invest Dermatol* (1995) 104:Abst 190.

Koshy et al., "The interleukin-1a in combination with oncostatin M promoted the breakdown of human articular cartilage" *14th European League Against Rheumatism Congress* (1999) Abst 970.

Lewis et al., "Leukemia inhibitory factor (LIF), ciliary neurotrophic factor (CNTF) and Oncostatin M (OSM) actuate P21 ras in neuroblastoma cell line" *Society for Neuroscience* (1993) 19:Abst 540.3.

Li et al., "Effect of delivery route on pulmonary response to oncostatin M" *Annual Meeting of the American Association of Pharmaceutical Scientsts* (1999) Abst.

Liu et al., "Oncostatin M activates LDL receptor ene transceiption in sterol repressed liver cells" *FASEB Journal* (1994) 8:Abstr. 3148.

Liu et al., "Concostatin M inhibits breast cancer cell growth" *Proc Amer Assoc Cancer Res* (1995) 36:Abst 1529.

Liu et al., "Effect of delivery route on pulmonary response to oncostatin M" *Annual Meeting of the American Association of Pharmaceutical Scientists* (1999) Abst.

Loy et al., "Oncostatin M: Development of a Pleiotropic Cytokine" *Toxicologic Pathology* (1999)27:151-155.

Malik et al., "Molecular cloning, sequence analysis, and functional expression of a novel growth regulator, oncostatin M" *Molecular and Cellular Biology* (1989)9:2847-2853.

Modur et al., "Oncostatin M is a novel endothelial cell proinflammatory agonist" *J Invest Med* (1996)44:Abst 197A.

Modur et al., "Oncostatin M is a proinflammatory mediator, in vivo effects correlate with endothelial cell expression of inflammatory cytokines and adhesion molecules" *J Clin Invest* (1997) 100:158-168.

Moreland et al., "Treatment of rheumatoid arthritis with a recombinant human tumor necrosis factor receptor (p75)-Fc fusion protein" *New England J Medicine* (1997) 337:141-147.

Morgan et al., "Alpha-1-Antitrypsin(AAT) gene regulation by oncostatin-M (OM)" *Am J of Resp. and Critical Care Med* (1999)159:Abst 444.

Mori et al., "Oncostatin M (OM) Promotes the growth of DU 145 human prostate cancer cells, but not PC-3 or LNCaP through the signaling of the OM specific receptor" *Anticancer Res* (1999)19:1011-1016.

Nishimoto et al, "Oncostatin-M, leukemia inhibitory factor, and interleukin-6 induce the proliferation of human plasmacytoma cells via the common signal transducer GP130" *J Exp Med* (1994) 179:1343-1347.

Okamoto et al., "Study on presence of interleukin 6(IL-6), IL-11, leukemia inhibitory factory (LIF) and oncostatin M (OSM) in chronic rheumatoid arthritis (RA) synovial membrance lesion" *Ryumachi* (1994) 34:W13-8.

Okamoto et al, "Evaluation of the expression of interleukin 6(IL-6), IL-11, leukemia inhibitory factory (LIF) and oncostatin M (OSM) in chronic rheumatoid arthritis (RA) synovial membrane lesion" *Ryumachi* (1994) 34:W13-8.

Palmisano et al, "A double-blind, placebo-controlled, single subcutaneous dose escalation trial of oncostatin-M in healthy male subject" *41st Ann Meeting Am Soc Hematol* (1999)Abst 3404.

Powers et al., "Towards the solution structure of oncostatin M, a 23 kDA alpha-helical protein" *J Cell Biochem—Supplement 21 (Part B)*(1995) Abst D2-150.

Richards et al., "Regulation of tissue inhibitor of metalloproteinase-1 in fibroblasts and acute phase proteins in hepatocytes in vitro by mouse oncostatin M, cardiotrophin-1, and IL-6", *J Immunol* (1997) 159:2431-2437.

Richards et al., "Selective regulation of metalloproteinase inhibitor (TIMP-1) by oncostatin M in fibroblasts in culture", *J Immunol* (1993) 150:5596-5603.

Richards et al., "Interaction between oncostatin M, interleukin 1 and prostaglandin E(2) in induction of IL-6 expression in human fibroblasts" *Cytokine* (1994) 6:40-47.

Richards et al., "Oncostatin M inhibits neutrophil influx in LPS-induced acute lung inflammation in Sprague-Dawley rats" *FASEB J* (1994) 9:Abst 2851.

Rose et al., "Oncostatin M (OSM) inhibits the differentiation of pluripotent embryonic stem cells in vitro" *Cytokine* (1994)6:48-54.

Rowan et al, "Interleukin-1 α in combinatino with oncostatin M induces collagenase in chondrocytes: A role for MMP-1 and MMP-13 in cartilage collagen breakdown" *14th European League Against Rheumatism Congress* (1999) Abst 968.

Rowan et al., "Investigation of surface receptors on human chondrocytes stimulated to produce collagenase with a combination of interleukin-1α and oncostatin M" *14th European League against Rheumatism Congress* (1999) Abst 967.

Schaefer et al., "Oncostatin M binds to liver collagens type I, III and VI" *Hepatology* (1998) 28: Abst 1393.

Shingleton et al, "Retinoic acid in combination with interleukin-alpha or oncostatin M promotes release of collagen fragments from bovine cartilage" *14th European League Against Rheumatism Congress* (1999), Abst 969.

Spence et al., "Suppression of c-myc transcription by oncostatin M in breast cancer cells" *Proc Amer Assoc Cancer* (1996) Res 37:Abst 3569.

Spence et al., Suppression of EGF-mediated tyrosine phosphorylation by pretreatment of breast cancer cells with oncostatin M, *Proc Amer Assoc Cancer Res* (1997) 38: Abst 2968.

Sporeno et al., "Oncostatin-M binds directly to gp130 and behaves as interleukin-6 antagonist on a cell line experssing gp130 but lacking functional oncostation-M receptors" *J Biol Chem* (1994)269:10911-10995.

Steogbauer et al., "Oncostatin M (OSM) inhibits proliferation and induces differentiation in human glioma cells" *Society for Neuroscience-Abstracts* (1996)22:Abst 369.4.

Thoma et al., "Characterization of the oncostatin M (OSM)-specific receptor" *J Cell Biochem* (1994) 18:Abst O 219.

Thoma et al., "Oncostatin M and leukemia inhibitory factor trigger overlapping and different signals through partially shared receptor complexes" *J Biol Chem* (1994) 269:6215-6222.

Vasse et al., "Oncostatin M induces angiogenesis in vigtro and in vivo" *Arterioscler Thromb Vasc Biol* (1999) 19:1835-1842.

Wallace et al., "Regulation of inflammatory responses by oncostatin M" *J Immunol* (1999) 162:5547-5555. Note: an erratum appears in May 15, 2000 edition.

Wallace et al., "Thrombocytopoietic properties of oncostatin M" *Blood* (1995) 86:1310-1315.

Webster et al., "Leukemia inhibitory factor and oncostatin M stimulate ACTH secretion and POMC expression in mouse corticotroph tumor cells" *J Endocrinol* (1995) 144:Abst P294.

Xing et al., "IL-6 is an antiinflammatory cytokine required for controlling local or systemic acute inflammatory responses" (1998) *J. Clin Invest* 101:311-320.

Zhang et al., "Ciliary neurotropic factor, interleukin-11, leukemia inhibitory factor, and oncostatin-M are growth factors for human myeloma cell lines using the interleukin-6 signal transducer GP130" *J Exp Med* (1994) 179:1337-1342.

Coleman P., "Effects of amino acid sequence changes on antibody-antigen interactions" *Res. in Immunol* (1994) 145:33-36.

Malik et al., Developmental Abnormalities in Mice Transgenic for bovine Oncostatin M *Mol. Cell Biol.* (1995) 15:2349-2358.

Rhodes et al., The Generation and Characterization of Antagonist RNA Aptamers to Human Oncostatin M *J. Bio Chem.* (2000) 37:28555-28561.

Van Noort et al., Cell Biology of Autimmune Diseases *International Review of Cytology* (1998) 178:127-203.

Vandenabeele et al., "Two tumour necrosis factor receptors structure and function" *Trends in Cell Biology* (1995) 5:392-399.

Ward, et al., "Blocking of Adhesion Molecules in vivo as anti-inflammatory therapy" *Therap. Immunol.* (1994) 1:165-171.

Yoshida et al., "Myocardial, hematological and Placental Disorders Caused by Targeted Disruption of gp130, a Common Signal Transducer for IL-6 Family of Cytokines" *Contemporary Immunology: Cytokine Knockouts, Chapter 16 eds. Durum and Muegge Human Press Inc.*, Totowa, NJ, Chapter 16: 259-285.

Kerr et al., "Adenovirus Vector Expressing Mouse Oncostatin M Induces Acute-Phase Proteins and TIMP-1 Expression In Vivo in Mice," *Journal of Interferon and Cytokine Research* (1999)19:1195-1205.

Walmsley et al., "An Anti-Inflammatory Role for Interleukin-11 in Established Murine Collagen-Induced Arthritis," *Immunology* (1998) 95(1):31-37.

Papanicolaou, et al., "The Pathophysiologic Roles of Interleukin-6 in Human Disease" *Annals of Internal Medicine* (1998)128(2):127-137.

Langdon et al., "Murine Oncostatin M Stimulates Mouse Synoval Fibroblasts In Vitro and Induces Inflammation and Destruction in Mouse Joints In Vivo" *Am Jour of Pathology* (2000)157(4):1187-1196.

Hassen et al., "Overexpression of Mouse Oncostatin M in Joints by Adenovirus Vector Causes Pannus-like Alternations in Synovium of Mice" *Arthritis and Rheumatism* (1998)41(9)Poster 1285:S247.

Okamoto et al., "The Synovial Expression and Serum Levels of Interleukin-6, Interleukin-11, Leukemia Inhibitory Factor, and Oncostatin M in Rheumatoid Arthritis" *Arthritis & Rheumatism* (1997) 40(6):1096-1105.

Hui et al., "Detection of Oncostatin M in Synovial Fluid from Patients with Rheumatoid Arthritis," *Annals of Rheumatic Disease* (1997) 56(3):184-187.

Liautard et al., "Specific Inhibition of IL-6 Signalling with Monoclonal Antibodies Against the gp130 Receptor" *Cytokine* (1997)9(4):233-241.

Gastos et al., "Oncostatin M Differentially Regulates tissue Inhibitors of Metalloproteinases TIMP-1 and TIMP-3 Gene Expression in Human Synovial Lining Cells" *Eur. J Biochem FEBBS* (1996)241:56-63.

Yao et al., "Interleukin 4 or Oncostatin M Induces a Prolonged Increase in P-Selectin mRNA and Protein in Human Endothelial Cells" *Journal of Experimental Medicine*(1996)184(1):81-92.

Richards et al., "Oncostatin M Inhibits IL-1-Induced Expression of IL-8 and Granulocyte-macrophage Colony-Stimulating Factor by Synovial and Lung Fibroblasts," *Journal of Immunology* (1996)156:343-349.

Wallace et al., "In Vivo Properties of Oncostatin M"*Annals NY Academy of Sciences*, V762:42-54.

Emery et al., "The Validity of Surrogate Markers in Rheumatic Disease," *British Society for Rheumatology*(1993)32(Suppl 3):3-8.

Radka et al., "The Binding Pattern of a Neutralizing Monoclonal Antibody to Mutant Oncostatin M Molecules is Correlated with Functional Activity" *Cytokine*(1994)6(1):55-60.

Radka et al., "Abrogation of the Antiproliferative Activity of Oncostatin M by a Monoclonal Antibody" *Cytokine*(1992)4(3):221-226.

Grove et al., "Macrophage-derived factors increase low density lipoprotein uptake and receptor number in cultured human liver cells" *J of Lipid Research* (1991)32(12)1189-97.

Yoshida et al., "Targeted Disruption of gp130, a Common Signal Transducer for the Interleukin 6 Family of Cytokines, Leads to Myocardial and Hematological Disorders" *Proc. Natl. Acad. Sci. USA*(1996)93:407-411.

Hooge, et al., "Growth Plate Damage, a Feature of Juvenile Idiopathic Arthritis, Can Be Induced by Adenoviral Gene Transfer of Oncostatin M" Arthritis & Rheumatism (Jun. 2003) 48:1750-1761.

Rose, T.M. and Bruce, A. G., "Oncostatin M is a member of a cytokine family that includes leukemia-inhibitory factor, granulocyte colony-stimulating factor, and interleukin 6" Proc. Natl. Acad. Sci. (Oct. 1981) 88:8641-8645.

* cited by examiner

Spontaneous OSM release from synovial tissue

FIG. 5a

Rheumatoid Arthritis
CD130 localised to endothelial cells of synovial vessels.

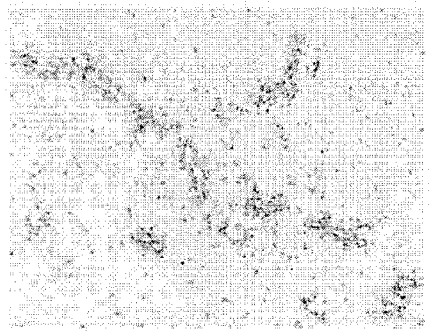

FIG. 5b

Rheumatoid Arthritis
Serial section of Figure 5a showing localisation of CD62P to the endothelial cells of the same vessels.

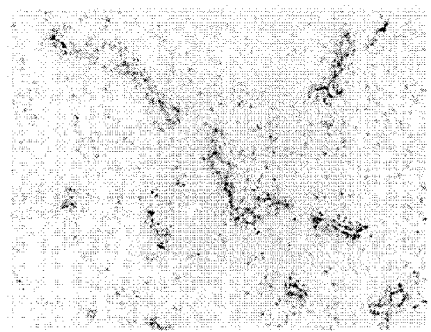

FIG. 5c

Rheumatoid Arthritis
Negative Control (slightly higher power) showed no positivity.

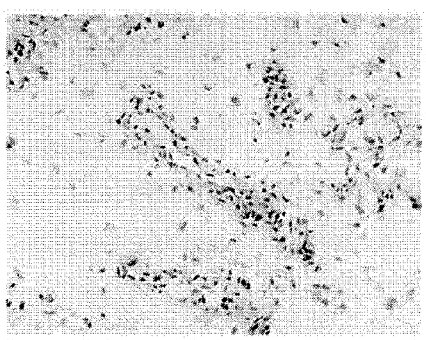

FIG. 5d

Rheumatoid Arthritis
CD62E localised to endothelial cells. Small positive vessels can be seen within the lymphoid aggregate at the top of the picture.

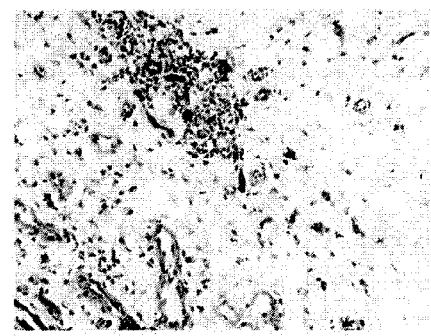

Figure 7A:
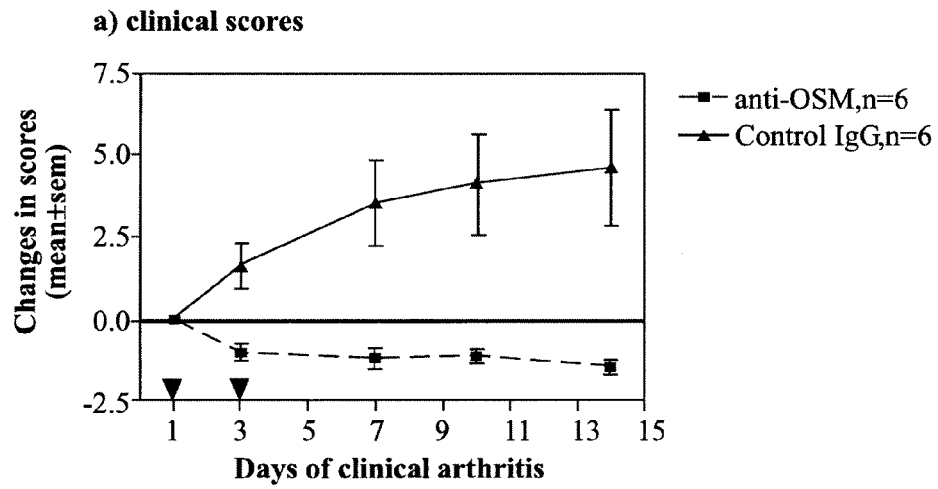
Figure 7B:
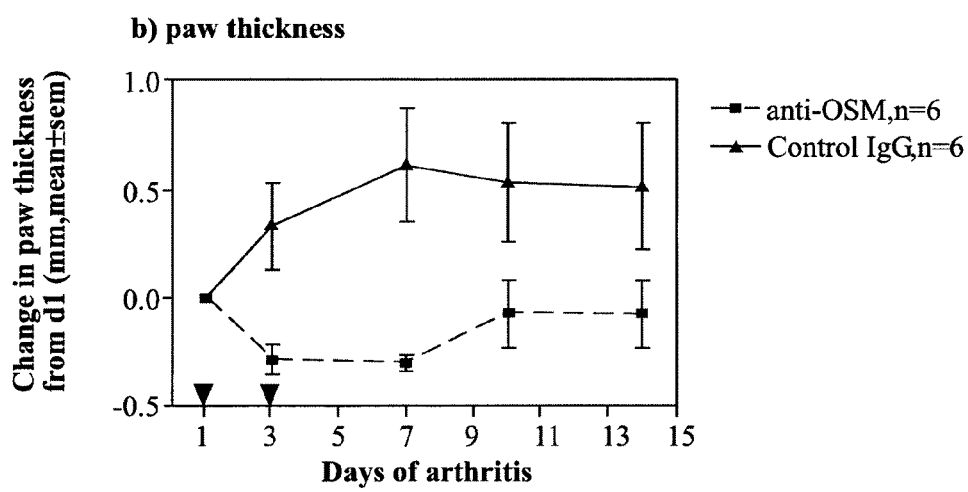

Figure 7. Arthritic DBA/1 mice treated on day 1 and day 3 of clinical symptoms with goat anti-OSM Ab or control goat IgG (100 μg/injection).

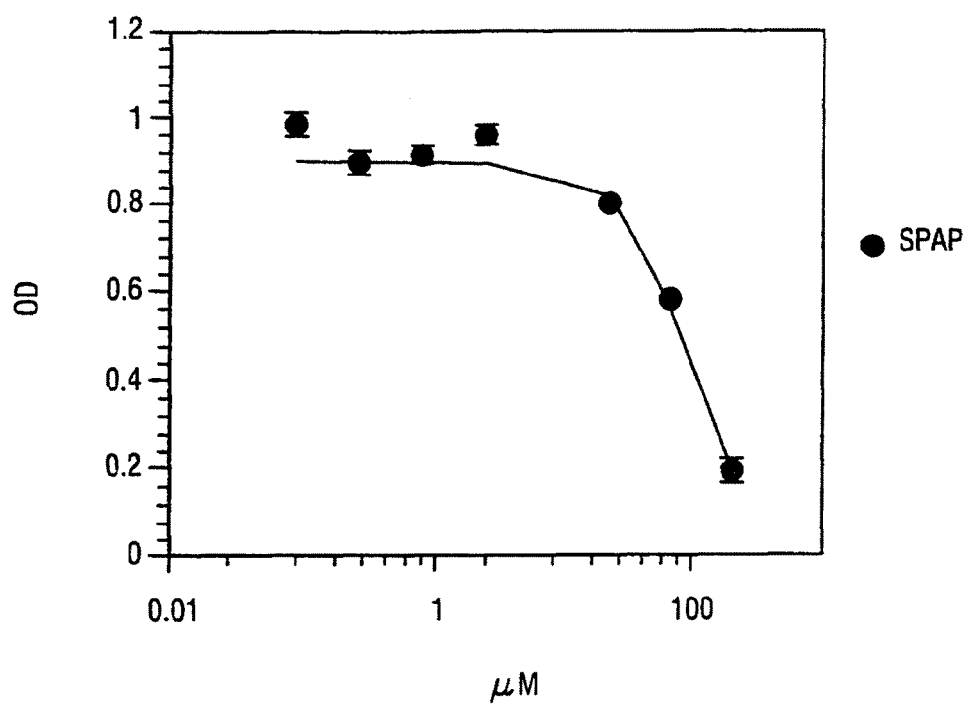
FIG. 10a GW340442X
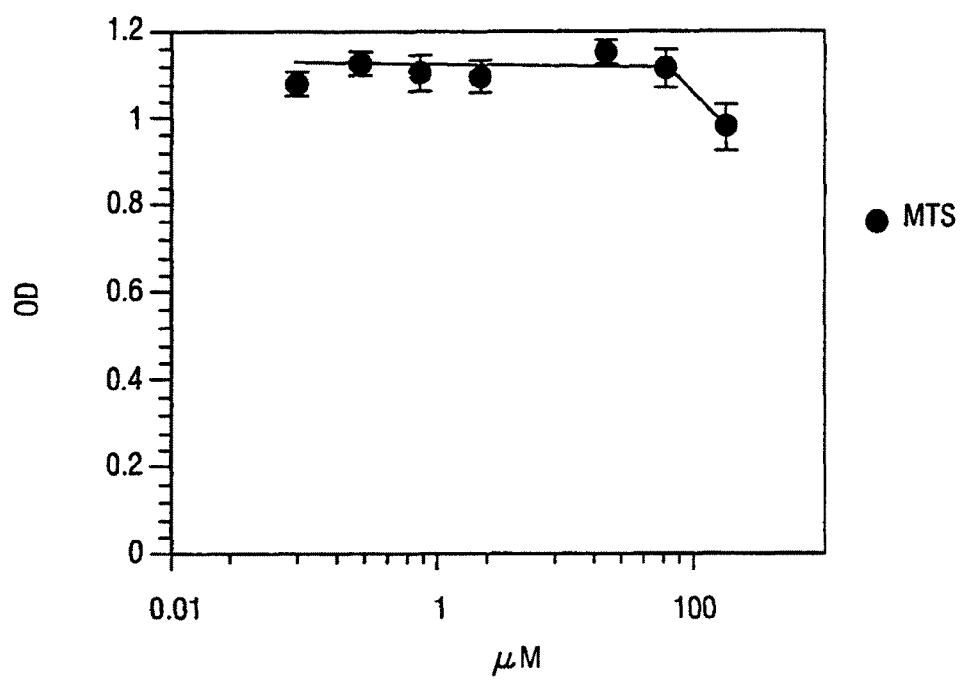
FIG. 10b GW340442X

```
.........A A.TACGACTC ACTATA.GGG AGGACGATGC GGTTATACTA GCTGCGGTTA GCGACAGCCC TCCCTAGCG. .TCA.GACGA CTCGCCCGAG
CCGAAGCTTA A.TACGACTC ACTATA.GGG AGGACGATGC GGTGACGCGA TCCGCCGTTC CCATCCGCAC GCCCTA.CAC CTCA.GACGA CTCGCCCGAG

CCGAAGCTTA A.TACGACTC ACTATA.GGG AGGACGATGC GGAACAAAGC TGGAGTACTT ACCGAACATC CGT.CTRACC CCTCAGACGA CTCGCCCGAG
CCGAAGCTTA A.TACGACTC ACTATA.GGG AGGACGATGC GGAACAAAGC TGGAGTACTT ACCGAACATC CGTCCTGACC CCCCAGACGA CTCGCCCGAG

CCGAAGCTTA A.TACGACTC ACTATA.GGG AGGACGATGC GGATCACCCT GAACCGGCCC AGCAGACTGC TGACGGCACG ATC.AGACGA CTCGCCCGAG
CCGAAGCTTA A.TACGACTC ACTATA.GGG AGGACGATGC GGATCACCCT GAACCGGCCC AGCAGACTGC TGACGGCACG ATC.AGACGA CTCGCCCGAG
CCGAAGCTTA A.TACGACTC ACTATA.GGG AGGACGATGC GGATCGCCCT GAACCGGCCC AGCAGACTGC TGACGGCACG ACC.AGACGA CTCGCCCGAG
CCGAAGCTTA A.TACGACTC ACTATA.GGG AGGACGATGC GGATCGCCCT GAACCGGCCC AGCAGACTGC TGACGGCACG ACC.AGACGA CTCGCCCGAG
CCGAAGCTTA A.TACGACTC ACTATA.GGG AGGACGATGC GGATCGCCCT GAACCGGCCC AGCAGACTGC TGACGGCACG ATC.AGACGA CTCGCCCGAG
CCGAAGCTTA A.TACGACTC ACTATA.GGG AGGACGATGC GGATCGCCCT GAACCGGCCC AGCAGACTGC TGACGGCACG ATC.AGACGA CTCGCCCGAG
CCGAAGCTTA A.TACGACTC ACTATA.GGG AGGACGATGC GGATCGCCCT GAACCGGCCC AGCAGACTGC TGACGGCACG ATC.AGACGA CTCGCCCGAG
CCGAAGCTTA A.TACGACTC ACTATA.GGG AGGACGATGC GGATCGCCCT GAACCGGCCC AGCAGACTGC TGACGGCACG ATC.AGACGA CTCGCCCGAG
CCGAAGCTTA A.TACGACTC ACTATA.GGG AGGACGATGC GGATCGCCCT GAACCGGCCC AGCAGACTGC TGACGGCACG ATC.AGACGA CTCGCCCGAG
CCGAAGCTTA A.TACGACTC ACTATA.GGG AGGACGATGC GGATCGCCCT GAACCGGCCC AGCAGACTGC TGACGGCACG ATC.AGACGA CTCGCCCGAG
CCGAAGCTTA A.TACGACTC ACTATA.GGG AGGACGATGC GGATCGCCCT GAACCGGCCC AGCAGACTGC TGACGGCACG ATC.AGACGA CTCGCCCGAG
CCGAAGCTTA A.TACGACTC ACTATA.GGG AGGACGATGC GGATCGCCCT GAACCGGCCC AGCAGACTGC TGACGGCACG ATC.AGACGA CTCGCCCGAG
CCGAAGCTTA A.TACGACTC ACTATA.GGG AGGACGATGC GGATCGCCCT GAACCGGCCC AGCAGACTGC TGACGGCACG ATC.AGACGA CTCGCCCGAG
CCGAAGCTTA A.TACGACTC ACTATA.GGG AGGACGATGC GGATCGCCCT GAACCGGCCC AG.AGACTGC TGACGGCACG ATC.AGACGA CTCGCCCGAG
CCGAAGCTTA A.TACGACTC ACTATA.GGG AGGACGATGC GGATCGCCCT GAACCGGCCC AGCAGACTGC TGACGGCACG ATC.AGACGA CTCGCCCGAG
CCGAAGCTTA A.TACGACTC ACTATA.GGG AGGACGATGC GGATCGCCCT GAACCGGCCC AGCAGACTGC TGACGGCACG ATC.AGACGA CTCGCCCGAG
CCGAAGCTTA A.TACGACTC ACTATA.GGG AGGACGATGC GGATCGGTCT GAACCGGCCC AGCAGACTGC TGACGGCACG ATC.AGACGA CTCGCCCGAG
CCGAAGCTTA A.TACGACTC ACTATA.GGG AGAACGATGC GGATCGCTCT GAACCGGCCC AGCAGACTGC TGACGGCACG ATC.AGACGA CTCGCCCGAG
CCGAAGNTTA A.TACGACTC ACTATA.GGG AGGACGATGC GGATC...CCT GAACCGGCCC AGCAGACTGC TGACGGCACG ATC.AGACGA CTCGCCCGAG
CCGAAGTTA  ATTAGACTC ACTATA.GGG AGGACGATGC GGATCNTCTT GAACCGGCCC AGCAGACTAC TGACGGCACG ATC.AGACGA CTCGCCCGAG
CCGAAGCTTA A.TACGACTC ACTATA.GGG ATACGAACTC GGATCNTCTT NNNNHTTCC NNCACACTGA ATACNTCCNG ATCAAGACGA CTCGCCCGAG
CGAAGCTTA A.TACGACTC ACTATA.GGG AGGACGATGC GGTGCAATAA GAATCCTCCC TGCACCTGCA CGTAGCCTG GTC.AGACGA CTCGCCCGAG

CCGAAGCTTA A.TACGACTC ACTATA.GGG AGGACGATGC GGACAATCTC CCTACCCGCT TCAATCTTCC CCCTTCCTAC CTCA.GACGA CTCGCCCGAG
CCGAAGCTTA A.TACGACTC ACTATA.GGG AGGACGATGC GGACAATCTC CCTACCCGCT TCAATCTTCC CTCCTCCAAC CCCA.GACGA CTCGCCCGAG
CCGAAGCTTA A.TACGACTC ACTATA.GGG AGGACGATGC GGATGAGCCT CCTCGCATCG GGCAT.TTCC CTCCTTCTCC CCCA.GACGA CTCGCCCGAG

CCGAAGCTTA A.TACGACTC ACTATA.GGG AGGACGATGC GGGCAATGAC CAAGGTACCG ACCCTATGGC TCCGGCCTGC GTCA.GACGA CTCGCCCGAG
CCGAAGCTTA A.TACGACTC ACTATA.GGG AGGACGATGC GGGCAATGAC CAAGGTACCG ACCCTATGGC TCCGGCCTGC GTCA.GACGA CTCGCCCGAG
CCGAAGCTTA A.TACGACTC ACTATA.GGG AGGACGATGC GGGCAATGAC CAAGGTACCG ACCCTATGGC TCCGGCCTGC GTCA.GACGA CTCGCCCGAG
CCGAAGCTTA A.TACGACTC ACTATA.GGG AGGACGATGC GGGCAATGAC CAAGGTACCG ACCCTATGGC TCCGGCCTGC GTCA.GACGA CTCGCCCGAG
CCGAAGCTTA A.TACGACTC ACTATA.GGG AGGACGATGC GGGCAATGAC CAAGGTACCG ACCCTATGGC TCCGGCCTGC GTCA.GACGA CTCGCCCGAG
CCGAAGCTTA A.TACGACTC ACTATA.GGG AGGACGATGC GGGCAATGAC CAAGGTACCG ACCCTATGGC TCCGGCCTGC GTCA.GACGA CTCGCCCGAG
CCGAAGCTTA A.TACGACTC ACTATA.GGG AGGACGATGC GGGCAATGAC CAAGGTACCG ACCCTATGGC TCCGGCCTGC GTCA.GACGA CTCGCCCGAG
CCGAAGCTTA A.TACGACTC ACTATA.GGG AGGACGATGC GGGCAATGAC CAAGGTACCG ACCCTATGGC TCCGGCCTGC GTCA.GACGA CTCGCCCGAG
CCGAAGCTTA A.TACGACTC ACTATA.GGG AGGACGATGC GGGCAATGAC CAAGGTACCG ACCCTATGGC TCCGGCCTGC GTCA.GACGA CTCGCCCGAG
CCGAAGCTTA A.TACGACTC ACTATA.GGG AGGACGATGC GGGCANTGAC CAAGGTACCG ACCCTATGGC TCCGGCCTGC GTCA.GACGA CTCGCCCGAG
CCGAAGCTTA A.TACGACTC ACTATA.GGG AGGACGATGC GGGCAATGAC CAAGGTACCG ACCCTATGGC TCCGGCCTGC GTCA.GACGA CTCGCCCGAG
CCGAAGCTTA A.TACGACTC ACTATA.GGG AGGACGATGC GGGCAATGAC CAAGGTACCG ACCCTATGGC TCCGGCCTGC GTCA.GACGA CTCGCCCGAG
..GAAGCTTA A.TACGACTC ACTATA.GGG AGGACGATGC GGGCAATGAC CAAGGTACCG ACCCTATGGC TCCGGCCTGC GTCA.GACGA CTCGCCCGAG
```

*FIG. 16a*

```
NCNAARNNTA  A.NGCNACTC  ANTATA.GGG  AGNNCNATNC  GGGCAATGTC  CAAGGTACNN  ACCNTATGGN  NCCGGCNTGN  GTCA.GACGA  CTCGCCCGAG
CCGAAGCTTA  A.TACGACTC  ACTATA.GGG  AGGACGATGC  GGGCAATGAC  CAAGGNACCN  ACCCTATGGA  TCCGGCCTGC  NTNA.NACNA  CTNGACNGAG

CCGAAGCTTA  A.TACGACTC  ACTATA.GGG  AGGACGATGC  GGNNNCAGAN  CNNNGNNCNN  GNCCTGNNGA  TAACGTCNGC  GTCA.GACGA  CTCGCCCGAG
CGGCANCTTC  A.NNNNACTC  ACTATA.GGN  AGANNGANGC  GGACAATGNC  CAAGGNCCNG  GCCCTATGGC  TACGGCNTGG  GTCATGAGTN  NTCGNCCNAG
CCGAAGCTTA  A.TACGACTC  ACTATA.GGG  AGGACGATGC  GCACAACAC   CTCCAACTGC  ACCCTCTGAG  CATCATCCTG  GTCA.GACGA  CTCGCCCGAG
CCGAAGCTTA  A.TACGACTC  ACTATA.GGG  AGGACGATGC  GGCAAGTCAC  CTCCTGTTGC  GGCATAACTC  TCTCTCCGTG  GTCA.GACGA  CTCGCCCGAG

CCGAAGCTTA  A.TACGACTC  ACTATA.GGG  AGGACGATGC  GGTTAACTC   CCAACGCATC  AATCCCGATC  CGTGACTCCG  CCCA.GACGA  CTCGCCCGAG
CCGAAGCTT.  A.TACGACTC  ACTATA.GGG  AGGACGATGC  GGTTAACTC   CCAACGCATC  AATCCCGATC  CGTGATTCCG  CCCA.GACGA  CTCGCCCGAG
CCGAAGCTTA  A.TACGACTC  ACTATAGGGG  AGGACGATGC  GGTTAACTC   CCAACGCATC  AATCCCGATT  CGTGATTCCG  CCCA.GACGA  CTCGCCCGAG
CCGAAGCTTA  A.TACGACTC  ACTATA.GGG  AGGACGATGC  GGTTTANCTC  NCANCNNATC  AATCCATANC  CACNNNNCTG  CCNA.NANCA  ATTGGCCCAN

CCGAAGCTTA  A.TACGACTC  ACTATA.GGG  AGGACGATGC  GGTATCCTCC  AGAGCATCGC  CGTCCCATAAC CACTTACCTC  CCCA.GACGA  CTCGCCCGAG
CCGAAGCTTA  A.TACGACTC  ACTATA.GGG  AGGACGATGC  GGTATCCTCC  AGAGCATCGC  CGTCCCATAAC CACTTACCTC  CCCA.GACGA  CTCGCCCGAG
CCGAAGCTTA  A.TACGACTC  ACTATA.GGG  AGGACGATGC  GGTATCCTCC  AGAGCATCGC  CGTCCCATAAC CACTTACCTC  CTCA.GACGA  CTCGCCCGAG
CCGAAGCTTA  A.TACGACTC  ACTATA.GGG  AGGACGATGC  GG.ATCCTCC  AGAGCATCGC  CGTCCCATAAC CACTTACCTC  CCCA.GACGA  CTCGCCCGAG
CCGAAGCTTA  A.TACGACTC  ACTATA.GGG  AGGACGATGC  GGTATCNTCN  ANAGCATCNA  NNACCATAAC  CACTTNCTTC  TNAA.ANCAA  TTGGCCNANG
GCNAANTNA   A.TACCAATT  ACTATA.NGG  AGGACGATNC  NNNANTNNTG  GGCCGGTNNA  NGTCNATAAA  NTNATNCNTC  CTNA.GACGA  CTNGCCNTAN

CCGAAGCTTA  A.TACGACTC  ACTATA.GGG  AGGACGATGC  GGCATCTCCC  ACACTTCATC  GGCTCACCCT  ACTCCCCTGC  ATCA.GACGA  CTCGCCCGAG
CCGAAGCTTA  A.TACGACTC  ACTATA.GGG  AGGACGATGC  GGCATCTCCC  ACACTTCATC  GGTTCACCCT  ACTCCCCTGC  ATCA.GACGA  CTCGCCCGAG
CCGAAGCTTA  A.TACGACTC  ACTATA.GGG  AGGACGATGC  GGGCTCTCCC  ATCC..CATT  CGAAATCCCC  CCACGCTCTC  CCCA.GACGA  CTCGCCCGAG

CCGAAGCTTA  A.TACGACTC  ACTATA.GGG  AGGACGATGC  GGCCGTCCCG  TAGGCCAATT  GCGTCCCACC  TTAACGTCCG  CCCA.GACGA  CTCGCCCGAG
CCGAAGCTTA  A.TACGACTC  ACTATAGGGA GG..CGATGC  GGCATAGCCT  CCGATCCGCT  AACTCCGCT   CGCCAACTCC  TC..AGACGA CTCGCCCGAG
CCGAAGCTTA  A.TACGACTC  ACTATA.GGG  AGGACGATGC  GGAAGTCTGA  GTCAAATTGT  GCCACTCCCA  CTCCAATTGC  GTCA.GACGA CTCGCCCGAG
```

FIG. 16b

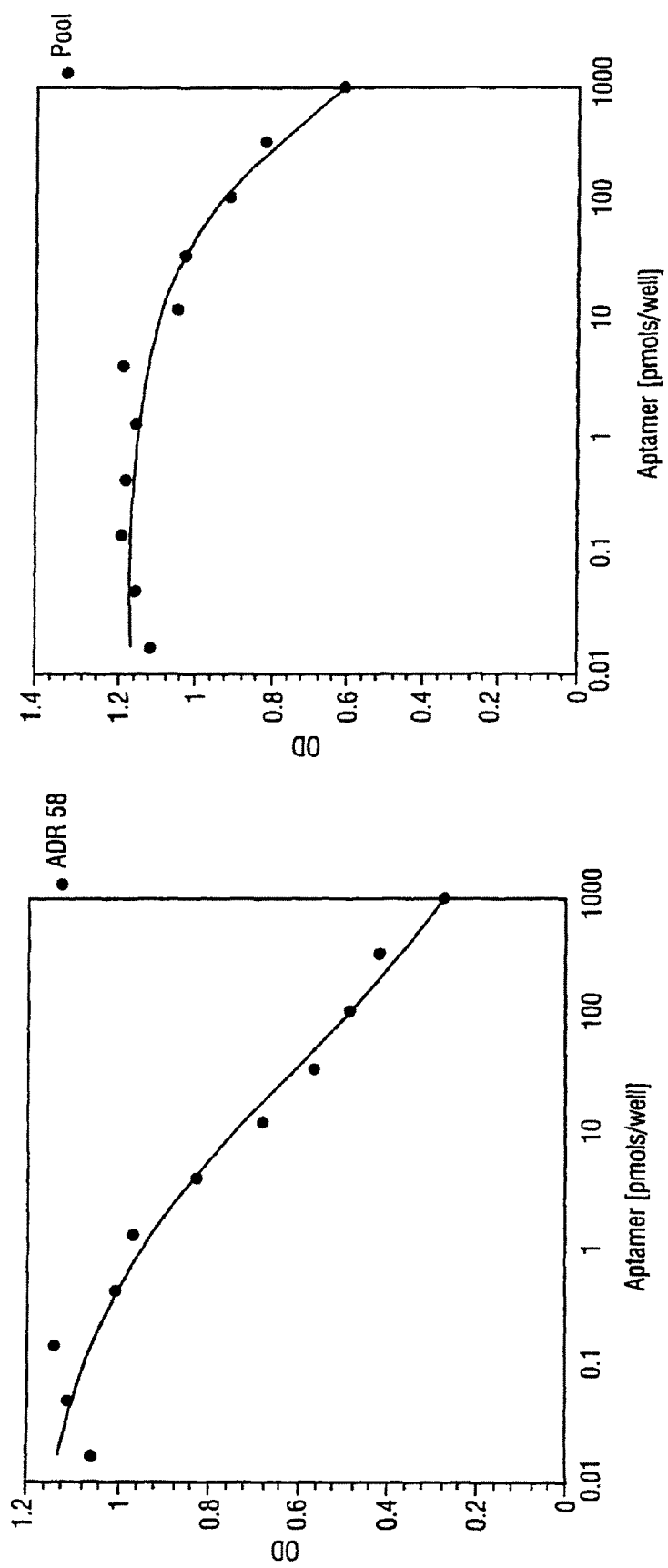

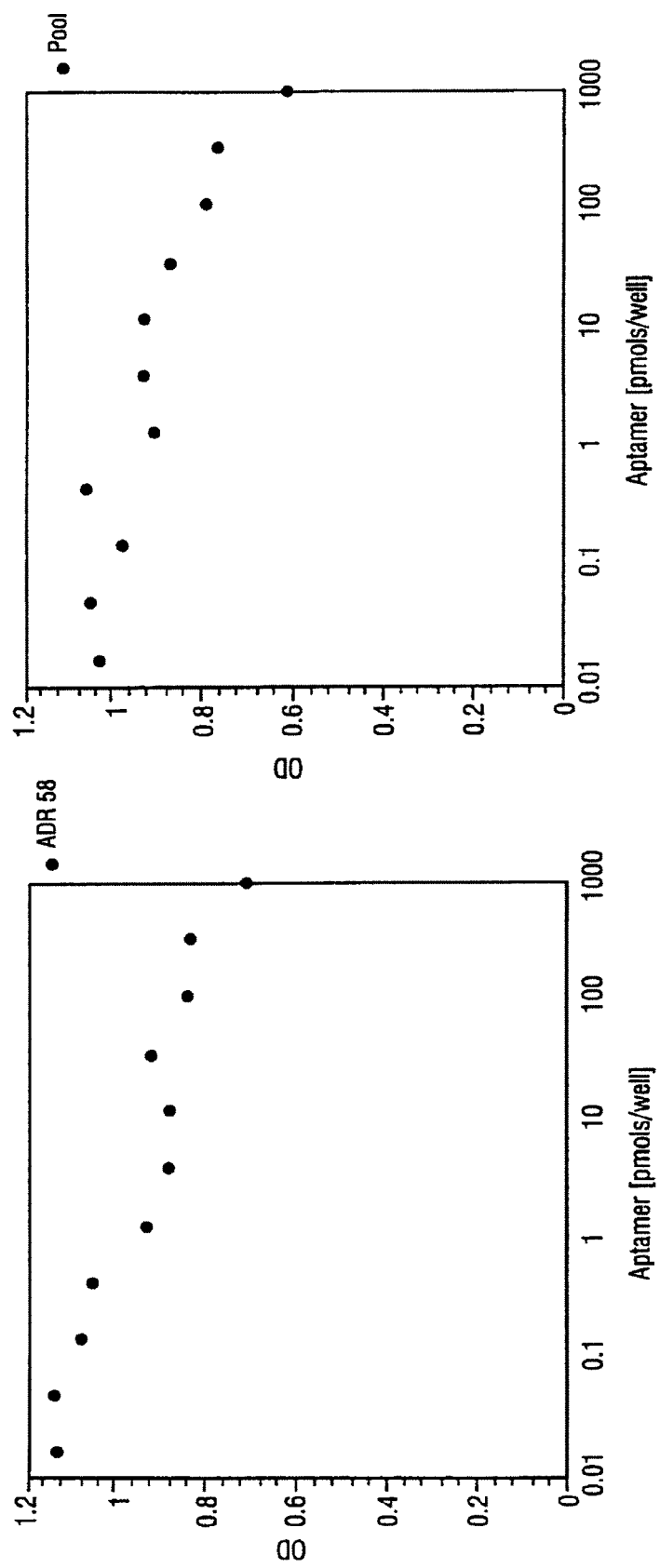

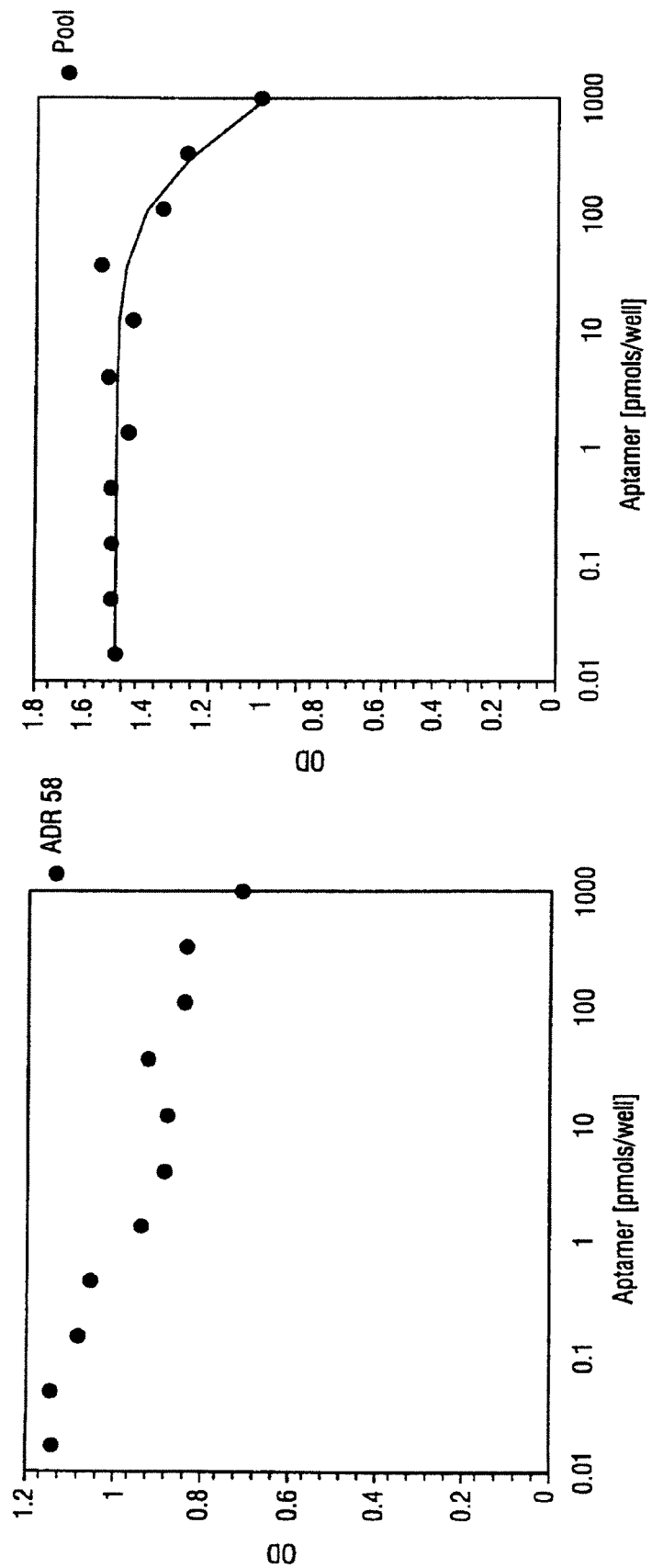

SEQUENCE LISTING

<160> NUMBER OF SEQ ID NOS: 61

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 1
gagtgacaag cctgtagccc atgttgtagc a                                    31

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 2
gcaatgatcc caaagtagac ctgcccagac                                          30

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 3
gggtgtccta ccaaggaaca                                                     20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 4
ctgagacctt tcaagaggac                                                     20

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 5
gcataggatc cgcggctata ggcagctgct cg                                       32

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 6
atcgcgaatt cctaccgggg cagctgtccc ct                                       32

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Synthetic
      sequence.
<220> FEATURE:
<221> NAME/KEY: CDS
<222> LOCATION: (1)..(45)

<400> SEQUENCE: 7 aaa tcg gat ctg atc gaa ggt cga cgg atc ccc ggg aat tca tcg            45
Lys Ser Asp Leu Ile Glu Gly Arg Arg Ile Pro Gly Asn Ser Ser
1               5                   10                  15

<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 8
gatacgatcg tctcatcgag cggctatagg cagctgc                                  37

```
<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 9
attacatgga attcctatct ccggctccgg ttcgg                          35

<210> SEQ ID NO 10
<211> LENGTH: 63
<212> TYPE: DNA
<213> ORGANISM: Artificial Sequence
<220> FEATURE:
<223> OTHER INFORMATION: Description of Artificial Sequence: Synthetic
      sequence.
<220> FEATURE:
<221> NAME/KEY: CDS
<222> LOCATION: (44)..(61)

<400> SEQUENCE: 10
catcggatcc aagctttaca gttactgagc acaggacctc acc atg ttg acg ttg    55
                                             Met Leu Thr Leu
                                              1 cag act tg                                                         63
Gln Thr
  5

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 11
catcctcgag tttctccttg agcaaacttt gg                               32

<210> SEQ ID NO 12
<211> LENGTH: 252
<212> TYPE: PRT
<213> ORGANISM: Homo sapiens

<400> SEQUENCE: 12

Met Gly Val Leu Leu Thr Gln Arg Thr Leu Leu Ser Leu Val Leu Ala
1               5                   10                  15

Leu Leu Phe Pro Ser Met Ala Ser Met Ala Ala Ile Gly Ser Cys Ser
                20                  25                  30

Lys Glu Tyr Arg Val Leu Leu Gly Gln Leu Gln Lys Gln Thr Asp Leu
            35                  40                  45

Met Gln Asp Thr Ser Arg Leu Leu Asp Pro Tyr Ile Arg Ile Gln Gly
        50                  55                  60

Leu Asp Val Pro Lys Leu Arg Glu His Cys Arg Glu Arg Pro Gly Ala
65                  70                  75                  80

Phe Pro Ser Glu Glu Thr Leu Arg Gly Leu Gly Arg Arg Gly Phe Leu
                85                  90                  95

Gln Thr Leu Asn Ala Thr Leu Gly Cys Val Leu His Arg Leu Ala Asp
            100                 105                 110

Leu Glu Gln Arg Leu Pro Lys Ala Gln Asp Leu Glu Arg Ser Gly Leu
        115                 120                 125

Asn Ile Glu Asp Leu Glu Lys Leu Gln Met Ala Arg Pro Asn Ile Leu
```

130                 135                 140
Gly Leu Arg Asn Asn Ile Tyr Cys Met Ala Gln Leu Leu Asp Asn Ser
145                 150                 155                 160

Asp Thr Ala Glu Pro Thr Lys Ala Gly Arg Gly Ala Ser Gln Pro Pro
                165                 170                 175

Thr Pro Thr Pro Ala Ser Asp Ala Phe Gln Arg Lys Leu Glu Gly Cys
            180                 185                 190

Arg Phe Leu His Gly Tyr His Arg Phe Met His Ser Val Gly Arg Val
        195                 200                 205

Phe Ser Lys Trp Gly Glu Ser Pro Asn Arg Ser Arg Arg His Ser Pro
    210                 215                 220

His Gln Ala Leu Arg Lys Gly Val Arg Arg Thr Arg Pro Ser Arg Lys
225                 230                 235                 240

Gly Lys Arg Leu Met Thr Arg Gly Gln Leu Pro Arg
                245                 250

<210> SEQ ID NO 13
<211> LENGTH: 5
<212> TYPE: PRT
<213> ORGANISM: Homo sapiens

<400> SEQUENCE: 13

Ala Ala Ile Gly Ser
1               5

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      sequence.

<400> SEQUENCE: 14

Lys Ser Asp Leu Ile Glu Gly Arg Arg Ile Pro Gly Asn Ser Ser
1               5                   10                  15

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      sequence.

<400> SEQUENCE: 15

Met Leu Thr Leu Gln Thr
1               5

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence:Primer

<400> SEQUENCE: 16
tcgggcgagt cgtctg                                                    16

<210> SEQ ID NO 17
<211> LENGTH: 40
<212> TYPE: DNA
<213> ORGANISM: Artificial Sequence
<220> FEATURE:

<223> OTHER INFORMATION: Description of Artificial Sequence:Primer

<400> SEQUENCE: 17
ccgaagctta atacgactca ctatagggag gacgatgcgg        40

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence:Primer

<400> SEQUENCE: 18
gccggatcct cgggcgagtc gtctg        25

<210> SEQ ID NO 19
<211> LENGTH: 105
<212> TYPE: DNA
<213> ORGANISM: Artificial Sequence
<220> FEATURE:
<223> OTHER INFORMATION: Description of Artificial Sequence:Primer

<400> SEQUENCE: 19
ccgaagctta atacgactca ctatagggag gacgatgcgg atcgccctga accggcccag        60
cagactgctg acggcacgat cagacgactc gcccgaggat ccggc        105

<210> SEQ ID NO 20
<211> LENGTH: 89
<212> TYPE: DNA
<213> ORGANISM: Artificial Sequence
<220> FEATURE:
<223> OTHER INFORMATION: Description of Artificial Sequence:Primer

<400> SEQUENCE: 20
taatacgact cactataggg aggacgatgc ggttatacta agctgcggtt agcgacagcc        60
ctccctagcg cctcagacga ctcgcccga        89

<210> SEQ ID NO 21
<211> LENGTH: 70
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: primer_bind
<222> LOCATION: (16)..(55)
<223> OTHER INFORMATION: n can be any nucleic acid

<400> SEQUENCE: 21
gggaggacga ugcggnnnnn nnnnnnnnnn nnnnnnnnnn nnnnnnnnnn nnnnccgca        60 tcgtcctccc        70

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 22
taatacgact cactataggg aggacgatgc gg        32

<210> SEQ ID NO 23
<211> LENGTH: 86
<212> TYPE: DNA

<213> ORGANISM: Artificial Sequence
<220> FEATURE:
<223> OTHER INFORMATION: Description of Artificial Sequence: Aptamer

<400> SEQUENCE: 23
aatacgactc actataggga ggacgatgcg gttatactag ctgcggttag cgacagccct    60
ccctagcgtc agacgactcg cccgag                                         86

<210> SEQ ID NO 24
<211> LENGTH: 96
<212> TYPE: DNA
<213> ORGANISM: Artificial Sequence
<220> FEATURE:
<223> OTHER INFORMATION: Description of Artificial Sequence: Aptamer

<400> SEQUENCE: 24
ccgaagctta atacgactca ctataggag gacgatgcgg tgacgcgatc cgccgttccc    60
atccgcacgc cctacacctc agacgactcg cccgag                              96

<210> SEQ ID NO 25
<211> LENGTH: 97
<212> TYPE: DNA
<213> ORGANISM: Artificial Sequence
<220> FEATURE:
<223> OTHER INFORMATION: Description of Artificial Sequence: Aptamer

<400> SEQUENCE: 25
ccgaagctta atacgactca ctatagggag gacgatgcgg aacaaagctg gagtacttac    60
cgaacatccg tctaacccct cagacgactc gcccgag                             97

<210> SEQ ID NO 26
<211> LENGTH: 98
<212> TYPE: DNA
<213> ORGANISM: Artificial Sequence
<220> FEATURE:
<223> OTHER INFORMATION: Description of Artificial Sequence: Aptamer

<400> SEQUENCE: 26
ccgaagctta atacgactca ctatagggag gacgatgcgg aacaaagctg gagtacttac    60
cgaacatccg tcctgacccc cagacgact cgcccgag                             98

<210> SEQ ID NO 27
<211> LENGTH: 97
<212> TYPE: DNA
<213> ORGANISM: Artificial Sequence
<220> FEATURE:
<223> OTHER INFORMATION: Description of Artificial Sequence: Aptamer

<400> SEQUENCE: 27
ccgaagctta atacgactca ctatagggag gacgatgcgg atcaccctga accggcccag    60
cagactgctg acggcacgat cagacgactc gcccgag                             97

<210> SEQ ID NO 28
<211> LENGTH: 97
<212> TYPE: DNA
<213> ORGANISM: Artificial Sequence
<220> FEATURE:
<223> OTHER INFORMATION: Description of Artificial Sequence: Aptamer

<400> SEQUENCE: 28
ccgaagctta atacgactca ctatagggag gacgatgcgg atcgccctga accggcccag    60
cagactgctg acggcacgac cagacgactc gcccgag                             97

<210> SEQ ID NO 29
<211> LENGTH: 97
<212> TYPE: DNA
<213> ORGANISM: Artificial Sequence
<220> FEATURE:
<223> OTHER INFORMATION: Description of Artificial Sequence: Aptamer

<400> SEQUENCE: 29
ccgaagctta atacgactca ctatagggag gacgatgcgg atcgccctga accggcccag      60
cagactgctg acggcacgat cagacgactc gcccgag                              97

<210> SEQ ID NO 30
<211> LENGTH: 97
<212> TYPE: DNA
<213> ORGANISM: Artificial Sequence
<220> FEATURE:
<223> OTHER INFORMATION: Description of Artificial Sequence: Aptamer

<400> SEQUENCE: 30
ccgaagctta atacgactca ctatagggag gacgatgcgg atcggtctga accggcccag      60
cagactgctg acggcacgat cagacgactc gcccgag                              97

<210> SEQ ID NO 31
<211> LENGTH: 98
<212> TYPE: DNA
<213> ORGANISM: Artificial Sequence
<220> FEATURE:
<223> OTHER INFORMATION: Description of Artificial Sequence: Aptamer
<220> FEATURE:
<221> NAME/KEY: misc_feature
<222> LOCATION: (7)
<223> OTHER INFORMATION: n = any of a, c, g, or t

<400> SEQUENCE: 31
ccgaagntta attacgactc actataggga gaacgatgcg gatcgctctg aaccggccca      60
gcagactgct gacggcacga tcagacgact cgcccgag                             98

<210> SEQ ID NO 32
<211> LENGTH: 96
<212> TYPE: DNA
<213> ORGANISM: Artificial Sequence
<220> FEATURE:
<223> OTHER INFORMATION: Description of Artificial Sequence: Aptamer

<400> SEQUENCE: 32
ccgaagctta atacgaactc actataggga ggacgatgcg gatccctgaa ccggcccagc      60
agactactga cggcacgatc agacgactcg cccgag                               96

<210> SEQ ID NO 33
<211> LENGTH: 98
<212> TYPE: DNA
<213> ORGANISM: Artificial Sequence
<220> FEATURE:
<223> OTHER INFORMATION: Description of Artificial Sequence: Aptamer
<220> FEATURE:
<221> NAME/KEY: misc_feature
<222> LOCATION: 44, 49..54, 59, 60, 73, 77
<223> OTHER INFORMATION: n = any of a, c, g, or t

<400> SEQUENCE: 33
ccgaagctta atacgactca ctatagggag gacgatgcgg atcntcttnn nnnnttccnn      60
cacactgaat acntccngat caagacgact cgcccgag                             98

<210> SEQ ID NO 34

```
<211> LENGTH: 96
<212> TYPE: DNA
<213> ORGANISM: Artificial Sequence
<220> FEATURE:
<223> OTHER INFORMATION: Description of Artificial Sequence: Aptamer

<400> SEQUENCE: 34
cgaagcttaa tacgactcac tatagggagg acgatgcggt gcaataagaa tcctccctgc      60
acctgcacgt aggcctggtc agacgactcg cccgag                                96

<210> SEQ ID NO 35
<211> LENGTH: 97
<212> TYPE: DNA
<213> ORGANISM: Artificial Sequence
<220> FEATURE:
<223> OTHER INFORMATION: Description of Artificial Sequence: Aptamer

<400> SEQUENCE: 35
ccgaagctta atacgactca ctatagggag gacgatgcgg acaatctccc tacccgcttc      60
aatcttcccc cttcctacct cagacgactc gcccgag                               97

<210> SEQ ID NO 36
<211> LENGTH: 97
<212> TYPE: DNA
<213> ORGANISM: Artificial Sequence
<220> FEATURE:
<223> OTHER INFORMATION: Description of Artificial Sequence: Aptamer

<400> SEQUENCE: 36
ccgaagctta atacgactca ctatagggag gacgatgcgg acaatctccc tacccgcttc      60
aatcttccct cctccaaccc cagacgactc gcccgag                               97

<210> SEQ ID NO 37
<211> LENGTH: 96
<212> TYPE: DNA
<213> ORGANISM: Artificial Sequence
<220> FEATURE:
<223> OTHER INFORMATION: Description of Artificial Sequence: Aptamer

<400> SEQUENCE: 37
ccgaagctta atacgactca ctatagggag gacgatgcgg atgagcctcc tcgcatcggg      60
catttccctc cttctccccc agacgactcg cccgag                                96

<210> SEQ ID NO 38
<211> LENGTH: 97
<212> TYPE: DNA
<213> ORGANISM: Artificial Sequence
<220> FEATURE:
<223> OTHER INFORMATION: Description of Artificial Sequence: Aptamer

<400> SEQUENCE: 38
ccgaagctta atacgactca ctatagggag gacgatgcgg gcaatgacca aggtaccgac      60
cctatggctc cggcctgcgt cagacgactc gcccgag                               97

<210> SEQ ID NO 39
<211> LENGTH: 95
<212> TYPE: DNA
<213> ORGANISM: Artificial Sequence
<220> FEATURE:
<223> OTHER INFORMATION: Description of Artificial Sequence: Aptamer

<400> SEQUENCE: 39
gaagcttaat acgactcact atagggagga cgatgcgggc aatgaccaag gtaccgaccc      60
```

```
tatggctccg gcctgcgtca gacgactcgc ccgag                              95
```

<210> SEQ ID NO 40
<211> LENGTH: 97
<212> TYPE: DNA
<213> ORGANISM: Artificial Sequence
<220> FEATURE:
<223> OTHER INFORMATION: Description of Artificial Sequence: Aptamer
<220> FEATURE:
<221> NAME/KEY: misc_feature
<222> LOCATION: 1, 3, 6..8, 12, 15, 21, 31, 32, 34, 37, 57, 58, 62, 68, 69
<223> OTHER INFORMATION: n = any of a, c, g, or t
<220> FEATURE:
<221> NAME/KEY: misc_feature
<222> LOCATION: 75, 78
<223> OTHER INFORMATION: n = any of a, c, g, or t
<400> SEQUENCE: 40

```
ncnaannnta angcnactca ntataggagg nncnatncgg gcaatgtcca aggtacnnac   60
cntatggnnc cggcntgngt cagacgactc gcccgag                           97
```

<210> SEQ ID NO 41
<211> LENGTH: 97
<212> TYPE: DNA
<213> ORGANISM: Artificial Sequence
<220> FEATURE:
<223> OTHER INFORMATION: Description of Artificial Sequence: Aptamer
<220> FEATURE:
<221> NAME/KEY: misc_feature
<222> LOCATION: 54, 58, 79, 81, 83, 86, 90, 94
<223> OTHER INFORMATION: n = any of a, c, g, or t
<400> SEQUENCE: 41

```
ccgaagctta atacgactca ctatagggag gacgatgcgg gcaatgacca aggnaccnac   60
cctatggatc cggcctgcnt nanacnactn gacngag                           97
```

<210> SEQ ID NO 42
<211> LENGTH: 97
<212> TYPE: DNA
<213> ORGANISM: Artificial Sequence
<220> FEATURE:
<223> OTHER INFORMATION: Description of Artificial Sequence: Aptamer
<220> FEATURE:
<221> NAME/KEY: misc_feature
<222> LOCATION: 41..43, 48, 50..52, 54, 55, 57, 58, 60, 65, 66, 76
<223> OTHER INFORMATION: n = any of a, c, g, or t
<400> SEQUENCE: 42

```
ccgaagctta atacgactca ctatagggag gacgatgcgg nnncagancn nngnncnngn   60
cctgnngata acgtcngcgt cagacgactc gcccgag                           97
```

<210> SEQ ID NO 43
<211> LENGTH: 98
<212> TYPE: DNA
<213> ORGANISM: Artificial Sequence
<220> FEATURE:
<223> OTHER INFORMATION: Description of Artificial Sequence: Aptamer
<220> FEATURE:
<221> NAME/KEY: misc_feature
<222> LOCATION: 6, 12..15, 28, 32, 33, 36, 47, 54, 57, 75, 88, 89, 93, 96
<223> OTHER INFORMATION: n = any of a, c, g, or t
<400> SEQUENCE: 43

```
cggcanctta annnnactca ctataggnag anngangcgg acaatgncca aggnccnggc   60
cctatggcta cggcntgggt catgagtnnt cgnccnag                          98
```

<210> SEQ ID NO 44
<211> LENGTH: 97
<212> TYPE: DNA
<213> ORGANISM: Artificial Sequence
<220> FEATURE:
<223> OTHER INFORMATION: Description of Artificial Sequence: Aptamer

<400> SEQUENCE: 44
ccgaagctta atacgactca ctatagggag gacgatgcgg cacaacacct ccaactgcac    60
cctctgagca tcatcctggt cagacgactc gcccgag                            97

<210> SEQ ID NO 45
<211> LENGTH: 97
<212> TYPE: DNA
<213> ORGANISM: Artificial Sequence
<220> FEATURE:
<223> OTHER INFORMATION: Description of Artificial Sequence: Aptamer

<400> SEQUENCE: 45
ccgaagctta atacgactca ctatagggag gacgatgcgg caagtcacct cctgttgcgg    60
cataactctc tctccgtggt cagacgactc gcccgag                            97

<210> SEQ ID NO 46
<211> LENGTH: 97
<212> TYPE: DNA
<213> ORGANISM: Artificial Sequence
<220> FEATURE:
<223> OTHER INFORMATION: Description of Artificial Sequence: Aptamer

<400> SEQUENCE: 46
ccgaagctta atacgactca ctatagggag gacgatgcgg tttaactccc aacgcatcaa    60
tcccgatccg tgactccgcc cagacgactc gcccgag                            97

<210> SEQ ID NO 47
<211> LENGTH: 96
<212> TYPE: DNA
<213> ORGANISM: Artificial Sequence
<220> FEATURE:
<223> OTHER INFORMATION: Description of Artificial Sequence: Aptamer

<400> SEQUENCE: 47
ccgaagctta tacgactcac tagggaggag acgatgcggt ttaactccca acgcatcaat    60
cccgatccgt gattccgccc agacgactcg cccgag                             96

<210> SEQ ID NO 48
<211> LENGTH: 98
<212> TYPE: DNA
<213> ORGANISM: Artificial Sequence
<220> FEATURE:
<223> OTHER INFORMATION: Description of Artificial Sequence: Aptamer

<400> SEQUENCE: 48
ccgaagctta atacgactca ctatagggga ggacgatgcg gtttaactcc caacgcatca    60
atcccgattc gtgattccgc ccagacgact cgcccgag                           98

<210> SEQ ID NO 49
<211> LENGTH: 97
<212> TYPE: DNA
<213> ORGANISM: Artificial Sequence
<220> FEATURE:
<223> OTHER INFORMATION: Description of Artificial Sequence: Aptamer
<220> FEATURE:
<221> NAME/KEY: misc_feature
<222> LOCATION: 45, 49, 52, 54, 55, 67, 72..75, 81, 83, 85, 97

```
<223> OTHER INFORMATION: n = any of a, c, g, or t

<400> SEQUENCE: 49
ccgaagctta atacgactca ctatagggag gacgatgcgg tttanctcnc ancnnatcaa    60
tccatancca cnnnnctgcc nanancaatt ggcccan                              97

<210> SEQ ID NO 50
<211> LENGTH: 97
<212> TYPE: DNA
<213> ORGANISM: Artificial Sequence
<220> FEATURE:
<223> OTHER INFORMATION: Description of Artificial Sequence: Aptamer

<400> SEQUENCE: 50
ccgaagctta atacgactca ctatagggag gacgatgcgg tatcctccag agcatcgccg    60
tccataacca cttacctccc cagacgactc gcccgag                              97

<210> SEQ ID NO 51
<211> LENGTH: 97
<212> TYPE: DNA
<213> ORGANISM: Artificial Sequence
<220> FEATURE:
<223> OTHER INFORMATION: Description of Artificial Sequence: Aptamer

<400> SEQUENCE: 51
ccgaagctta atacgactca ctatagggag gacgatgcgg tatcctccag agcatcgccg    60
tccataacca cttacctcct cagacgactc gcccgag                              97

<210> SEQ ID NO 52
<211> LENGTH: 96
<212> TYPE: DNA
<213> ORGANISM: Artificial Sequence
<220> FEATURE:
<223> OTHER INFORMATION: Description of Artificial Sequence: Aptamer

<400> SEQUENCE: 52
ccgaagctta atacgactca ctatagggag gacgatgcgg atcctccaga gcatcgccgt    60
ccataaccac ttacctcccc agacgactcg cccgag                               96

<210> SEQ ID NO 53
<211> LENGTH: 97
<212> TYPE: DNA
<213> ORGANISM: Artificial Sequence
<220> FEATURE:
<223> OTHER INFORMATION: Description of Artificial Sequence: Aptamer
<220> FEATURE:
<221> NAME/KEY: misc_feature
<222> LOCATION: 45, 48, 50, 57, 59, 60, 74, 80, 84, 94, 96
<223> OTHER INFORMATION: n = any of a, c, g, or t

<400> SEQUENCE: 53
ccgaagctta atacgactca ctatagggag gacgatgcgg tatcntcnan agcatcnann    60
accataacca cttncttctn aaancaattg gccnang                              97

<210> SEQ ID NO 54
<211> LENGTH: 97
<212> TYPE: DNA
<213> ORGANISM: Artificial Sequence
<220> FEATURE:
<223> OTHER INFORMATION: Description of Artificial Sequence: Aptamer
<220> FEATURE:
<221> NAME/KEY: misc_feature
<222> LOCATION: 3, 7, 9, 26, 37, 39..41, 43, 45, 46, 56, 57, 59, 63
<223> OTHER INFORMATION: n = any of a, c, g, or t
<220> FEATURE:
```

```
<221> NAME/KEY: misc_feature
<222> LOCATION: 69, 71, 74, 76, 81, 90, 94, 97
<223> OTHER INFORMATION: n = any of a, c, g, or t

<400> SEQUENCE: 54
gcnaaantna ataccaatta ctatanggag gacgatncnn nantnntggg ccggtnnang      60
tcnataaant natncntcct nagacgactn gccntan                              97

<210> SEQ ID NO 55
<211> LENGTH: 97
<212> TYPE: DNA
<213> ORGANISM: Artificial Sequence
<220> FEATURE:
<223> OTHER INFORMATION: Description of Artificial Sequence: Aptamer

<400> SEQUENCE: 55
ccgaagctta atacgactca ctataggnag gacgatgcgg catctcccac acttcatcgg      60
ctcaccctac tcccttgcat cagacgactc gcccgag                              97

<210> SEQ ID NO 56
<211> LENGTH: 97
<212> TYPE: DNA
<213> ORGANISM: Artificial Sequence
<220> FEATURE:
<223> OTHER INFORMATION: Description of Artificial Sequence: Aptamer

<400> SEQUENCE: 56
ccgaagctta atacgactca ctatagggag gacgatgcgg catctcccac acttcatcgg      60
ttcaccctac tcccttgcat cagacgactc gcccgag                              97

<210> SEQ ID NO 57
<211> LENGTH: 95
<212> TYPE: DNA
<213> ORGANISM: Artificial Sequence
<220> FEATURE:
<223> OTHER INFORMATION: Description of Artificial Sequence: Aptamer

<400> SEQUENCE: 57
ccgaagctta atacgactca ctatagggag gacgatgcgg gctctcccat cccattcgaa      60 atcccccac gctctcccca gacgactcgc ccgag                                 95

<210> SEQ ID NO 58
<211> LENGTH: 97
<212> TYPE: DNA
<213> ORGANISM: Artificial Sequence
<220> FEATURE:
<223> OTHER INFORMATION: Description of Artificial Sequence: Aptamer

<400> SEQUENCE: 58
ccgaagctta atacgactca ctatagggag gacgatgcgg ccgtcccgta ggccaattgc      60
gtcccacctt aacgtccgcc cagacgactc gcccgag                              97

<210> SEQ ID NO 59
<211> LENGTH: 95
<212> TYPE: DNA
<213> ORGANISM: Artificial Sequence
<220> FEATURE:
<223> OTHER INFORMATION: Description of Artificial Sequence: Aptamer

<400> SEQUENCE: 59
ccgaagctta atacgactca ctatagggag gcgatgcggc atagcctccg atccgctaac      60
tctaacccgc caactcctca gacgactcgc ccgag                                95
```

```
<210> SEQ ID NO 60
<211> LENGTH: 97
<212> TYPE: DNA
<213> ORGANISM: Artificial Sequence
<220> FEATURE:
<223> OTHER INFORMATION: Description of Artificial Sequence: Aptamer

<400> SEQUENCE: 60
ccgaagctta atacgactca ctatagggag gacgatgcgg aagtctgagt caaattgtgc      60
cactcccact ccaattgcgt cagacgactc gcccgag                              97

<210> SEQ ID NO 61
<211> LENGTH: 98
<212> TYPE: DNA
<213> ORGANISM: Artificial Sequence
<220> FEATURE:
<223> OTHER INFORMATION: Description of Artificial Sequence: Aptamer
<220> FEATURE:
<221> NAME/KEY: misc_feature
<222> LOCATION: 42, 46, 54..56, 58, 59, 62, 72, 79, 80
<223> OTHER INFORMATION: n = any of a, c, g, or t

<400> SEQUENCE: 61
ccgaagctta atacgactca ctatagggag gacgatgcgg ancgangtgc tcannntnna      60
antctaggct ancacccnn aaacacaatt gccccagg                              98
```

INFLAMMATORY MEDIATOR ANTAGONISTS

This is a continuation of prior U.S. Ser. No. 11/260,844 filed on Oct. 27, 2005, which granted on Nov. 6, 2007 as U.S. Pat. No. 7,291,332, which is a continuation of application Ser. No. 10/442,289 filed on May 21, 2003, now abandoned, which is a continuation of Ser. No. 09/276,147 filed on Mar. 25, 1999, which granted on Mar. 16, 2004 as U.S. Pat. No. 6,706,266, all of the proceeding are incorporated herein by reference in their entirety which claims priority to foreign application GB9806530 filed on Mar. 26, 1998.

The present invention relates to the use of an antagonist of OSM in the manufacture of a medicament for the treatment or prophylaxis of an inflammatory arthropathy or inflammatory disorder and methods of screening for such antagonists.

Rheumatoid arthritis (RA) is a chronic inflammatory disease that affects articular joints, characterised by synovial hyperplasia and extensive cellular infiltration by mononuclear cells and polymorphonuclear leukocytes (PMN). A complex, and poorly understood interplay between resident and infiltrating cell types leads to the chronic secretion of metalloproteinases (MMPs), resulting in destruction of articular cartilage, ligaments and subchondral bone (Firestein G S Current Opinion in Rheumatology. 4:348-54, 1992). Among the numerous pro-inflammatory cytokines implicated in driving RA joint pathology, TNFα has been shown to play a pivotal role, with anti-TNFα therapies showing clear benefit (Elliott M J. et al. Lancet. 344(8930):1105-10, 1994). TNFα mediates several pathologic effects including induction of MMPs (Dayer J M. et al Journal of Experimental Medicine. 162(6):2163-8, 1985), upregulation of other pro-inflammatory cytokines (Haworth C. et al. European Journal of Immunology. 21(10):2575-9, 1991 and Dinarello C A. et al. Journal of Experimental Medicine. 163(6):1433-50, 1986) and increased PMN adhesion and transendothelial cell migration (Smart S J. Casale T B American Journal of Physiology. 266:L238-45, 1994). Though TNFα is viewed currently as the initiator of the pro-inflammatory cytokine cascade, relatively little is known of its positive regulation (Feldmann M. et al. Annual Review of Immunology. 14:397-440, 1996).

Oncostatin M (OSM) (Rose T M. Bruce A G. PNAS USA 88(19):8641-5, 1991) is a 28 kDa glycoprotein which belongs to a family of cytokines comprising IL-6, IL-11, leukaemia inhibitory factor (LIF), cililiary neurotrophic factor (CNTF) and cardiotrophin 1 (CT-1)(Taga T. Kishimoto T. Annual Review of Immunology. 15:797-819, 1997). All members share a common signalling chain, gp130, as part of a complex family of hetero- and homodimeric receptors (Grotzinger J. et al. [Article] Proteins. 27(1):96-109, 1997). OSM shares a common heterodimeric receptor with LIF, (LIFr: gp130, type I) and also has its own unique receptor comprising OSMrβ chain and gp130 (type II) (Mosley B. et al. [Article] Journal Of Biological Chemistry. 271(51):32635-32643, 1996). OSM has long been known for effects on cell growth and differentiation (Horn D. et al [Journal Article] Growth Factors. 2(2-3): 157-65, 1990). Recently, OSM has also been shown to have potent, pro-inflammatory properties in mice in vivo (Modur V. et al. J. Clin Invest. 100:158-168, 1997) and demonstrates potent synergy with IL-1 to promote articular cartilage degradation in model systems, ex-vivo (Cawston T. Biochemical & Biophysical Research Communications. 215 (1):377-85, 1995).

OSM induces a prolonged increase in P-selectin (and E-selectin) in endothelial cells (Yao L. et al. Journal Of Experimental Medicine. 184(1):81-92, 1996), stimulates urokinase-type plasminogen activator activity in human synovial fibroblasts (Hamilton J. et al Biochemical & Biophysical Research Communications. 180(2):652-9, 1991) and is a powerful inducer of IL-6 from endothelial cells (Brown T j. et al. Journal Of Immunology. 147(7):2175-80, 1991 Oct. 1). OSM has recently been measured in RA but not OA synovial fluid (Hui W. et al. Annals Of The Rheumatic Diseases. 56(3): 184-187, 1997) and synovium, production of which has been localised to macrophages (1997, Okamoto H et al. Arthritis and Rheumatism 40(6): 1096-1105) and Cawston et al (1998, Arthritis and Rheumatism, 41(10) 1760-1771). To-date further experiments in this field have been speculative based on the similarity of the IL-6 subfamily members (Carroll G. et al Inflamm. Res. 47 (1998) 1-7).

The present inventors have discovered that OSM has the ability to induce TNFα secretion in macrophages. Contrary to recent data suggesting that OSM upregulates production of tissue inhibitor of metalloproteinase-1 (TIMP-1) (Nemoto et al 1996, A&R 39(4), 560-566), which complexes with and inactivates MMP-1 and would therefore be expected to decrease collagen release, the inventors discovery that OSM induces TNFα secretion suggested to them that OSM may actually play a role in mediating cartilage destruction. Based on this discovery, the present inventors have demonstrated that therapeutic administration of a neutralising anti-OSM antibody without inhibition of other IL-6 family members can alone ameliorate collagen-induced arthritis in a mouse model. Synergy of OSM with TNFα to promote collagen release from cartilage has subsequently been shown by T. Cawston et al (1998, Arthritis and Rheumatism, 41(10) 1760-1771).

According to the present invention there is therefore provided the use of an antagonist of OSM in the manufacture of a medicament for the treatment or prophylaxis of an inflammatory arthropathy or inflammatory disorder. A particular use of an antagonist of OSM is in the manufacture of a medicament to prevent or reduce collagen release from cartilage. The invention further provides a method for the treatment or prophylaxis of an inflammatory arthropathy or inflammatory disorder comprising administering an effective amount of an antagonist of OSM to a patient suffering from such a disorder.

The antagonist may function by blocking OSM from interaction with the OSM receptor gp130, or the other OSM receptors, OSMrβ chain or LIFr, or by blocking formation of heterodimers of these proteins, and as such prevent OSM binding and signalling thereby reducing synthesis of pro-inflammatory cytokines and/or MMPs. The antagonist according to the invention may therefore be a ligand for either OSM or one or more of the OSM receptors (gp130, OSMrβ or LIFr) or an agent capable of interfering with these interactions in a manner which affects OSM biological activity. Hereinafter reference to an antagonist to OSM can be taken to mean either an antagonist to OSM itself or to one of its receptors.

The present inventors have also demonstrated that in rheumatoid arthritis synovial vascular endothelium, P and E-selectin co-localise with gp130, the signalling element of type I and II OSM receptors. Without wishing to be bound by theory this indicates that OSM, produced by synovial macrophages might prime RA vascular endothelium to facilitate leucocyte recruitment via upregulation of P and E-selectin. The finding that ligation of L-selectin by either specific antibody or fucoidan (L-selectin agonist) drives human mononuclear cells to secrete OSM may be highly significant in terms of amplification of the inflammatory response, by providing an additional local source of OSM to drive TNFα and P and E-selectin.

Amino acid residues which are important for OSM's interaction with gp130 have been identified. From the published amino acid sequence of OSM (Malik et al., 1989, Mol. Cell. Biol., 9(7), 2847-53, DNA sequence entry M27288 in EMBL database, protein sequence entry P13725 in Swissprot) these are G120, Q16 and Q20; N123 and N124 may also play a part (see SEQ ID 12 and below). The first 25 residues are a signal peptide, and the mature protein begins at the sequence AAIGS (SEQ ID 13). The sequence is numbered from the first amino acid of the mature protein as shown.

```
                                                         SEQ ID 12
            1     5               15             25              35
MGVLLTQRTL LSLVLALLFP SMASMAAIGS CSKEYRVLLG QLQKQTDLMQ DTSRLLDPYI 45            55             65             75             85             95
RIQGLDVPKL REHCRERPGA FPSEETLRGL GRRGFLQTLN ATLGCVLHRL ADLEQRLPKA 105           115            125            135            145            155
QDLERSGLNI EDLEKLQMAR PNILGLRNNI YCMAQLLDNS DTAEPTKAGR GASQPPTPTP 165           175            185            195            205            215
ASDAFQRKLE GCRFLHGYHR FMHSVGRVFS KWGESPNRSR RHSPHQALRK GVRRTRPSRK 225 227
GKRLMTRGQL PR
```

The invention therefore further provides an antagonist or agent capable of interacting with one or more of these specific residues and or the binding sites they help to define on OSM to alter OSM biological activity.

Inflammatory arthropathies which may be treated according to this invention include rheumatoid arthritis, psoriatic arthritis, juvenile arthritis, inflammatory osteoarthritis and/or reactive arthritis. Inflammatory disorders which may be treated include, amongst others, Crohns disease, ulcerative colitis, gastritis for example gastritis resulting from *H. pylori* infection, asthma, chronic obstructive pulmonary disease, alzheimer's disease, multiple sclerosis and psoriasis.

Potential antagonists of OSM include small organic molecules, ions which interact specifically with OSM for example a substrate possibly a natural substrate, a cell membrane component, a receptor or a natural ligand, a fragment thereof or a peptide or other proteinaceous molecule, particularly preferred is a non-signalling mutant form of OSM which will block binding of OSM to the OSM receptor, but also modified OSM molecules. Such antagonists may be in the form of DNA encoding the protein or peptide and may be delivered for in vivo expression of said antagonist. Antagonists may be vaccines comprising such protein or peptide molecules or DNA, designed to produce an antagonistic effect towards OSM via induction of antibody responses in vivo targeted towards native OSM. Such antagonists may also include antibodies, antibody-derived reagents or chimaeric molecules. Included in the definition of antagonist is a structural or functional mimetic of any such molecule described above. Also contemplated are nucleic acid molecules such as DNA or RNA aptamers.

Preferred antagonists include small organic molecules. Such compounds may be from any class of compound but will be selected on the basis of their ability to affect the biological activity of OSM through one of the mechanisms described above and will be physiologically acceptable ie non-toxic or demonstrating an acceptable level of toxicity or other side-effects. One class of compounds which may provide useful antagonists are ribonucleosides such as N-(1H-pyrazolo[3,4-d]pyrimidin-4-yl) benzamide); Davoll and Kerridge, J. Chem Soc., 2589, 1961)

Other preferred antagonists include antibodies, fragments thereof or artificial constructs comprising antibodies or fragments thereof or artificial constructs designed to mimic the binding of antibodies or fragments thereof. Such constructs are discussed by Dougall et al in Tibtech 12, 372-379) (1994).

Also included in the definition of antibody are recombinant antibodies such as recombinant human antibodies, which may be used. The antibodies may be altered ie they may be "chimaeric" antibodies comprising the variable domains of a donor antibody and the constant domains of a human antibody (as described in WO86/01533) or they may be "humanised" antibodies in which only the CDRs are derived from a different species than the framework of the antibody's variable domains (as disclosed in EP-A-0239400). The complementarity determining regions (CDRs) may be derived from a rodent or primate monoclonal antibody. The framework of the variable domains, and the constant domains, of the altered antibody are usually derived from a human antibody. Such a humanised antibody should not elicit as great an immune response when administered to a human compared to the immune response mounted by a human against a wholly foreign antibody such as one derived from a rodent.

Preferred antagonists include complete antibodies, F(ab')$_2$ fragments, Fab fragments, Fv fragments, ScFv fragments, other fragments, CDR peptides and mimetics. These can be obtained/prepared by those skilled in the art. For example, enzyme digestion can be used to obtain F(ab')$_2$ and Fab fragments (by subjecting an IgG molecule to pepsin or papain cleavage respectively). References to "antibodies" in the following description should be taken to include all of the possibilities mentioned above.

As will be appreciated by those skilled in the art, where specific protein or peptide antagonists are described herein, derivatives of such antagonists can also be used. The term "derivative" includes variants of the antagonists described, having one or more amino acid substitutions, deletions or insertions relative to said antagonists, whilst still having the binding activity described. Preferably these derivatives have substantial amino acid sequence identity with the antagonists specified.

The degree of amino acid sequence identity can be calculated using a program such as "bestfit" (Smith and Waterman, Advances in Applied Mathematics, 482-489 (1981)) to find the best segment of similarity between any two sequences. The alignment is based on maximising the score achieved using a matrix of amino acid similarities, such as that described by Schwarz and Dayhof (1979) Atlas of Protein Sequence and Structure, Dayhof, M. O., Ed pp 353-358.

Preferably the degree of sequence identity is at least 50% and more preferably it is at least 75%. Sequence identities of at least 90% or of at least 95% are most preferred. It will nevertheless be appreciated by the skilled person that high degrees of sequence identity are not necessarily required since various amino acids may often be substituted for other amino acids which have similar properties without substantially altering or adversely affecting certain properties of a protein. These are sometimes referred to as "conservative" amino acid changes. Thus the amino acids glycine, valine, leucine or isoleucine can often be substituted for one another include: —phenylalanine, tyrosine and tryptophan (amino acids having aromatic side chains); lysine, arginine and histidine (amino acids having basic side chains); asparate and glutamate (amino acids having acidic side chains); asparagine and glutamine (amino acids having amide side chains) and cysteine and methionine (amino acids having sulphur containing side chains). Thus the term "derivative" can also include a variant of an amino acid sequence comprising one or more such "conservative" changes relative to said sequence.

The present invention also includes fragments of the antagonists of the present invention or of derivatives thereof which still have the binding activity described. Preferred fragments are at least ten amino acids long, but they may be longer (e.g. up to 50 or up to 100 amino acids long).

Further preferred antagonists of OSM for use in the invention are oligonucleotide ligands. Systematic evolution of ligands by exponential enrichment (SELEX) is a protocol in which vast libraries of single stranded oligonucleotides are screened for desired activity against a target protein or other molecule (Tuerk & Gold 1990 Science 249, 505-510, Green et al., 1991 Meths. Enzymol. 2 75-86; Gold et al., 1995 Annu. Rev Biochem 64, 763-797; Uphof et al., 1996 Curr. Opin. Struct. Biol. 6, 281-288). The product of this screen is a single oligonucleotide sequence termed an aptamer with desired activity, usually high affinity binding, for the target protein. The SELEX procedure is usually initiated with an RNA or DNA library consisting of some $10^{14}$-$10^{15}$ random oligonucleotide sequences. In a fully randomised oligonucleotide library, each molecule will exhibit a unique tertiary structure which will be entirely dependent on the nucleotide sequence of that molecule. Thus when screened against a target protein the binding affinity of the oligonucleotide for that protein will be determined by the fit between the shape of the oligonucleotide and epitopes on the target protein. As a consequence of starting from a library of vast diversity it is usual to be able to identify aptamers of sub-nM affinity for the target protein with selectivity for that target protein over other proteins with overall structural homology (Tuerk & Gold 1990 supra, Green et al., 1991 supra; Gold et al., 1995 supra; Uphof et al., 1996 supra). Using SELEX methodology RNA or DNA aptamers have been generated to over 100 proteins and small molecules including dopamine (Mannironi et al., 1997 Biochemistry 36, 9726-9734), substance P (Nieuwlandt et al., 1995 biochemisry 34, 5651-5659), human neutrophil elastase (Bless et al., 1997 Current biol. 7, 877-880), Platelet Derived Growth Factor (PDGF) (Green et al, 1996 Biochemisry 35, 14413-14424), Vascular Endothelial Growth Factor (VEGF) (Green et al., 1995 Chem Biol. 2, 683-695), thrombin (Bock et al., 1992 Nature 355, 564-66) and L-selectin (O'Connell et al., 1996 PNAS USA 93, 5883-5887).

The invention therefore provides aptamers capable of binding to OSM (or an OSM receptor) in particular RNA aptamers. Preferred are the aptamers listed in FIG. 16 more particularly Family C aptamers and most particularly aptamer ADR58 in Example 11a.

A number of aptamers have been demonstrated to have biological activity, usually receptor antagonism or enzyme inhibition, both in vitro and in vivo. For example RNA aptamers with high affinity and inhibitory activity to human neutrophil elastase (hNE) were generated by blended SELEX (Bless et al., 1997 supra). Following post-SELEX modification to increase in vivo stability the aptamer was tested in a rat model of lung inflammation (Bless et al., 1997 supra). In a second example, a 49 nucleotide long DNA aptamer was generated to human L-selectin with nM affinity for the protein (O'Connell et al., 1996 supra). The aptamer exhibits 600-fold selectivity for L-selectin over E-selectin and 10 000-fold selectivity over P-selectin. Intravenous injection of a PEG formulation of the aptamer inhibited trafficking of radiolabelled human PBMC to the lymph nodes, but not to other organs, in a dose dependent manner (Hicke et al., 1996 J. Clin. Invest. 98, 2688-2692). In a third example high affinity RNA aptamers have been raised against human VEGF to investigate the role of VEGF in angiogenesis (Jellinek et al., 1994 Biochemistry 33, 10450-10456; Green et al., 1995; Ruckman et al., 1998. J. Biol. Chem 273, 20556-20567; Willis et al., 1998 Bioconjug. Chem. 9, 573-582). A liposomal formulation of the VEGF aptamer inhibits VEGF induced endothelial cell proliferation in vitro and vascular permeability increase and angiogenesis in vivo (Willis et al., 1998 supra). There is therefore provided an oligonucleotide ligand of OSM or an OSM receptor (OSMR, LIFR, gp130) for use in the invention.

To raise an aptamer for use in the invention as described above OSM or a receptor must first be bound to plates for screening. Iterative rounds of selection and amplification (ie the SELEX procedure) can then be performed in accordance with Fitzwater and Polisky (Meths in Enzymol. 267, 275-301) to generate RNA or DNA aptamers to human OSM. Typically these aptamers are modified RNA aptamers as RNA provides the greatest structural diversity and therefore possibility of generating high affinity molecules. Following the generation of a high affinity aptamer a number of post-SELEX optimisation protocols may be performed to increase aptamer stability, to truncate the aptamer to a core sequence (typically aptamers are 100 mers or shorter) that is more amenable to solid phase synthesis thereby reducing the cost of synthesis, and to develop formulations for use in vivo.

In the first of these procedures the aptamer may be truncated to reduce the length of the molecule to a core sequence required for activity. The short core sequence, often between 20 and 40 nucleotides long, will be cheaper and quicker to synthesise and may have increased bioavailability. Information regarding the composition of the core sequence may be obtained from sequence homology comparisons. However, truncation experiments usually involve the synthesis of sequentially shorter aptamers until a minimum sequence required for activity is generated. This usually involves removal of the fixed sequences but there are numerous examples where nucleotides within the fixed sequence have contributed to aptamer affinity (Fitzwater and Polisky, 1996 supra; Ruckman J, et al (1998) J. Biol. Chem. 273, 20556-20567. Green et al., 1995 supra). The invention may therefore provides aptamers which are truncated or extended versions of the selected aptamer or one demonstrating greater than 70% homology in sequence to a selected aptamer.

Following truncation a number of base modification experiments may be performed to improve aptamer stability by protection against ribonuclease cleavage. During SELEX it is not possible to include 2' modified purine bases as the T7 polymerase used for in vitro transcription will not tolerate this modification. Hence to increase aptamer stability post-SELEX it is usual to replace the purine bases within the aptamer with 2' modified purines. This modification is usually through the use of 2'-0-methyl purines although other modified purines including 2'-amino purines or 2'-fluoro purines may be used (Ruckman et al., 1998 supra; Green et al., 1995 supra). This has to be done in a sequential manner as this modification, post-SELEX, may also result in a loss of affinity (Green et al., 1995 supra).

Following truncation and stabilisation it is possible to generate very large amounts of a short fully modified aptamer that may be synthesised by chemical solid scale synthesis. Many molecules can be added to the 5' end of an aptamer to facilitate aptamer use or to formulate an aptamer for in-vivo delivery. This includes a caged moiety to aid imaging (Hnatowich D. J. (1996) Q. J. Nucl. Med. 40, 202-8.), fluorescein to aid molecular detection (German et al., 1998 Anal. Chem. 70, 4540-5.), a lipid group to aid insertion into a liposome (Willis et al., 1998 supra), or conjugation to a small molecule drug or peptide (Charlton J, et al (1997b) Biochemistry 36, 3018-3026). Generally, the addition of a molecule to the 5' end of an aptamer does not result in a loss of affinity or specificity.

To improve in vivo half-life, aptamers have been modified through the addition of polyethylene glycol (PEG) molecules or through the incorporation into liposomes. In both cases such modification can cause a significant increase in in vivo half-life (Willis et al, 1998 supra).

In addition to liposomal formulations aptamers have been formulated with both 20K and 40K PEG to increase serum stability in vivo. A DNA aptamer has been generated against human L-selectin. To increase in vivo stability a 20K PEG ester was coupled to the aptamer through the N-terminal amine moiety. The PEG conjugated aptamer was demonstrated to block L-selectin-dependent lymphocyte trafficking in vivo in SCID mice (Hicke et al., 1996 supra). There is therefore provided for use in the invention, a conjugate of an aptamer and a carrier molecule for example PEG. In this embodiment the aptamer and carrier will be linked for example through the N-terminal amine moiety. In addition there is provided a formulation or composition for use in the invention comprising an aptamer and a delivery molecule for example a liposome. In this embodiment there may be no link between the aptamer and the carrier, the aptamer may simply be encapsulated, dispersed or distributed through the carrier.

The aptamers isolated in this study may also be modified for use as diagnostic molecules to detect the presence of human OSM in serum, tissue or other ex vivo samples, or for the detection of human OSM in whole body in vivo imaging studies (Charlton J, et al (1997) Chemistry and Biology 4, 809-816; Hnatowich, 1996 supra). Fluorescein or other fluorescent detection groups can be added to the 5' end of the aptamer molecule to aid in fluorescence detection for applications such as FACS (Fluorescence Activated Cell Sorting) (Davis K A. Et al (1996) Nuc. Acids Res. 24, 702-6; Charlton et al., 1997 supra), ELONA (Enzyme Linked Oligonucleotide Assays) assays (Drolet D W, et al (1996) Nature Biotech. 14, 1021-1025) and other diagnostic applications. The advent of technetium-99m (Tc99m) chelating peptide cages, such as the MAG3 (Fritzberg A. R., et al J Nucl Med 1986: 27, 111-6) has greatly facilitated the use of a wide range of molecules (Kubo A. et al, (1998) Kaku Igaku 35, 909-28) and macromolecules (Taillefer R. et al, (1995) Eur. J. Nucl. Med. 22, 453-64.), for imaging the presence of the target protein in vivo (macromolecules (Pallela V. R., et al (1999) Nucl. Med. 40, 352-60.). Images are visualised with the aid of a γ-camera and have been achieved in a variety of species from mouse to man. Recent modification of the Tc99m chelators has enabled more efficient and stable labeling of molecules under mild conditions (Hnatowich D. J. 1998 Nucl Med 39, 56-64.).

Methods for radiolabeling single-stranded oligonucleotides have already been developed, the fate of such unmodified labeled oligonucleotides in vivo has been preliminary investigated (Hnatowich, 1996 supra).

It will of course be appreciated that any peptide, protein or nucleic acid based antagonists for use in this invention will preferably be in a purified form ie free from matter associated with such a molecule either in its natural state or as a result of its manufacture, notably the purity is greater than 70% pure but more preferably greater than 80% or 90% pure.

The antagonists of the present invention may be used alone or in combination with immunosuppressive agents such as steroids (prednisone etc.), cyclophosphamide, cyclosporin A or a purine analogue (e.g. methotrexate, 6-mercaptopurine, or the like), or antibodies such as an anti-lymphocyte antibody or more preferably with a tolerance-inducing, anti-autoimmune or anti-inflammatory agent such as a CD4+T cell inhibiting agent e.g. an anti-CD4 antibody (preferably a blocking or non-depleting antibody), an anti-CD8 antibody, an anti-CD23 antibody, a TNF antagonist e.g. an anti-TNF antibody or TNF inhibitor e.g. soluble TNF receptor, or agents such as NSAIDs or other cytokine inhibitors.

Suitable dosages of an antagonist of the present invention will vary, depending upon factors such as the disease or disorder to be treated, the route of administration and the age and weight of the individual to be treated and the nature of the antagonist. Without being bound by any particular dosages, it is believed that for instance for parenteral administration, a daily dosage of from 0.01 to 20 mg/kg of an antibody (or other large molecule) of the present invention (usually present as part of a pharmaceutical composition as indicated above) may be suitable for treating a typical adult. More suitably the dose might be 0.1 to 5 mg/kg, such as 0.1 to 2 mg/kg. A unit dose suitably will be 1-400 mg. Suitable dosages of small organic molecules would be similar and suitable dosages of oligonucleotide ligands would be for example 0.1-10 mg/kg.

The invention further provides a pharmaceutical composition comprising a pharmaceutically acceptable carrier or diluent and, as active ingredient, an antagonist according to the invention and optionally another therapeutic agent as described above. The antagonist, and pharmaceutical compositions thereof of this invention are particularly useful for parenteral administration, i.e., subcutaneously, intramuscularly or intravenously but depending on the nature of the antagonist other routes such as oral, by inhalation, intra-nasal, topical, or intra articular may be more appropriate.

The compositions for parenteral administration will commonly comprise a solution of the antagonist or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. These compositions may be sterilised by conventional, well known sterilisation techniques. The compositions may contain pharmaceutically acceptable auxiliary substances as required to approximate physiological conditions such as pH adjusting and buffering agents, toxicity adjustment agents and the like, for example sodium acetate, sodium chloride, potassium chloride, calcium chloride, sodium lactate, etc. The concentration of antibody or other antagonist in these formulations can vary widely, for example from less than about 0.5%, usually at or at least about 1% to as much as 15 or 20% by weight and will be selected primarily based on fluid volumes, viscosities, etc., in accordance with the particular mode of administration selected.

Thus, a typical pharmaceutical composition for intramuscular injection could be made up to contain 1 ml sterile buffered water, and 50 mg of antagonist. A typical composition for intravenous infusion could be made up to contain 250 ml of sterile Ringer's solution, and 150 mg of antibody or other antagonist according to the invention. Actual methods for preparing parenterally administrable compositions will be known or apparent to those skilled in the art and are described in more detail in, for example, Remington's Pharmaceutical Science, 15th ed., Mack Publishing Company, Easton, Pa. (1980). Suitable formulations for nucleic acid antagonists are discussed above.

The protein antagonists of this invention such as antibodies can be lyophilised for storage and reconstituted in a suitable carrier prior to use. This technique has been shown to be effective with conventional immunoglobulins. Any suitable lyophilisation and reconstitution techniques can be employed. It will be appreciated by those skilled in the art that lyophilization and reconstitution can lead to varying degrees of antibody activity loss (e.g., with conventional immunoglobulins, IgM antibodies tend to have greater activity loss than IgG antibodies) and that use levels may have to be adjusted to compensate.

Single or multiple administrations of the compositions can be carried out with dose levels and pattern being selected by the treating physician. In any event, the pharmaceutical formulations should provide a quantity of the antibody or other antagonist of this invention sufficient to effectively treat the patient.

The present invention includes within its scope an assay for determining whether or not a particular agent which binds to OSM may be useful in the treatment of an inflammatory disease. The invention therefore comprises an assay for the identification of antagonists of OSM comprising combining OSM with the test agent and determining whether or not the agent is capable of blocking the interaction between OSM and the OSM receptor or affecting OSM biological activity through differential expression of a marker molecule.

To select an antagonist for use in the invention as described above OSM, the key binding residues of OSM as described above presented on a carrier or in a manner in which the binding sites are defined ("OSM binding moiety"), or an OSM receptor must first be obtained. cDNA encoding human OSM may be generated synthetically, based on the EMBL sequence (accession number M27288), cloned into an appropriate expression vehicle and used to transform an appropriate host such as E. Coli. Human OSM protein is then purified from culture medium and bound to plates for screening.

OSM, an OSM binding moiety and/or an OSM receptor may be used to assess the binding of small molecule substrates and ligands in, for example, cells, cell-free preparations, chemical libraries, and natural product mixtures. The invention therefore provides an assay for the identification of an antagonist of OSM which comprises contacting OSM with a test agent and measuring for binding. These substrates and ligands may be natural substrates and ligands may be structural or functional mimetics. Such molecules are included in the definition of antagonists of OSM. The method of screening may involve high-throughput. For example, to screen for antagonists, a synthetic reaction mix, cellular compartment, such as a membrane, cell envelope or cell wall, or a preparation of any thereof, may be prepared from a cell that expresses OSM receptor. The preparation is then incubated with labelled OSM in the absence or the presence of a candidate molecule. The ability of the candidate molecule to bind to OSM receptor is reflected in decreased binding of the labelled OSM. Molecules which bind gratuitously, ie, without inducing the functional effects of OSM are likely to be good antagonists. This assay may be reversed and labelled OSM receptor may be used with unlabelled OSM. A further screen with an ELISA format may be used to identify OSM antagonists where the ability of a candidate molecule to prevent binding of an OSM receptor conjugate such as gp130-Fc fusion protein to plate-immobilised OSM is measured, in this assay bound gp130-Fc is detected by enzyme-labelled anti-Fc antibody and colourimetric assay.

The functional effects of potential antagonists may be measured, for instance, by determining activity of a reporter system following interaction of the candidate molecule with a cell or appropriate cell preparation, and comparing the effect with that of OSM or molecules that elicit the same effects on OSM. Reporter systems that may be useful in this regard include but are not limited to colorimetric labelled substrate converted into product, a reporter gene that is responsive to changes in the functional activity of OSM receptor, and binding assays known in the art.

FIGURES

FIG. 1a: ELISA showing ex-vivo secretion of Oncostatin M by synovial biopsy cultures.

Figure 1B:
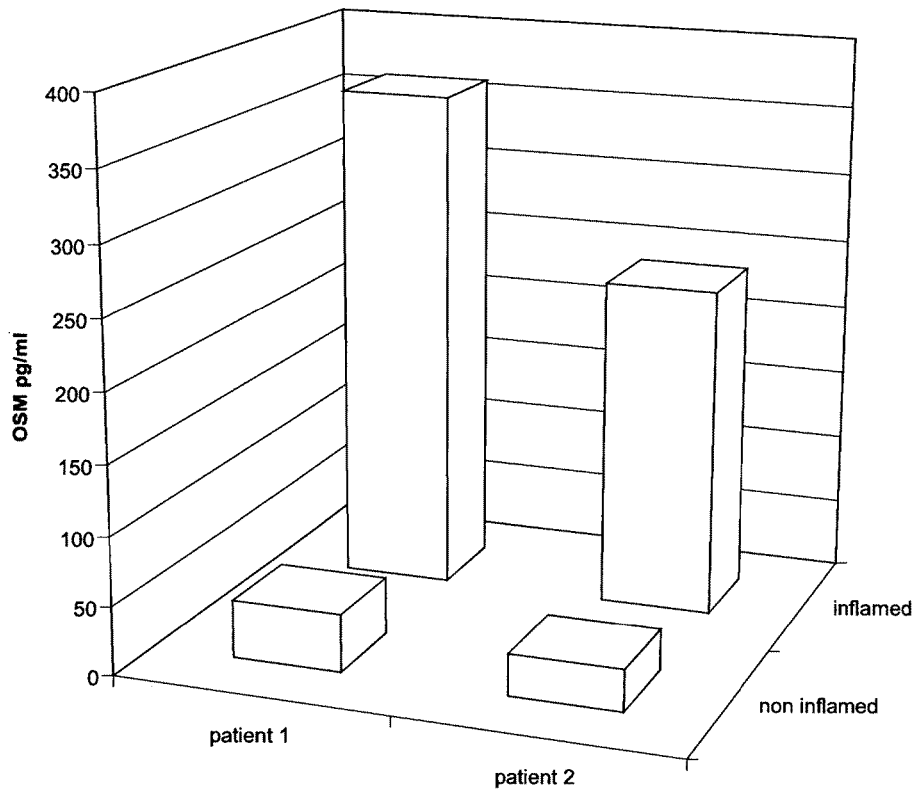

FIG. 1b: Spontaneous ex-vivo secretion of Oncostatin M by inflamed but not non-inflamed synovial cultures.

Figure 2:
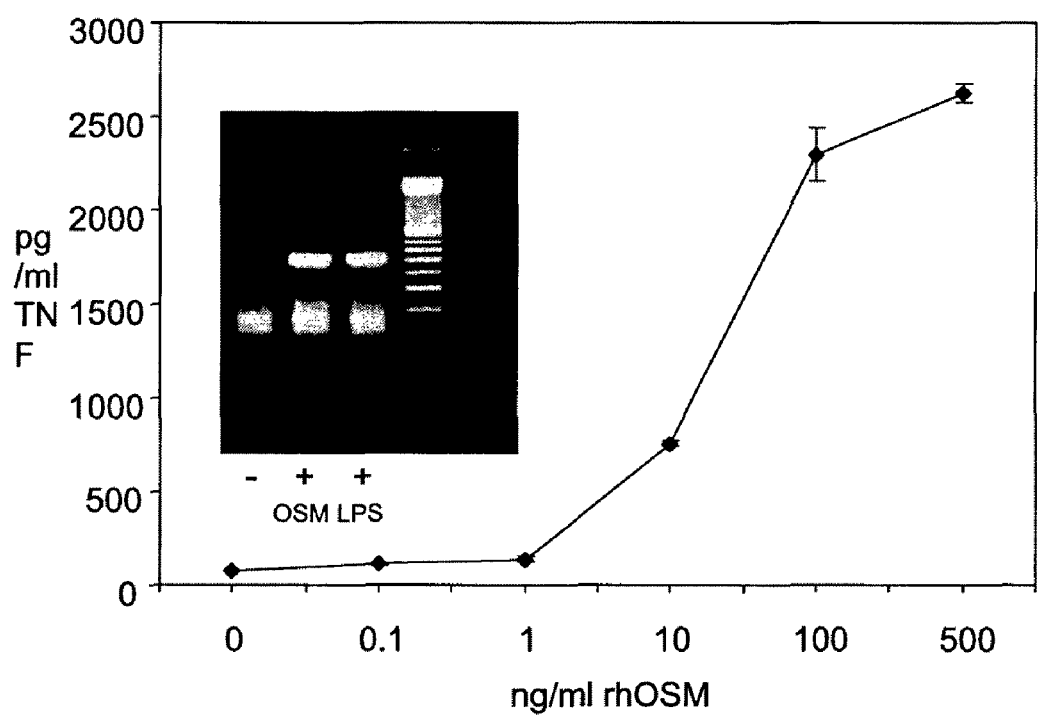

FIG. 2: Effect of rhOSM on TNF alpha production by PMA differentiated THP-1 cells.

FIG. 3 a&b Synergistic effect of OSM with TNFα to promote collagen release ex-vivo.

Figure 4A:
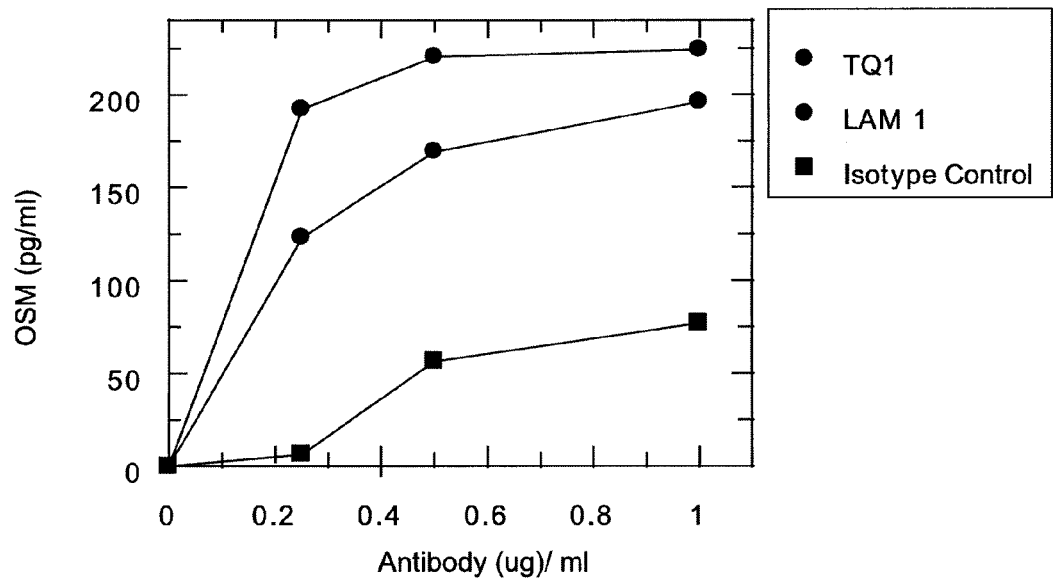

FIG. 4a Anti-L-selection antibody mediated secretion of OSM.

Figure 4B:
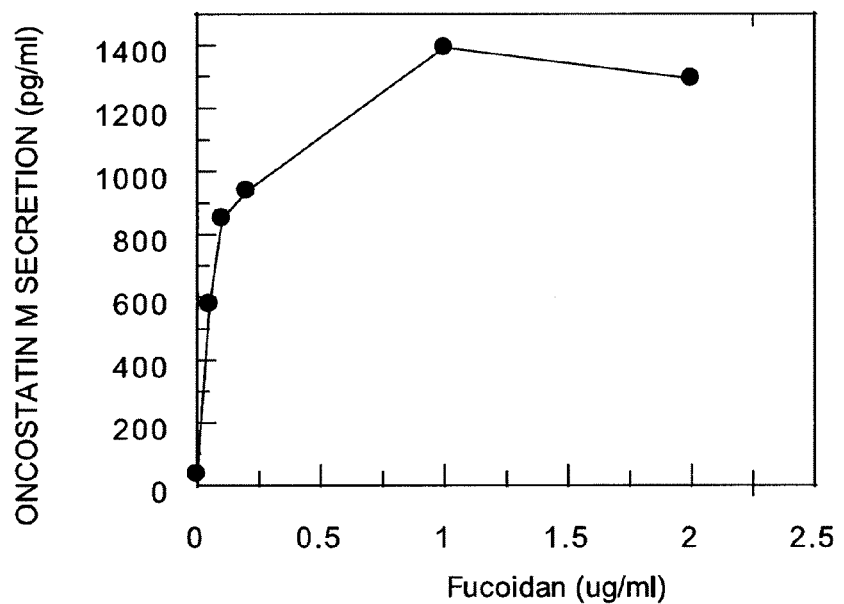

FIG. 4b Fucoidan induced OSM secretion.

FIG. 5a-d Photomicrograph demonstrating the staining of RA vascular endothelial using gp130 P and E-selection antibodies.

Figure 6:
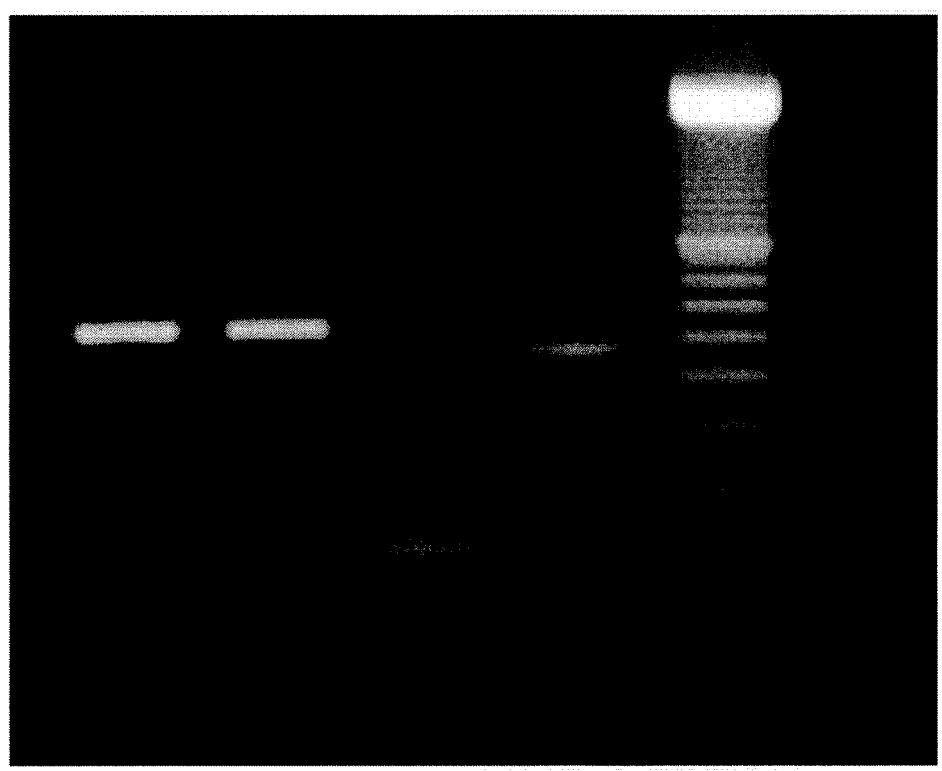

FIG. 6 OSM RNA message in joints from control & CII-arthritic mice.

FIG. 7 Arthritic DBA-1 mice treated with goat anti-OSM antibody or control goat IgG. 7a=Clinical scores. 7b=Paw thickness FIG. 8 Histological data comparing joint infiltration and cartilage damage in collagen-arthritic mice.

8a & b: Control mice exhibited extensive joint infiltration by PMNs and mononuclear cells (8a) and surface destruction of articular cartilage, characterised by widespread neutrophil infiltration (8b).

8c & 8d: Representative joints of an anti-OSM treated animal with normal/mild arthritis, demonstrating a markedly reduced level of cellular infiltrate with intact articular cartilage.

Figure 9B:
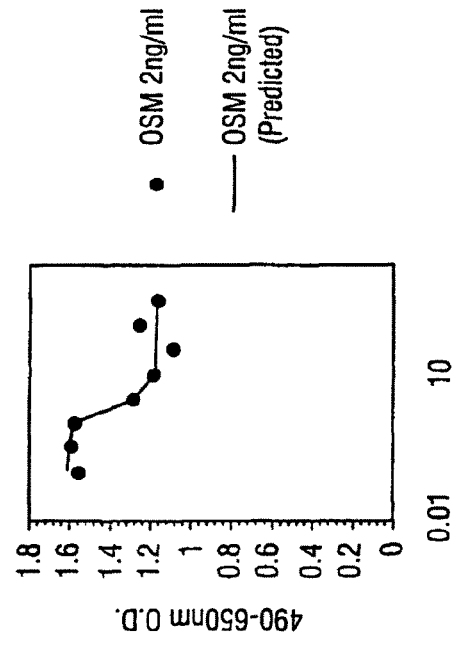
Figure 9A:
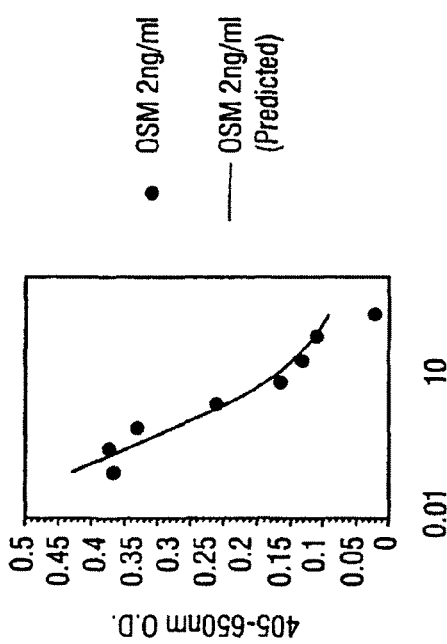

FIG. 9 HepG2 B6 sPAP and MTS assay for N-(1H-pyrazolo[3,4-d]pyrimidin-4-yl)benzamide showing a concentration-dependent inhibition of OSM-induced sPAP release.

FIG. 10 TNFα sPAP and MTS assay for N-(1H-pyrazolo[3,4-d]pyrimidin-4-yl)benzamide showing limited inhibition of TNFα-induced sPAP release from A549 cells.

Figure 11A:
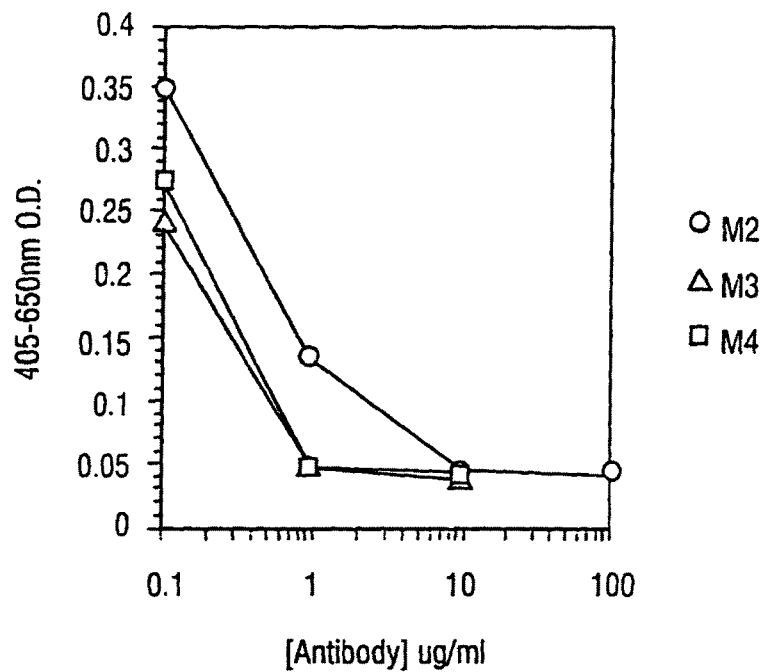
Figure 11B:
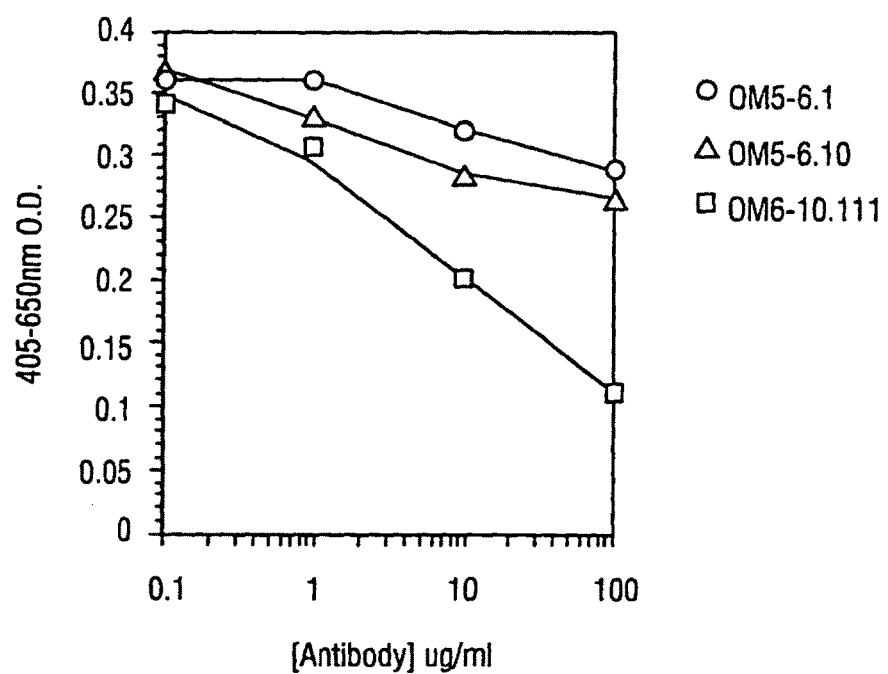

FIG. 11 Antibody inhibition of sPAP production in the HepG2 B6 assay. M2-M4 denote mouse sera from four individual mice; OM5-6.1, OM5-6.10, OM6-10.111 denote experimentally derived hybridoma supernatant.

Figures 12A, 12B:
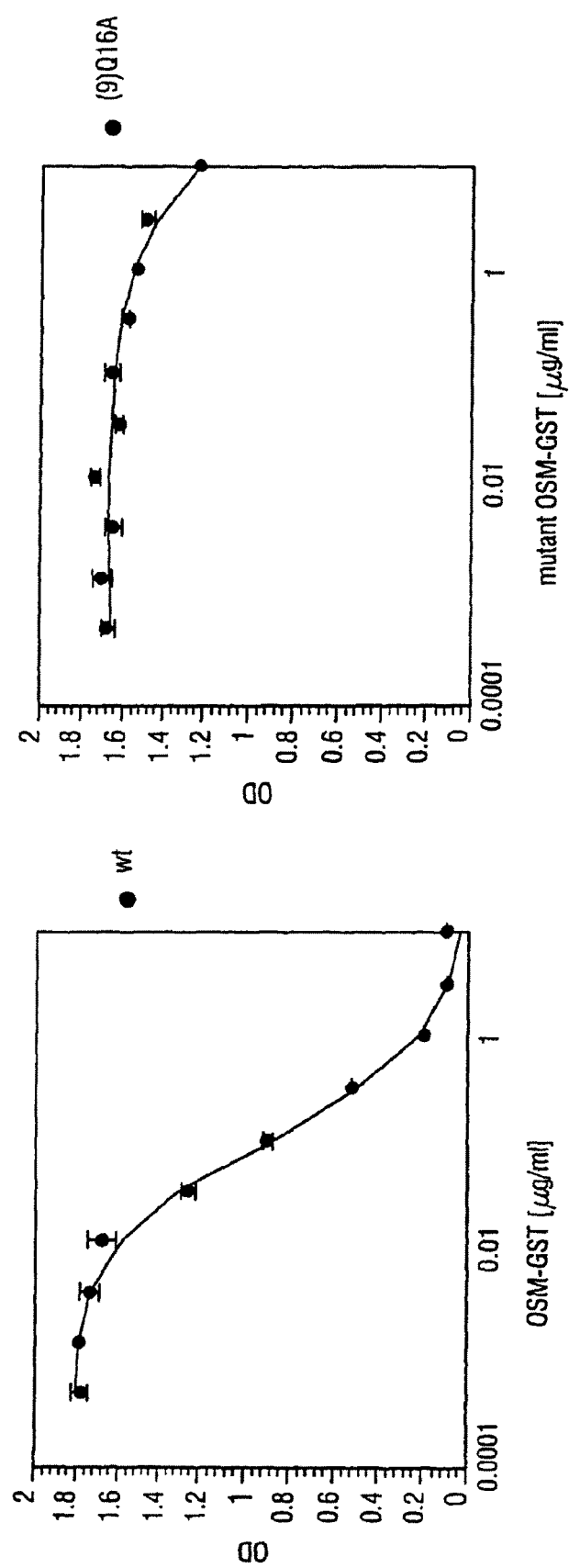
Figures 12C, 12D:
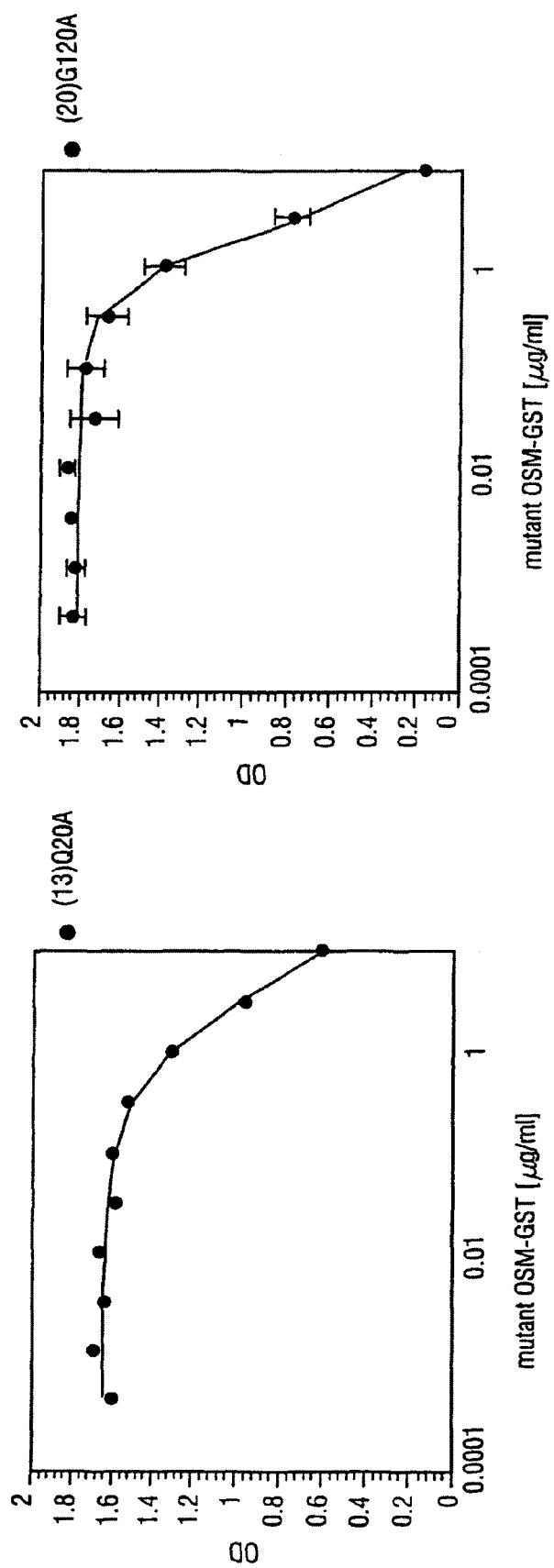
Figure 13A:
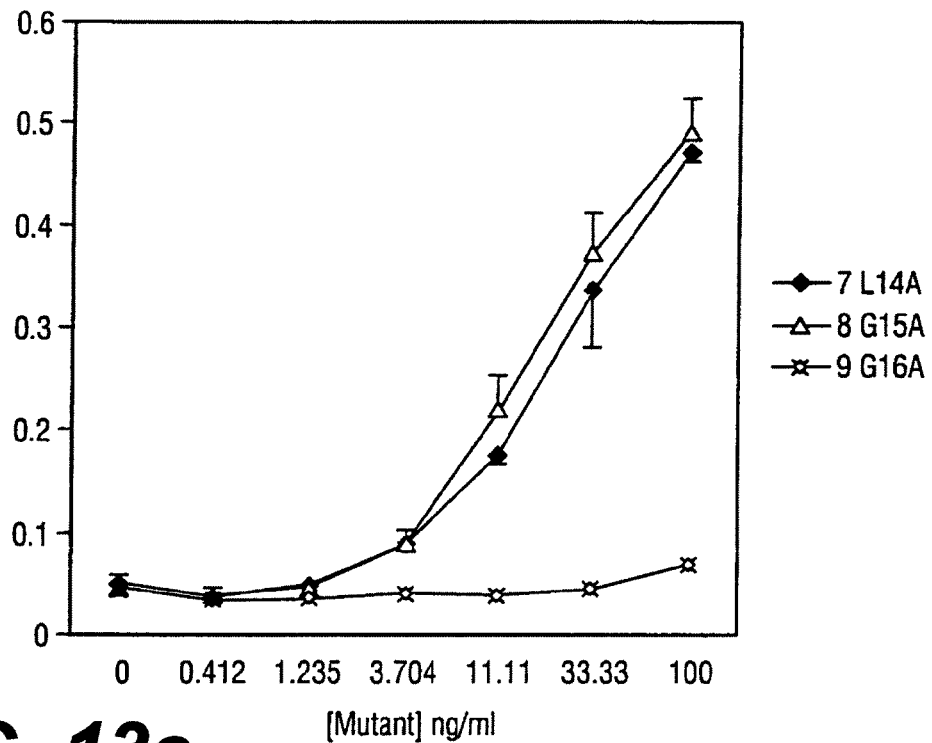
Figure 13B:
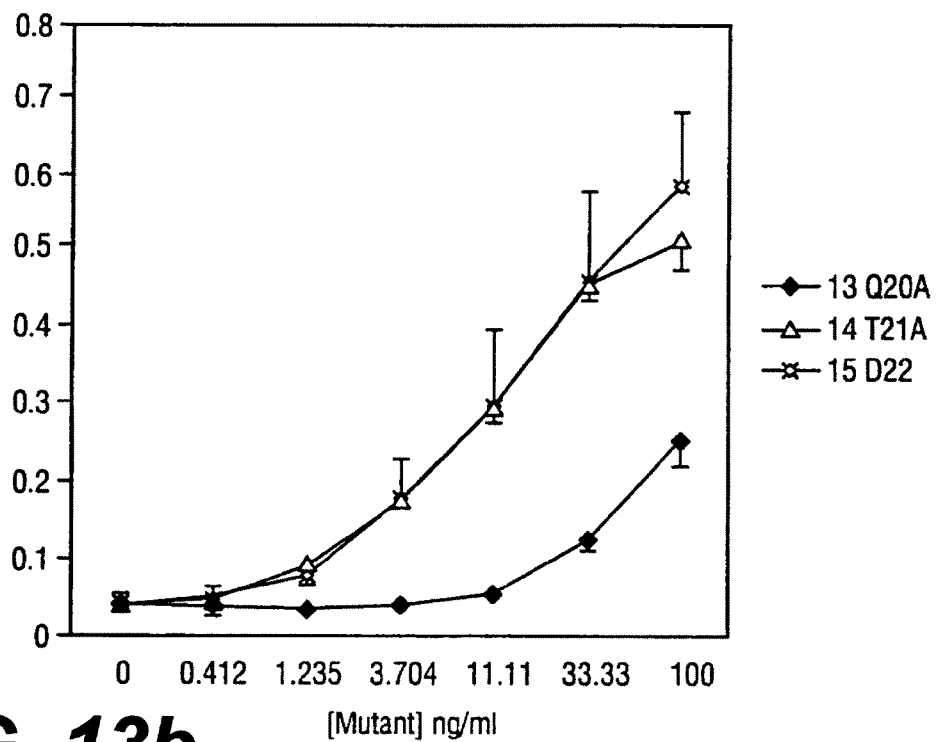
Figure 13C:
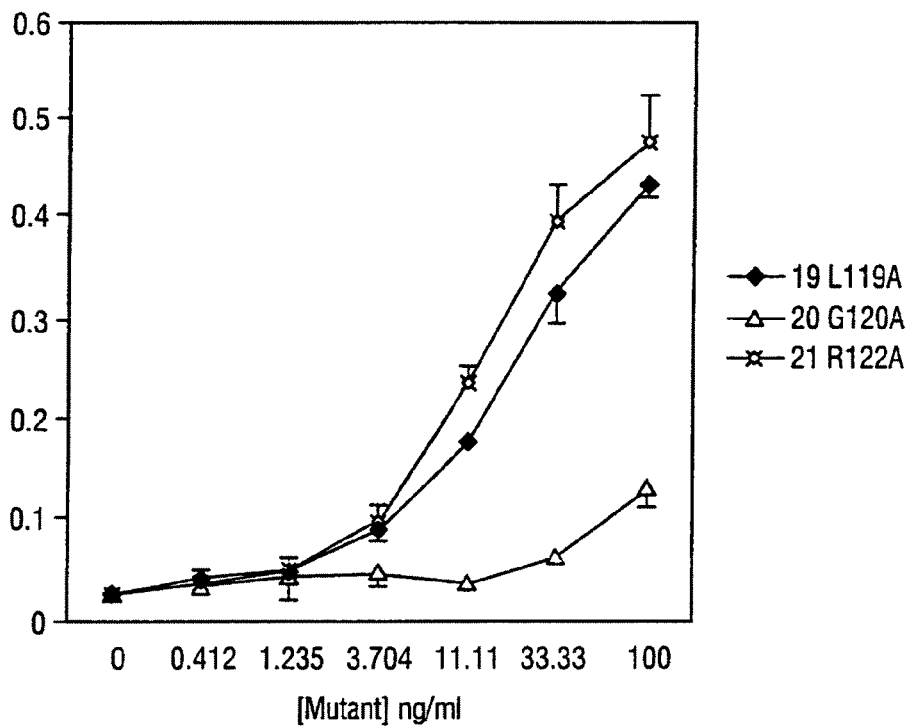
Figure 13D:
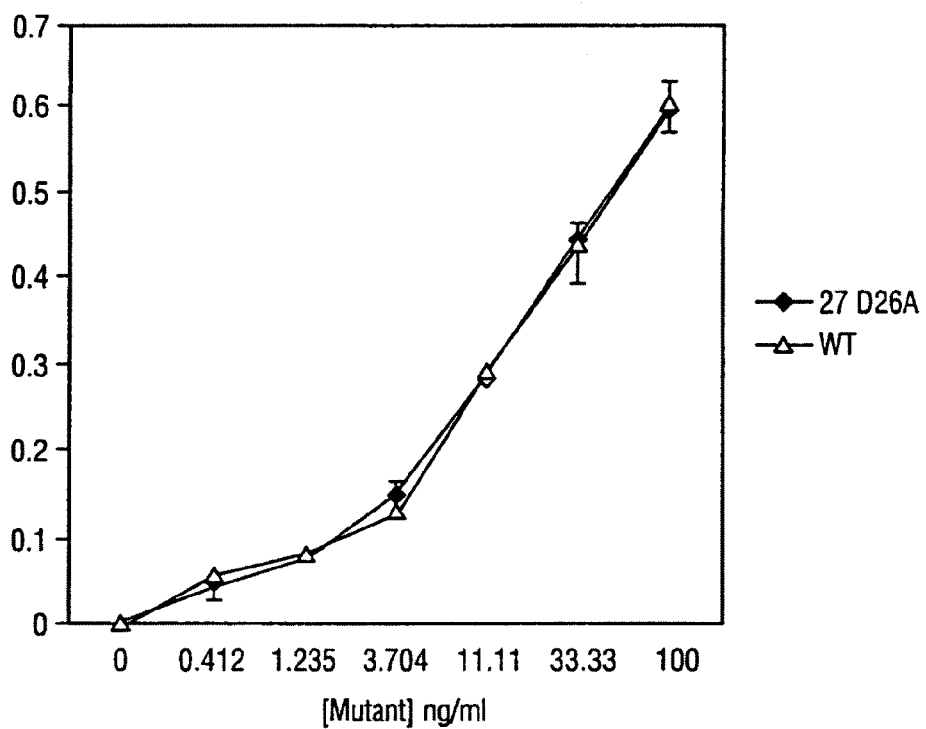

FIG. 12 Competition of wild type and mutant OSM-GST fusion with plate-bound wild type OSM for binding to gp130-Fc in an Elisa.

FIG. 13 O.D. plots of three mutant OSM-GSTs showing least activity in driving sPAP production in the HepG2 cells.

Figure 14:
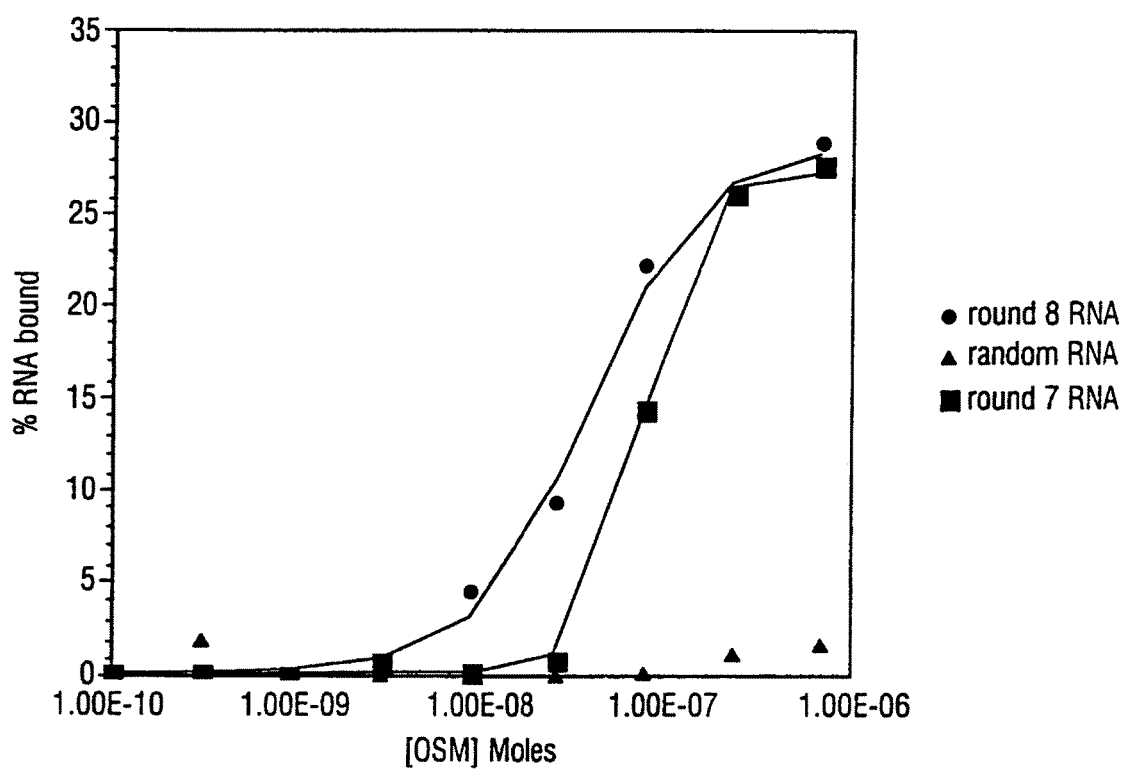

FIG. 14 Affinity of the RNA aptamer pool for human OSM determined after 7 and 8 rounds of Selex. The equilibrium dissociation constant (Kd) of the round seven pool was 72 nM and the round 8 pool 37 nM. The starting pool showed no affinity for human OSM at any concentration tested.

Figure 15:
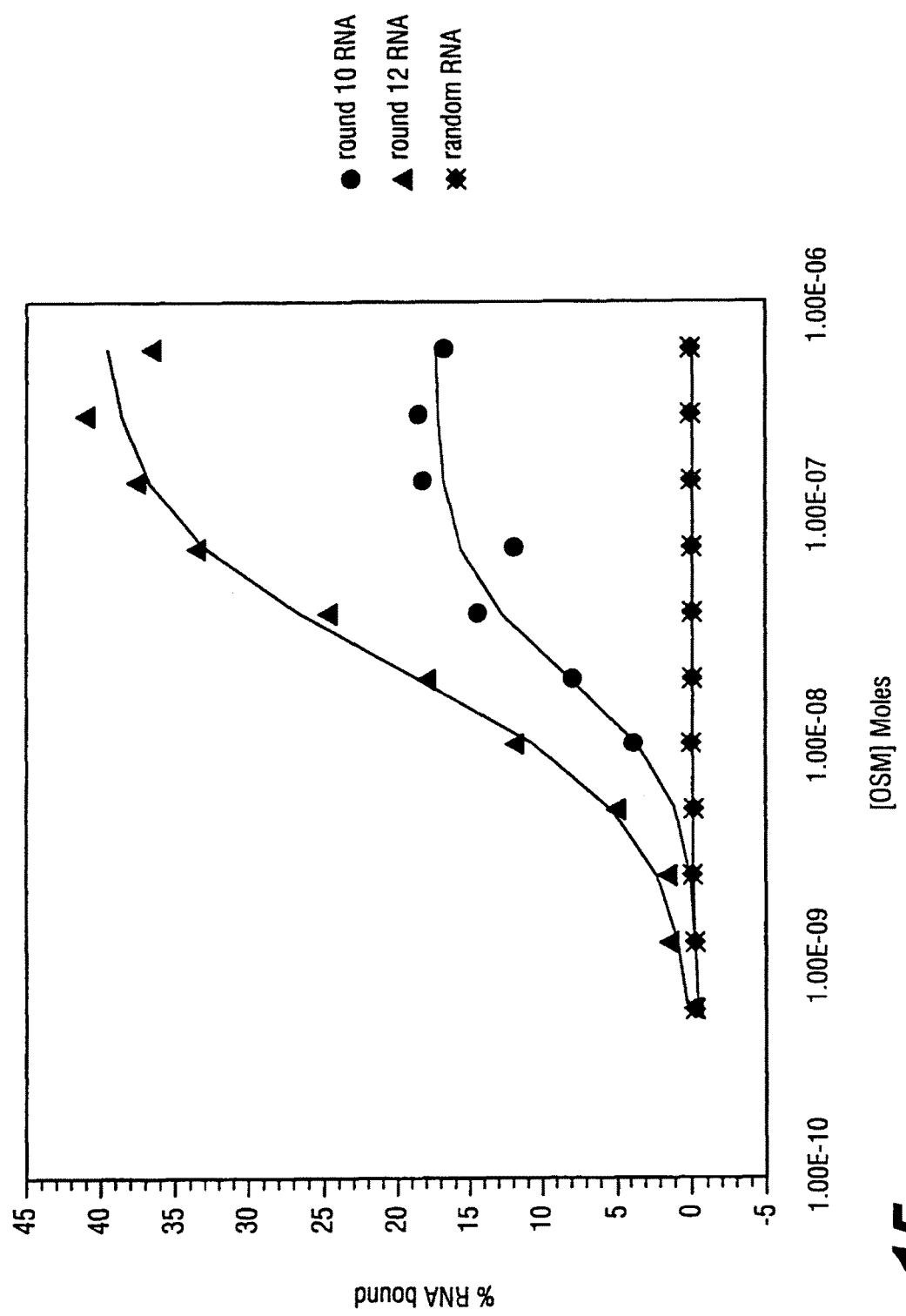

FIG. 15 Affinity of the RNA aptamer pool for human OSM determined after 10 and 12 rounds of Selex. The equilibrium dissociation constant (Kd) of the round 10 pool was 22 nM and the round 12 pool 20 nM. The starting pool showed no affinity for human OSM at any concentration tested.

FIG. 16 Sequence alignments of 59 individual aptamer clones using PileUp software. The 5' fixed, 40N random and 3' fixed sequences of the aptamers are annotated, N denotes any of A, C, G or T.

Figure 17:
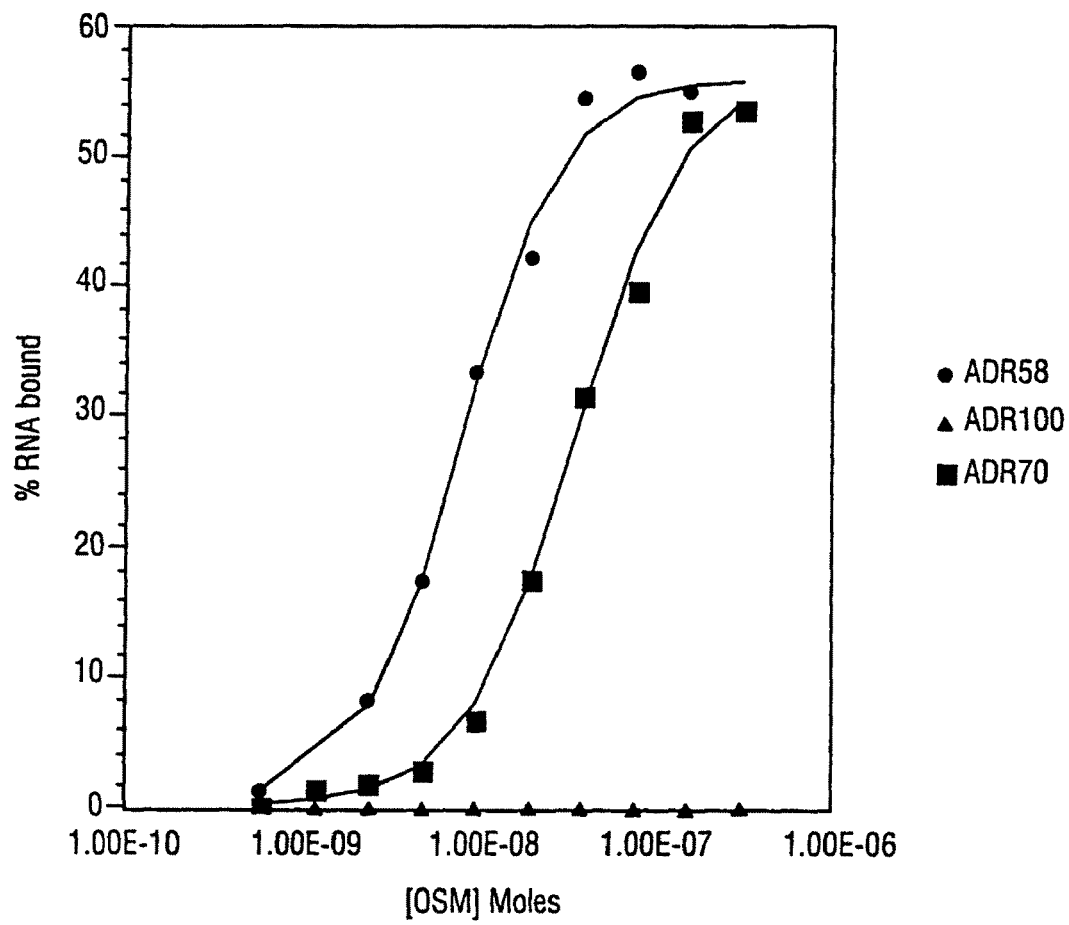
Figure 18A:
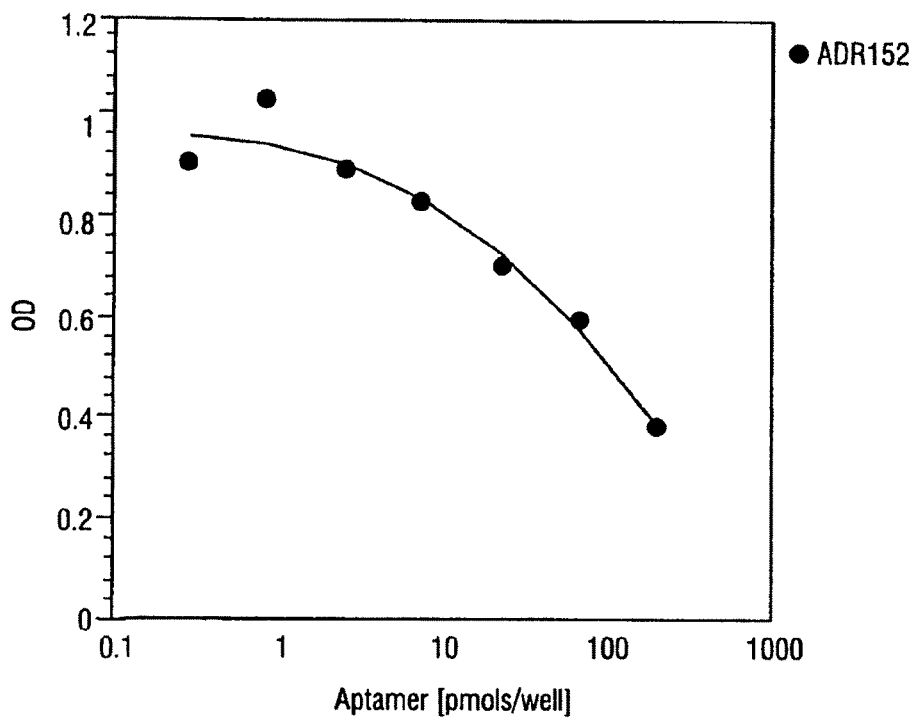
Figure 18B:
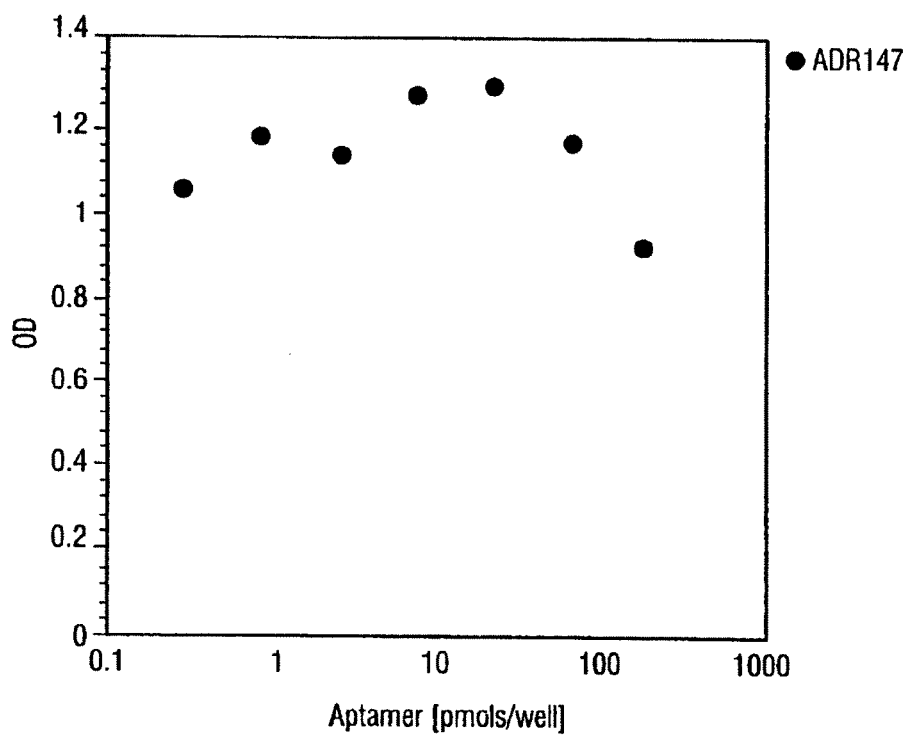
Figure 18C:
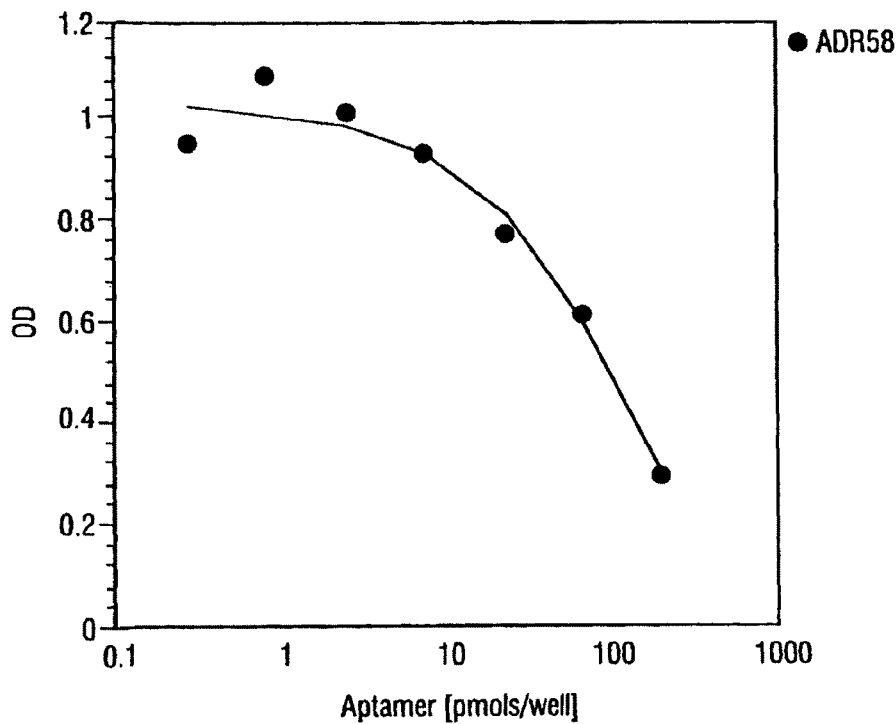
Figure 18D:
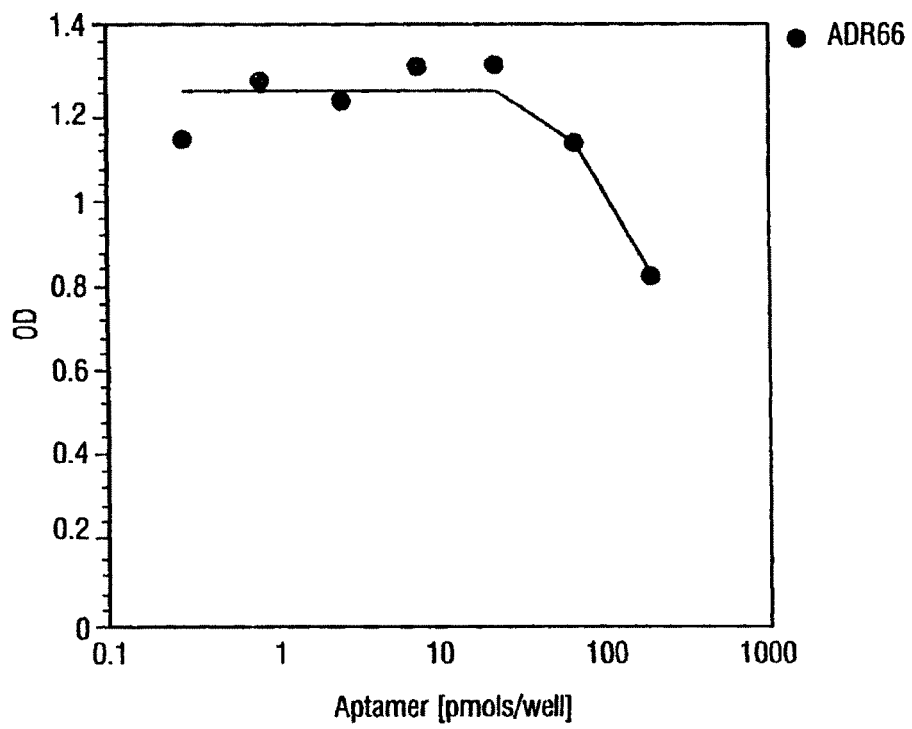
Figure 18E:
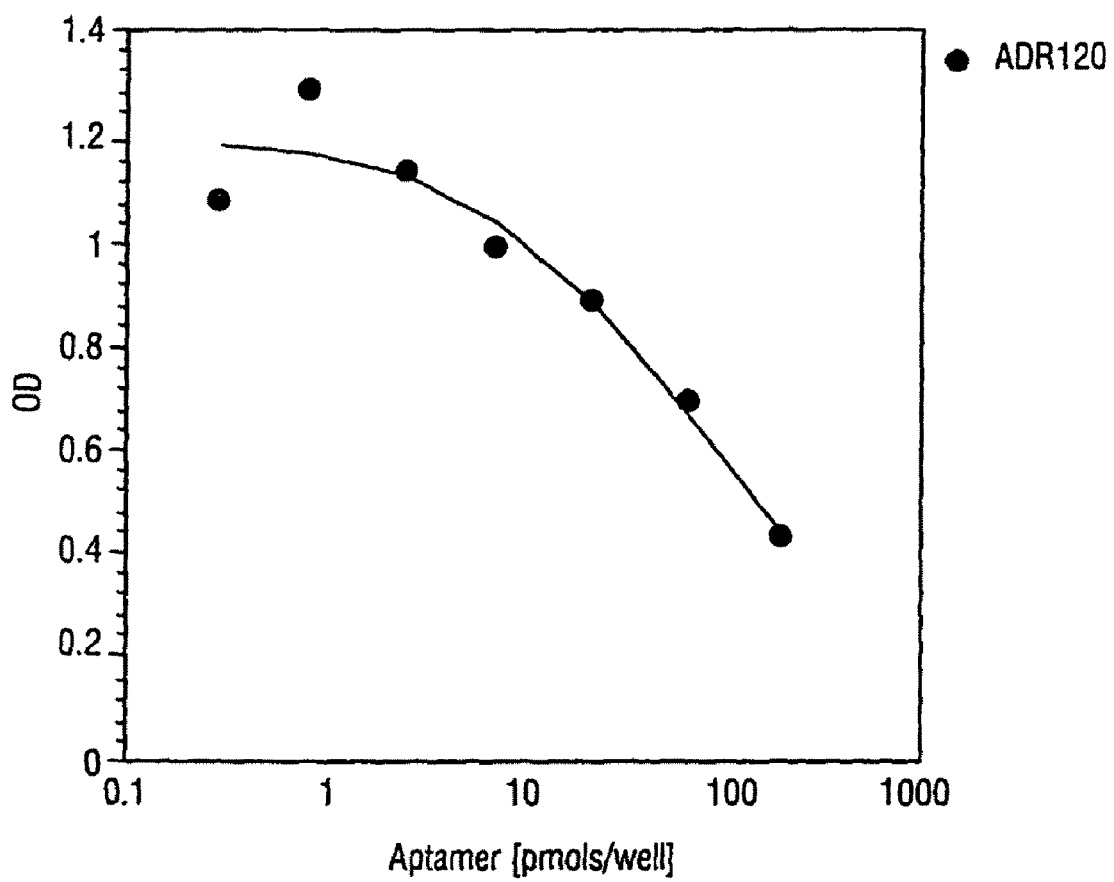

FIG. 17 Representative binding curves of aptamers ADR58, ADR100 and ADR70 for OSM. The equilibrium dissociation constant (Kd) of ADR58 was 7 nM, ADR70 was >1 uM and ADR100 was 35 nM.

FIG. 18 Ability of OSM aptamers ADR 58, ADR152, and ADR120 with high binding affinity for human OSM, to block binding of hOSM to the gp130 receptor.

FIG. 19 Specificity of ADR58 (A1) and a random pool of RNA (A2) to inhibit ADR58 binding to gp130 in the gp130/OSM ELISA assay. (B) To confirm that ADR58 was specifically binding to human OSM to prevent an interaction with the gp130 receptor a control ELISA was performed in which OSM was omitted. Neither ADR58 (B1) or a random pool of RNA (B2) showed any activity in this assay. (C) To examine the specificity of ADR 58 a TNF/TNFR1 Elisa was performed. The ability of ADR58 (C1) or a random pool of RNA (C2) to inhibit the binding of the cytokine TNFα to the TNFR1 receptor was thus investigated. Neither aptamer ADR58 or the random pool of RNA shows activity in this assay.

Figure 20:
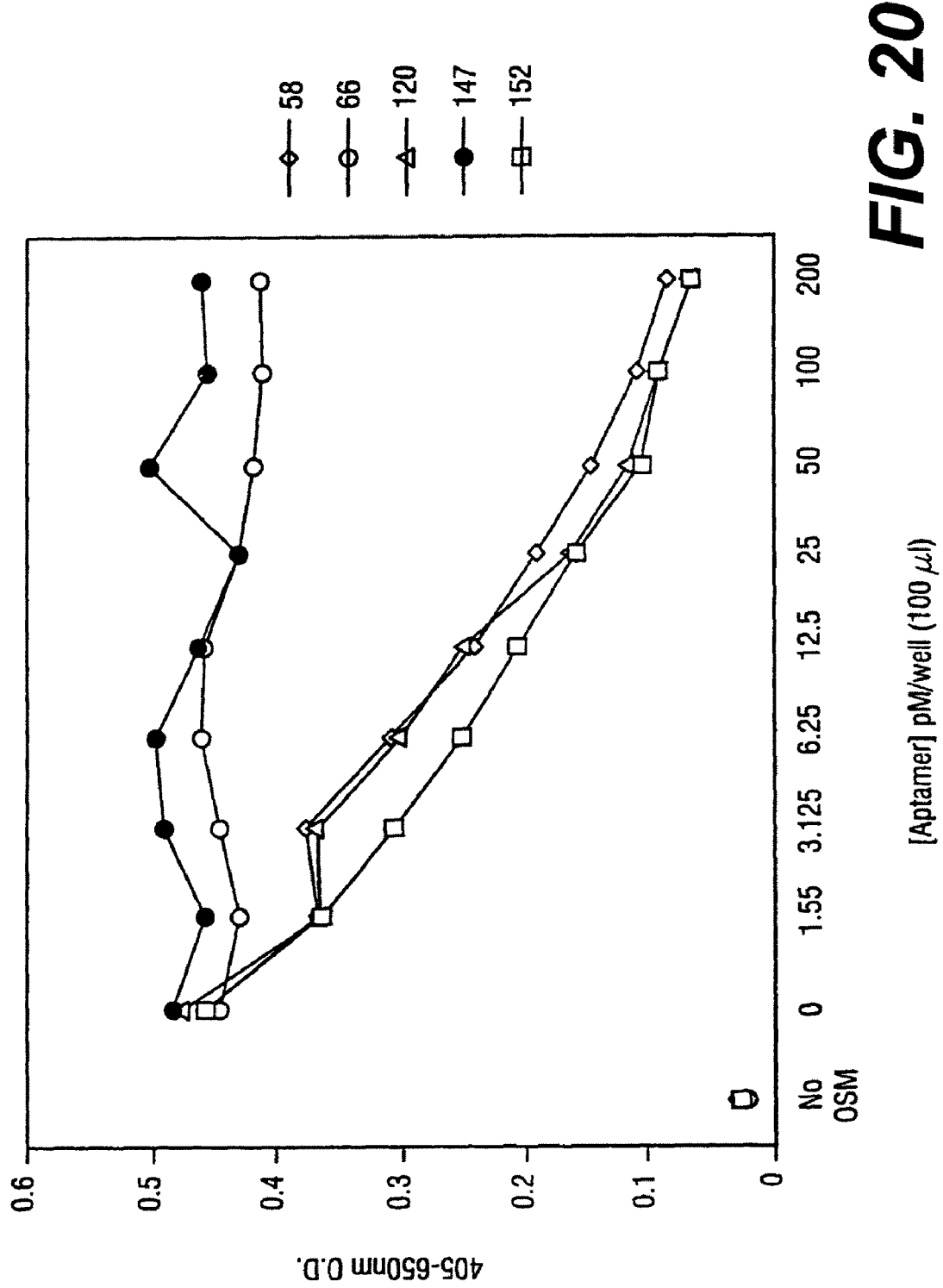

FIG. 20 Ability of AFR58, ADR152 and ADR120 with high binding affinity for human OSM to block OSM activation of a STAT-sPAP reporter gene. The low affinity aptamer ADR66 and the non-specific aptamer ADR147 were included as controls.

Figure 21:
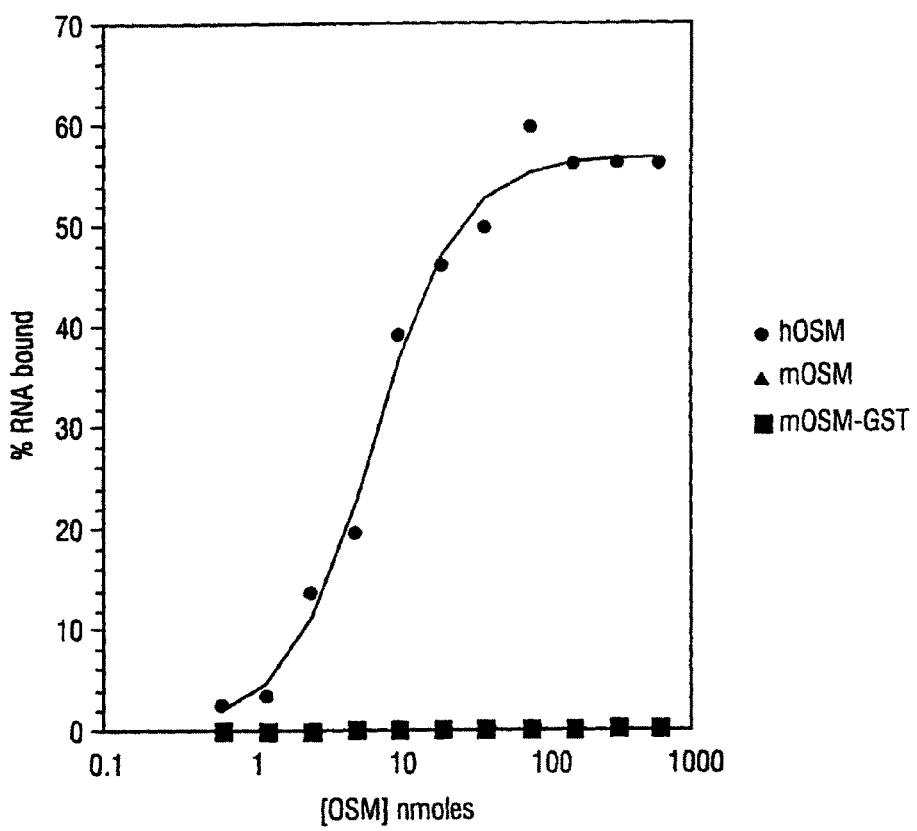

FIG. 21 The affinity of the aptamer ADR58 for human and mouse OSM. The equilibrium dissociation constant (Kd) of ADR 58 for human OSM was 7 nM. ADR58 showed no binding affinity for either murine OSM or GST-OSM fusion protein.

Figure 22:
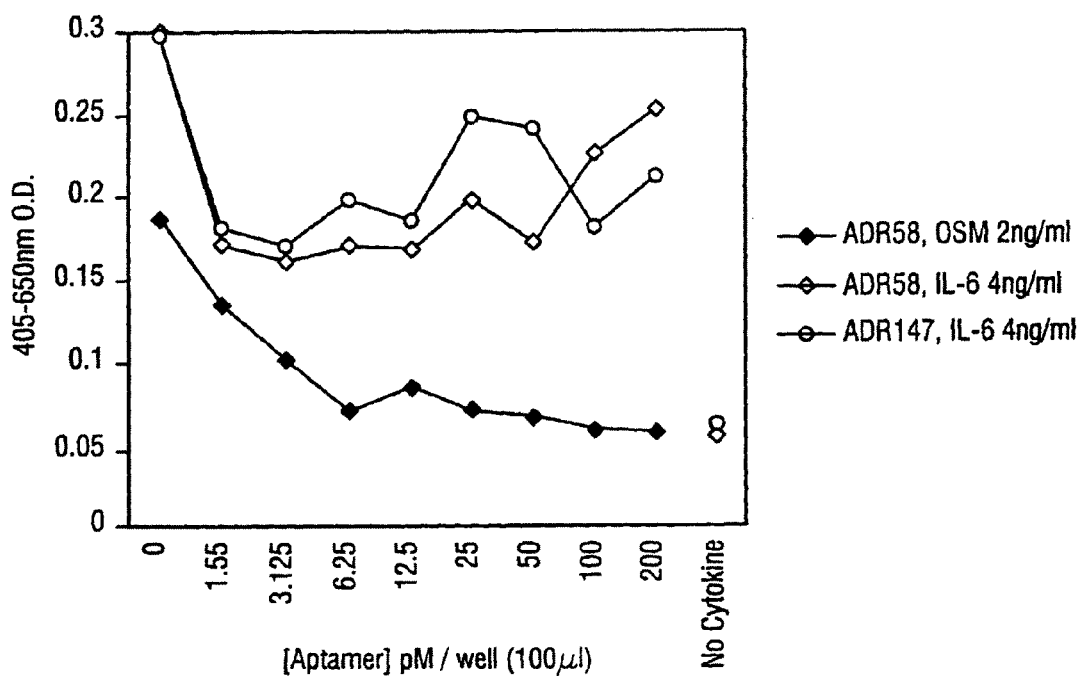

FIG. 22 Ability of Aptamer ADR58 to prevent IL6 mediated activity of STAT-sPAP reporter gene contained within these cells. ADR58 effectively inhibits OSM activation of the STAT-sPAP reporter gene. Neither aptamer ADR58, or the non-specific aptamer ADR147 are able to block IL-6 activation of the reporter gene.

The present invention will now be described by way of example only with reference to the accompanying drawings; wherein:

EXAMPLE 1

Detection of OSM in Ex-Vivo Synovial Tissue Cultures

Experiment 1

Freshly excised synovial tissue from patients diagnosed as having rheumatoid arthritis, osteoarthritis or bunions was mechanically dissected using sterile hypodermic needles to produce approximately 1 mm³ fragments. These were placed in flat-bottomed 200 µl wells on a 96 well tissue culture plate (Costar) to which was added RPMI 1640 (Sigma) supplemented with 10% heat-inactivated AB⁺ male serum (North London Blood Transfusion Centre), 10 mM hepes, 1% sodium pyruvate, 1% non-essential amino acids (all from Sigma), 4 mM L-glutamine (Hyclone), 100 U/ml penicillin+ 100 µg/ml streptomycin (Hyclone) (complete human medium, CHM) and incubated at 37° C.

100 ul/well samples of culture supernatant were collected on days 0, 2, 5 and 9 frozen at 20° C. and then tested for OSM by ELISA. (Quantikine R&D Systems) Data are shown in FIG. 1a. Secreted OSM was detected in RA-derived synovial samples, but not from synovium derived from OA or non-arthritic control patients. OSM levels in the RA tissue cultures were maximal around day 5 of incubation, reaching a concentration of approximately 1400 pg/ml and remained greater than 800 pg/ml at day 9.

Experiment 2

Synovial tissue was washed in PBS and fatty tissue removed. Sterile scissors were used to cut the tissue into small (1-4 mm) fragments. This tissue was washed in PBS before use. The tissue was weighed and directly plated out in a 24 or 48 well plate (Costar), 100 mg/well. The tissue was cultured at 37° C. and 5% $CO_2$ in 1.5 ml Dulbecco's modified Eagle's medium (Sigma) supplemented with 10% heat-inactivated AB+ human serum (Sigma), 2 mM L-glutamine (Life Technologies), 200 U/ml penicillin and 200 µg/ml streptomycin (Life Technologies), 480 U/ml nystatin (Sigma), 50 µg/ml gentamycin (Life Technologies) and 10 mM Hepes (Sigma), filter-sterilised. At day 3 supernatants were removed and tested for OSM in an ELISA using paired antibodies (R&D Systems).

Synovial tissue cultures from knee biopsy of patients with RA or inflamed OA spontaneously secrete OSM. Following the 3 day incubation period, the mean level of OSM in the culture supernatant from the RA cultures was 246 pg/ml (range 30 to 982, n=12) and from OA cultures was 473 pg/ml (range 44 to 2001, n=14). OSM is secreted by inflamed but not quiescent synovial tissue (FIG. 1b).

EXAMPLE 2a

Differentiation of THP-1 Cells

Human pro-monocytic line THP-1 cells (ECACC) were passaged twice weekly in RPMI supplemented with 10% heat-inactivated FCS, 10 mM hepes, 1% non-essential amino acids (all from Sigma), 4 mM L-glutamine (Hyclone), 100 U/ml penicillin+100 µg/ml streptomycin (Hyclone) (complete medium, CM) and then PMA (Sigma) was added to washed cells at 1 µg/ml and Incubated at 37° C. for 30 minutes. Cells were washed ×3 in pre-warmed PBS, resuspended in CM and plated out at $1.5 \times 10^5$ cells/ml in 96-well flat bottomed plates (Costar). Plates were incubated for 48 hours at 37° C., 5% $CO_2$, then washed with PBS, the media replaced, and incubated for a further 24 hours. Cells were washed ×1 in PBS before use.

EXAMPLE 2b

Preparation of IFN Gamma-Stimulated Blood Monocytes

Human buffy coats (North London Blood Transfusion Centre) were diluted 1:3 with PBS, layered onto Lymphoprep (Nycomed UK) and centrifuged at 600×g for 30 minutes at room temperature. Harvested PBMC were washed 3 times in PBS, counted, and resuspended in 80 mls RPMI 1640/10% FCS at $5 \times 10^6$ cells/ml. 20 mls were put into each of four 175 cm² flasks and Incubated overnight at 37° C. to allow monocytes to adhere. Non-adherent cells were discarded and adherent cells scraped off after incubation with ice-cold versene at 4° C. for 15 minutes. Cells were washed twice in PBS, resuspended in RPMI 1640+10% heat inactivated human serum (Sigma) at $6.9 \times 10^5$/ml and 250 ul cell suspension placed into each well of 96-well flat bottomed plate (Costar). To half the plate was added 100 IU/ml IFN γ (Genzyme), the other half left as control. Plates were incubated overnight at 37° C., 5% $CO_2$ prior to assay.

EXAMPLE 2c

Stimulation of TNFα Release

Lyophilised, recombinant human oncostatin M (rhOSM) was purchased from R&D Systems diluted to 10 μg/ml in sterile PBS+0.1% BSA (Sigma) and aliquots stored at −20° C. until use. rhOSM, *E. coli*-derived LPS or CM were added to triplicate wells of macrophages, monocytes or Thp-1 cells, prepared as above and incubated for 7 hours at 37° C., 5% $CO_2$. Supernatants were harvested and frozen at −20° C. until testing for TNFα protein by ELISA. In assays designed to co-assay for TNFα mRNA, cells were incubated as above for 4 hrs, washed once in PBS and lysed in RNA extraction buffer (RNAzole).

RNA was detected as follows. Total RNA was prepared according to the manufacturer's instructions and stored at −80° C. in DEPC-treated water. For RT-PCR, approximately 1 ug of RNA was reverse transcribed using oligo dT priming (first strand cDNA synthesis kit, Pharmacia Biotech) and the resulting cDNA subjected to 30 cycles of PCR using the following primers for TNFα (Clontech amplimers): forward-GAGTGACAAGCCTGTAGCCCATGTTGTAGCA, (SEQ ID 1) reverse-GCAATGATCCCAAAGTAGACCTGCCCA-GAC (SEQ ID 2). The amplified product (444 bp) was separated by agarose gel (2%) electrophoresis and visualized by ethidium bromide staining.

EXAMPLE 2d

OSM Induces TNFα Production in Human Cells of the Monocyte Lineage

The human pro-monocytic line THP-1, was induced to differentiate using PMA, washed thoroughly, and incubated with recombinant human OSM as described above. Culture supernatants were removed at 8 hours and assayed for TNFα production by specific ELISA (TNF Quantikine, R&D Systems) in accordance with manufacturers instructions. OSM induced a dose-related release of TNFα, measurable above 1 ng/ml OSM and maximal at 200-500 ng/ml, routinely reaching secreted levels of greater than 2500 pg/ml TNFα. A representative experiment is shown in FIG. 2. Expression of TNFα message, measured by RT-PCR as described above was strongly increased in THP-1 cells incubated for 4 hr with 100 ng/ml OSM, relative to unstimulated control cells (FIG. 2).

Importantly, TNFα induction was not due to contaminating endotoxin as pre-boiling of OSM completely ablated TNFα secretion (data not shown). Also, removal of OSM by immunoprecipitation using specific antibody abolished activity (data not shown). These findings were extended to include human blood monocytes, pre-activated with interferon-γ and human blood macrophages, differentiated in culture for 7 days. Both cell types, when co-incubated for 8 hr with OSM, secreted TNFα, as measured by ELISA. Mean TNFα secretion by monocytes was 1447 pg/ml (range 137-4709 pg/ml; n=4 donors) and 542 pg/ml by macrophages (range 62-1428 pg/ml; n=3 donors).

EXAMPLE 3a

Cartilage Degradation Assay

Bovine nasal septum cartilage was held at 4° C. overnight after slaughter. 2 mm diameter discs were cut from 2 mm slices and washed twice in HBSS. Three discs per well of a 24 well plate (Costar) were incubated at 37° C., 5% $CO_2$ for 24 hrs in a 600 μl volume of DMEM (Sigma) containing 25 mM HEPES supplemented with 2 mM glutamine, 100 μg/ml streptomycin, 100 U/ml penicillin and 2.5 μg/ml amphotericin B (cartilage degradation medium, CDM). Cartilage was cultured in quadruplicate wells in either: 600 μl of CDM alone, 2, 10 or 50 ng/ml human recombinant TNFα alone, 10 ng/ml rhOSM alone (R&D systems) or TNFα+OSM and incubated for 7 days at 37° C., 5% $CO_2$. Supernatants were harvested and replaced with fresh medium containing identical test reagents to day 1. The experiment was continued for a further 7 days and on day 14 all medium was removed and the remaining cartilage digested with 4.5 mg/ml papain (Sigma) in 0.1M phosphate buffer pH 6.5, containing 5 mM EDTA and 5 mM cysteine hydrochloride, incubating at 65° C. for 16 hrs, to determine the remaining hydroxyproline content of the cartilage fragments. The cumulative level of OH-proline released into the medium by day 14 was measured and expressed as the percentage of total released as set out below.

EXAMPLE 3b

Hydroxyproline Assay

Hydroxyproline release was assayed (as a measure of collagen degradation) using a microtitre plate modification of the method in (Bergmann I and loxley R. (1963) Anal. Biochem. 35 1961-1965. Chloramine T (7%) w/v) was diluted 1:4 in acetate citrate buffer (57 g sodium acetate, 37.5 g tri-sodium citrate, 5.5 g citrate acid, 385 ml propan-2-ol per liter water). P-dimethylaminobenzaldehyde (DAB; 20 g in 30 ml 60% perchloric acid) was diluted 1:3 in propan-2-ol. Specimens were hydrolysed in 6M HCL for 20 h at 105° C. and the hydrolysate neutralised by drying over NaOH in vacuo using a Savant SpeedVac. The residue was dissolved in water and 40 ul sample or standard (hydroxyproline; 5-30 ug/ml) added to microtitre plates together with Chloramine-T reagent and then DAB reagent (150 ul) after 4 minutes. The plate was heated to 65° C. for 35 min, cooled and the absorbance at 560 nm determined.

EXAMPLE 3c

Figure 3A:
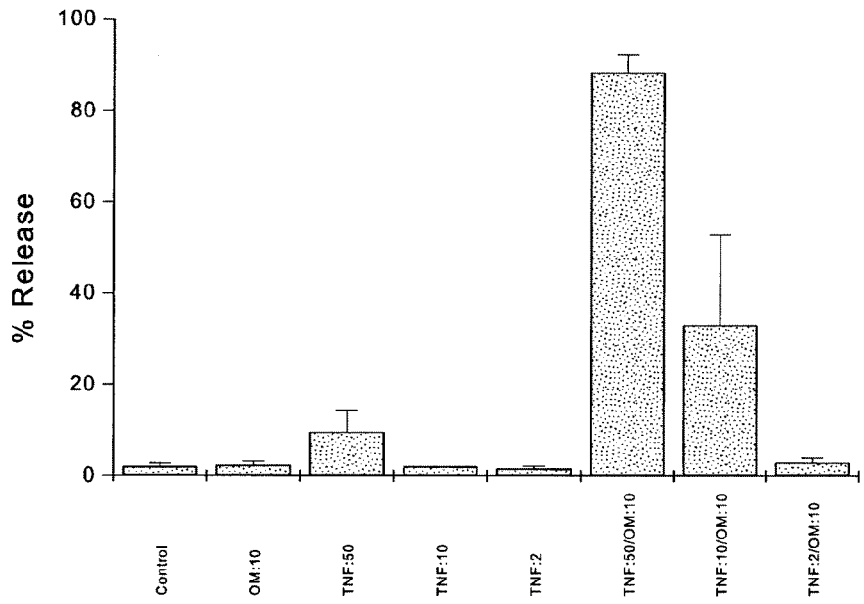
Figure 3B:
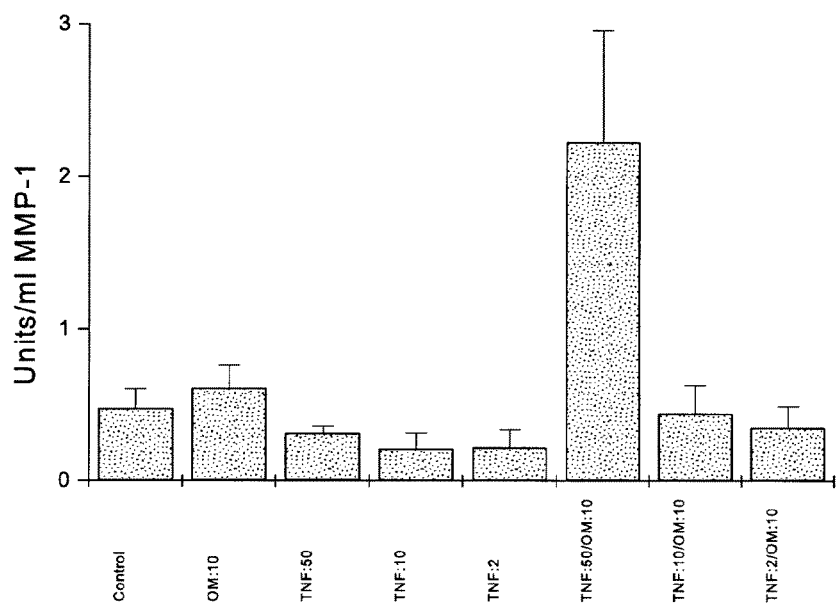

OSM Synergises with TNFα to Increase MMP1 and Collagen Release from Cartilage Explants, Ex-Vivo Bovine nasal cartilage was cultured in quadruplicate wells for 14 days in the presence or absence of OSM or TNFα alone (both from R&D Systems), or in combination, as described above. Culture supernatants were assayed for total collagenase activity on day 7 and for released collagen on day 14. Data in FIG. 3*b* demonstrate that neither OSM nor TNFα alone, used at 10 ng/ml or 50 ng/ml, respectively, induced significant MMP1 secretion. However, the combination of OSM and TNFα used at these concentrations did induce measurable MMP1 release. These findings were accompanied by a striking synergy between OSM and TNFα to increase collagen release from cartilage. FIG. 3a shows that OSM alone at 10 ng/ml did not induce collagen release, whereas only the highest concentration of TNFα used (50 ng/ml) had a small, but demonstrable effect (less than 10%). However, the combination of 10 ng/ml OSM with either 50 or 10 ng/ml of TNFα resulted in greater than 80% and 30% collagen release, respectively.

EXAMPLE 4a

Stimulation of PBMC Via L-Selectin

Mononuclear cells were isolated from human buffy coats as described above. $5 \times 10^5$ cells were plated out in 0.5 ml volumes and incubated for 24 hr at 37° C., 5% $CO_2$ with 60-80 kD M. wt. fucoidan (Sigma) anti-L-selectin monoclonal antibodies, LAM1-3 and TQ1 or an isotype matched control IgG antibody (all from Coulter). Supernatants were assayed for OSM using a specific ELISA assay (Quantikine, R&D Systems), according to the Manufacturer's instructions.

EXAMPLE 4b

Ligation of L-Selectin Induces OSM Secretion

Mononuclear cells from healthy donors were incubated for 24 hrs with anti-human L-selectin antibodies, (either TQ1 or LAM-1), or an isotype-matched control antibody and culture supernatants assayed by ELISA for OSM. Data in FIG. 4a show a dose-dependent induction of OSM using both anti-L-selectin antibodies. Control antibody had a minimal effect. The ability of the L-selectin agonist fucoidan to induce OSM from mononuclear cell cultures was then investigated. FIG. 4b shows that fucoidan was a powerful stimulant of OSM secretion, inducing levels similar to those seen in RA and OA synovial biopsy cultures (Example 1, Experiment 2 FIG. 1b).

EXAMPLE 5a

Immunohistochemistry

Fresh human tissue samples were frozen in $CO_2$-cooled liquid hexane and stored in the vapour phase of liquid $N_2$ until use. 7 mm cryostat sections were cut onto 3-Aminopropyltriethoxysilane (APES) (Maddox P. et al J. Clin Path. 40; 1256-1260, 1987) coated glass slides and fixed for 10 minutes at 4° C. in 2% paraformaldehyde. Endogenous peroxidase activity was blocked for 20 minutes in 0.05% $H_2O_2$. Unconjugated, primary monoclonal antibodies were obtained from the following sources: CD62P, CLB, Netherlands; CD62E and gp130 R&D Systems UK. Primary antibodies were applied at optimal dilution for 45 minutes at room temperature. Negative control sections were incubated with an anti-BrdU monoclonal antibody (SIGMA) used at protein concentrations equivalent to test antibodies. A biotinylated secondary antibody, followed by peroxidase labelled ABC (Vector Elite) was used to label the primary antibody. Peroxidase was developed with a DAB (3,3' Diaminobenzidine) substrate (SIGMA).

EXAMPLE 5b

Co-Distribution of Selectins and OSM Receptors in RA Synovium

The frozen sections of inflamed RA synovial tissue were stained using specific antibodies to gp130, and P and E selectin as described above. Photomicrograph (a) in FIG. 5 demonstrates that RA vascular endothelium stained strongly positive for gp130.

Staining of RA synovium for P- and E-selectin expression revealed an identical staining pattern to gp130, restricted to vascular endothelial cells. (FIG. 5 b and c respectively). Note in FIG. 5c the perivascular mononuclear cell infiltrate associated with E-selectin staining. Staining of serial sections using control primary antibodies was negative on vascular endothelial cells (FIG. 5 panels c and d).

EXAMPLE 6a

Anti-OSM Antibody Treatment of Collagen-Induced Arthritis

Collagen induced arthritis was induced in male DBA/1 mice (8-12 weeks old) by immunisation with native bovine type II collagen (CII) as previously described (Plater-zyberk C. Clin. Exp. Immunol 98:442-7 1994 and Plater-zyberk C. Nature Medicine 1: 781-5, 1995). From day 16 post-CII immunisation, mice were monitored daily for signs of joint redness and swelling. From the first appearance of clinical symptoms, mice were examined three times per week and each limb was graded for disease severity using the following visual scores: 0=normal. 0.5=arthritis in 2 or more digits, 1=slight swelling and erythema of paw without digit involvement, 1.5=same as 1 with involvement of digits, 2=more pronounced swelling with erythema of paw without digit involvement. 2.5=same as 2 with digit involvement, 3=severe swelling with impairment of movement, 3.5=same as 3 with digit involvement. Paw thickness was measured using calipers (Proctest 2T, Kroeplin Langenmesstechnik).

CII-immunised DBA/1 mice were treated after clinical onset of disease by i.p. injections of 100 mg goat anti-mouse OSM antibody (R and D Systems, cat. no. AF-495-NA). Disease progression was assessed as described above. On day 14 post-onset, mice were sacrificed by cervical dislocation and paws collected for histopathological examination.

EXAMPLE 6b

Histological Assessment of Arthritic Mouse Joints

Legs were skinned and knees and paws dissected away. Joints were fixed in 10% buffered formalin for 4 days (knees) or 1 day (paws) and decalcified for 3 days in 25% formic acid, dehydrated and embedded in paraffin wax. Sagittal sections (5-7 mm) of the joints were de-waxed and stained with Safranin O, fast green/iron hematoxylin counterstain (as described in Plater-zyberk Nature Medicine above). Synovitis was graded blindly from 0 (no infiltration) to 3 (extensive infiltration and synovial hyperplasia). The degree of loss of Safranin O staining intensity indicative of cartilage proteoglycan depletion, was scored on a scale from 0 (fully stained cartilage) to 3 (complete depletion and loss of cartilage).

EXAMPLE 6c

Detection of OSM mRNA in Joint Tissues of Collagen Arthritic Mice

Arthritic mice, plus untreated control animals, were sacrificed and both paws and feet removed and snap frozen in liquid nitrogen followed by storage at −80° C. RNA was prepared by grinding each limb in RNAzole using an ultraturrax mechanical homogenizer. Particulate material was allowed to settle, and the supernatant then mixed with 1/10th volume of chloroform and spun to separate the aqueous phase containing RNA. RNA was precipitated using RNAmate (BioChain Institute Inc, San Leandro, Calif.) to remove contaminating proteoglycans. After washing in 75% ethanol, total RNA was dissolved in DEPC-water and reverse transcribed using the Pharmacia first strand cDNA kit and oligo dT priming. PCR reactions were performed using the following primers (Life Technologies custom primers) derived from the mouse OSM sequence (Yoshimura A. et al EMBO Journal 15 1055-1063, 1996): GGGTGTCCTACCAAGGAACA (SEQ ID 3), CTGAGACCTTTCAAGAGGAC SEQ ID 4). After 30 cycles of PCR, reaction products (379 bp) were detected using agarose gel electrophoresis. RT-PCR was used to detect OSM mRNA in arthritic mouse paws as described above. FIG. 6 shows that levels of OSM-specific PCR product were increased in joints taken from animals with progressively increasing clinical disease scores. By contrast, little or no OSM message was detected in control animals.

EXAMPLE 6d

Neutralisation of OSM Ameliorates Collagen-Induced Arthritis

To directly test the hypothesis that neutralisation might improve clinical symptoms of arthritis, two 100 μg injections of neutralising polyclonal antibody to OSM were administered i.p on days 1 and 3 after the first appearance of clinical arthritis in a group of 6 mice. In parallel, a second group of 6 arthritic mice were treated identically, using non-immune goat IgG instead of anti-OSM. Mice were scored for clinical severity of arthritis, and individual paw swelling measured for a follow-up period of 11 days after the second antibody injection. Mice treated with control goat IgG developed a progressive arthritis, accompanied by an increase in paw swelling.

In marked contrast, mice treated with anti-OSM antibody developed a significantly less severe arthritis in terms of clinical score and paw swelling (FIG. 7 a and b). Also, the number of arthritic paws was significantly reduced in anti-OSM treated compared to control IgG-treated animals, demonstrating that this therapeutic protocol was effective at protecting animals with already established disease from further disease progression. (Data not shown). This experiment was repeated in identical fashion, using 7 mice per group and produced closely matching data (data not shown).

Figure 8A:
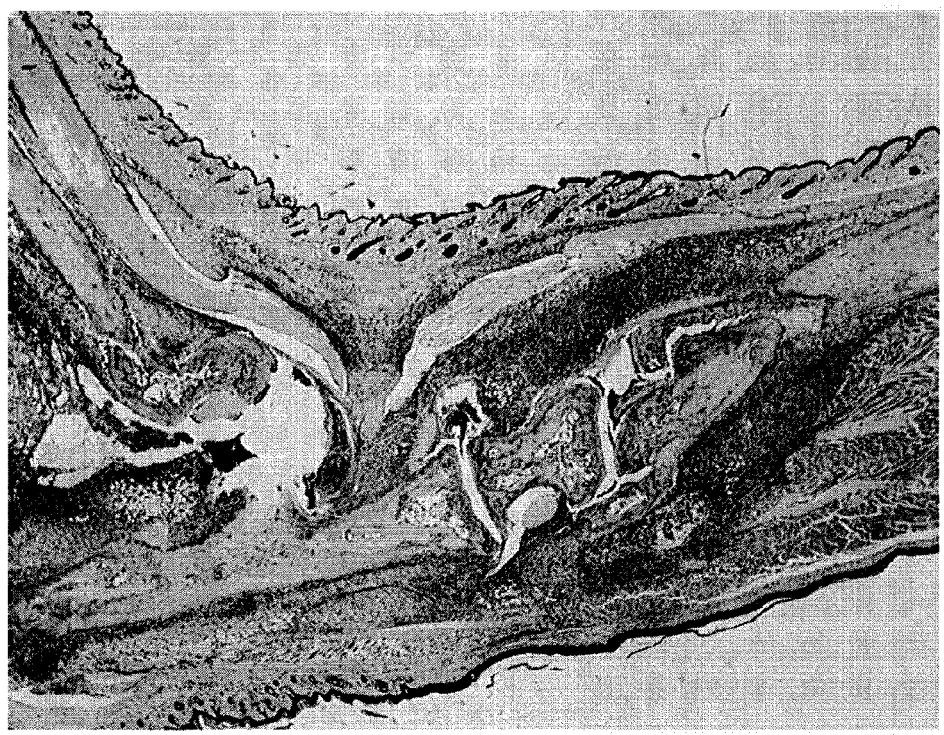
Figure 8B:
Figure 8C:
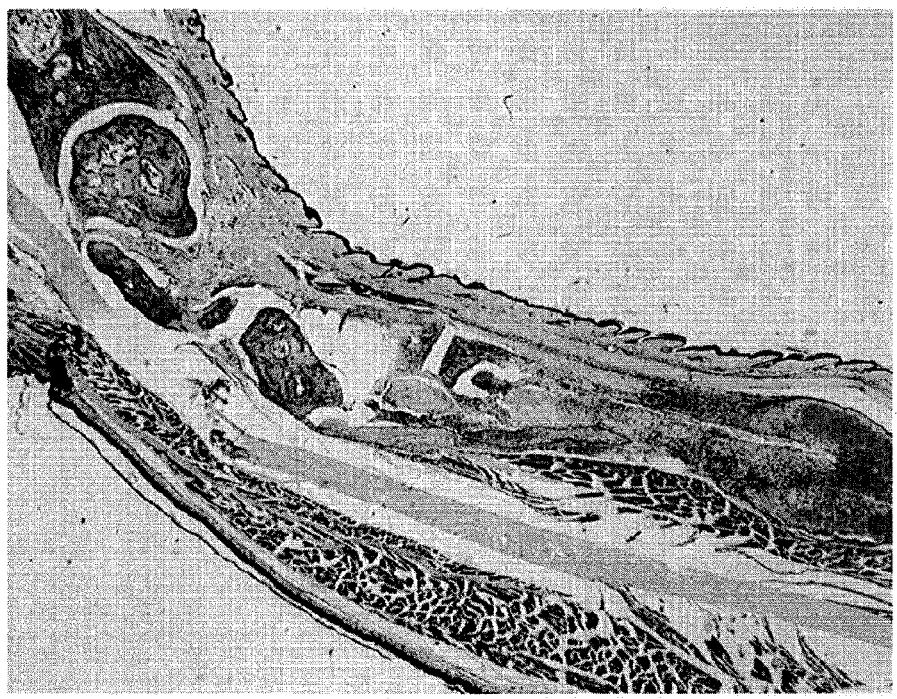
Figure 8D:
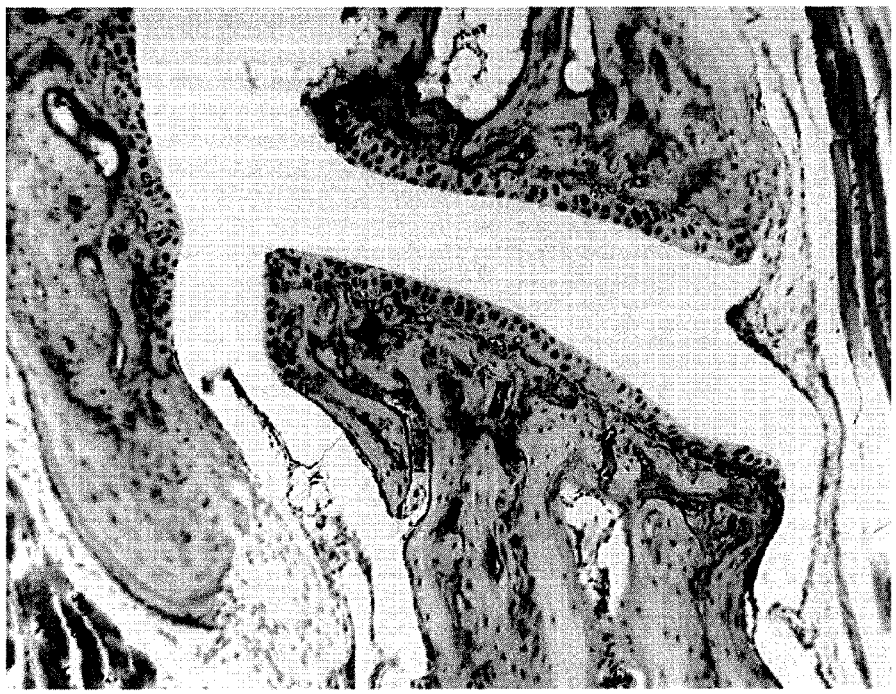

The reduction in clinical severity resulting from treatment with anti-OSM antibody was confirmed by post-mortem histological examination of arthritic paws at day 14 post-disease onset. Histological data comparing joint infiltration and cartilage damage in day 14 collagen-arthritic mice treated with control IgG or anti-OSM antibody are shown in FIG. 8. Control IgG treated mice exhibited extensive joint infiltration by PMNs and mononuclear cells (FIG. 8a). This was accompanied by surface destruction of the articular cartilage, characterised by widespread neutrophil infiltration (FIG. 8b). By contrast, FIGS. 8c and d show representative joints of an anti-OSM treated animal with minimal arthritis, demonstrating a markedly reduced level of cellular infiltrate, with intact articular cartilage. In addition, joints were scored blindly for histopathological appearance of cartilage and synovium and reported as normal, moderate or severe. A total of 73 individual joints per treatment group were assessed; data are summarised in Table 1. In the animals treated with anti-OSM, 47% of the joints examined were normal or exhibited a mild synovitis, compared to only 6% in the control IgG treated group. Similarly, in anti-OSM treated mice, 58% of the joints examined showed little or no cartilage damage compared to 21% in the control IgG treated group. The joints of the two anti-OSM treated mice with clear signs of joint redness and swelling at day 1 of treatment subsequently showed complete amelioration of arthritis and exhibited neither cellular infiltration nor visible abnormalities to either cartilage or synovium (data not shown).

TABLE 1

Histological scoring of joints from mice treated with either anti-OSM or control IgG.

| | Normal/Mild | | Moderate | | Severe | |
|---|---|---|---|---|---|---|
| Treatment | cartilage | synovium | cartilage | synovium | cartilage | synovium |
| anti-OSM | 58% | 47% | 21% | 23% | 22% | 31% |
| IgG | 21% | 6% | 26% | 37% | 53% | 57% |

Total joints examined: 73 joints/treatment

EXAMPLE 7

Identification of Small Organic Molecule Antagonists

Small organic molecule antagonists of OSM were identified by inhibition of an OSM-induced biological response from a reporter cell line without causing overt cell toxicity. As a control the effect of the compounds on a TNFα-responsive cell-line was also tested.

EXAMPLE 7a

Expression and Purification of Human OSM

A DNA fragment encoding human OSM (hOSM) with the 25 amino acid leader sequence removed was amplified using the Polymerase Chain Reaction (PCR) from an activated leukocyte cDNA library using the synthetic oligonucleotide primers 5'-GCATAGGATCCGCGGCTATAGGCAGCT-GCTCG-3' (SEQ ID 5) and 5'-ATCGCGAATTCCTAC-CGGGGCAGCTGTCCCCT-3', (SEQ ID 6) designed from the EMBL sequence for hOSM (accession number M27288). This PCR product was sub-cloned into pCR2.1 (Invitrogen) to give pCR2.1hOSM.

A SalI restriction endonuclease cleavage site was created within the Factor Xa site in the bacterial expression vector pGEX-3X (Pharmacia) by insertion of AC for TG using 'Quickchange' site directed mutagenesis kit (Stratagene) to create the sequence depicted below (SEQ ID 7);

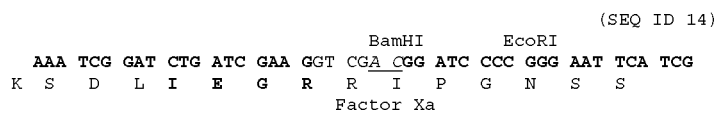

Following sequence verification of the OSM insert in pCR2.1hOSM, DNA encoding the mature form of human OSM was PCR amplified from this vector using the forward primer 5'-GATACGATCGTCTCATCGAGCGGCTATAG-GCAGCTGC-3' (SEQ ID 8) containing a BsmBI restriction endonuclease site (underlined), and the reverse primer 5'-AT-TACATGGAATTCCTATCTCCGGCTCCGGTTCGG-3' (SEQ ID 9) containing an EcoRI site (underlined). This PCR product contains the mature form of human OSM without the leader sequence and without the 31 amino acids from the C-terminus which are removed upon protein maturation. Following PCR, the amplified DNA fragment was purified, digested with restriction enzymes BsmBI and EcoRI and sub-cloned into the modified pGEX-3X vector (Pharmacia: containing DNA encoding GST) which was restricted with SalI and EcoRI to generate a plasmid designated pGEX 196. Following sequence verification, the plasmid pGEX196 was transformed into E. coli BLR-DE3 (Novagen). The transformed cells were cultured in 2×YT+G media (tryptone 16 g/l; yeast extract 10 g/l; NaCl 5 g/l; pH 7.0 with NaOH; 2% glucose) supplemented with 100 ug/ml ampicillin.

To prepare purified protein an overnight culture of pGEX 196 in E. coli BLR-DE3 was diluted 1:100 and this culture was grown at 37° C. to an $A_{600\ nm}$ of 0.8. Expression of the GST-hOSM fusion protein was induced by the addition 0.1 mM IPTG (Isopropyl-1-thio-β-D-galactopyranoside) and the culture maintained for a further two hours.

GST-hOSM was isolated from the E. coli culture by batch purification. A 3 liter bacterial culture was harvested by centrifugation at 3000 rpm and the resulting pellet resuspended in 50 ml ice cold PBS (Phosphate Buffered Saline) containing Proteinase inhibitor tablets (Boerhinger). 5 ml of lysozyme was added and the cell suspension incubated on ice for 5 minutes. The cells were sonicated at 4° C. and 1% Triton X100 and 10 mM dithiothreitol was added. The lysate was then end over end mixed at 4° C. for 10 minutes, and then centrifuged at 14000 g. The supernatant was added to glutathione agarose (Sigma cat no. G4510) and end over end mixed at 4° C. for 30 minutes. The suspension was centrifuged lightly, the supernatant aspirated off and the settled agarose was washed twice with ice cold PBS. Elution buffer (20 mM glutathione, 100 mM Tris pH 8.0, 100 mM NaCl; pH 8.0 again) was added and the suspension was incubated on ice for 5 minutes. The supernatant was collected and fractions were analysed by Sodium dodecyl sulphate/polyacrylamide gel electrophoresis (SDS-PAGE), followed by staining in Coomassie brilliant blue dye, to confirm the integrity of the purified protein.

Proteolytic cleavage optimisation experiments were set up using Factor Xa and thrombin, with thrombin yielding the optimum amount of hOSM as demonstrated by coomassie brilliant blue stained SDS-PAGE analysis. Separation of the GST and OSM products was achieved by ion exchange chromatography and the purified OSM product was verified by N-terminal sequencing and mass spectrometry.

EXAMPLE 7b

HepG2 B6: OSM-Induced sPAP Assay

A HepG2 cell line (ECACC) was stably transfected with six functional STAT3 response elements (REs) upstream of sPAP (secreted placental alkaline phosphatase) cDNA as described below to form HepG2B6. STAT3 (signal transducer and activator of transcription) is an intermediate in the IL-6 cytokine family intercellular signalling cascade. Following dimerisation of cell surface receptors STAT3 is phosphorylated and will then bind to DNA REs in the nucleus and activate DNA downstream, in this construct that DNA is sPAP. Thus this line can be driven to produce sPAP by overnight incubation in Oncostatin M.

A STAT responsive secreted placental alkaline phosphatatse (sPAP) reporter gene was constructed as follows. Initially an oligonucleotide pair containing three copies of a palindromic STAT3 response element (Wegenka U. M et al Mol Cell. Biol, 1993 Vol 13 p 276-288 Table 1 on p 277) and a 5' Xho1 site was cloned into the unique Sal1 site of the plasmid pBluescript tk-SPAP to create pllP3-tk-SPAP. A further six copies of a synthetic oligonucleotide encoding the STAT3 response element found in the Fibrinogen β promoter (Dalmon et al, Mol Cell Biol; 1993; 13: 1183-1193 FIG. 9 the hβFG sequence including IL6RE Consensus motif and TTG leader without the GAT tail) were then cloned into the Xho1 site of pllP3-tk-SPAP to generate pllx6/llP3-tk-SPAP. Following sequencing to confirm the number of response elements pllx6/llP3-tk-SPAP was digested with Nru1 and Xba1 to isolate a fragment of DNA containing 9STAT response elements and the tk-SPAP coding sequence. This was subsequently transferred between the Nru1 and Xba1 sites of the plasmid pcDNA4 (Invitrogen) (replacing the CMV promoter) to create a SPAP gene reporter containing 9 STAT3 responsive elements, and NeoR selectable marker for establishment of the HepG2 cell line.

HepG2 cells (ECACC) were grown in DMEM media supplemented with 2 mM L-glutamine, 1% NEAA and 10% HI foetal calf serum at 37° C. in an atmosphere of 5% $CO_2$, 92% humidity. For transfection with the STAT-sPAP reporter, cells were plated at 1% confluence in a 10 cm tissue culture dish and transfected with 10 ug of the STAT-sPAP reporter vector using a calcium phosphate transfection kit (Invitrogen). Following clonal selection in the presence of 1 mg/ml G418 individual cell lines were screened for the ability of IL-6 to cause an increase in the expression of sPAP from the STATsPAP reporter gene.

HepG2 B6 cells were plated into 96 well plates to a final concentration of $3\times10^4$ cells per well in 100 μl of media (DMEM (Sigma), 10% HI FCS, 1% non-essential amino acids, 2 mM Glutamine, 500 μg $ml^{-1}$ G418, (all from Life Technologies)). Cells were allowed to equilibrate for 48 hours. Putative anti-OSM solid compounds were made up to a stock dilution of 20 mM in DMSO and serially diluted 1:3 in DMSO. This was then further diluted in HepG26B assay media, this is as above media but with 1% heat inactivated FCS, low alkaline phosphatase activity (Life Technologies) substituted for 10% HI FCS. Compounds were diluted 1:3 from a top concentration of 200 μM to a final concentration of 0.09 μM in a final concentration of 1% DMSO. (That is 200, 66.67, 22.22, 7.41, 2.47, 0.82, 0.27, 0.09 and 0 μM). The old media was removed from the wells and replaced with diluted compound also containing 2 ng $ml^{-1}$ OSM (R&D Systems), cells were incubated for a further 20 hours. Each dilution was performed in triplicate. 20 μl of media was removed from each well and assayed for sPAP activity using pNPP (p-Nitrophenyl phosphate; Sigma), as a substrate. Endogenous alkaline phosphatase is blocked with L-homoarginine. Optical density of substrate is read at 405-650 nm. Concentration of compound is plotted against OD as a measure of sPAP produced and can be analysed to determine IC50 values.

EXAMPLE 7c

A549 Cells: TNFα-Induced sPAP Assay

This assay used A549 cells that had been stably transfected with a reporter gene, comprising the cytokine responsive region of the E-selectin gene coupled to alkaline phosphatase (Ray et al., Biochem J. 328:707-715, 1997). This transfected cell line can be driven to produce sPAP by overnight incubation with TNFα.

A549 cells were plated into 96 well plates to a final concentration of $5 \times 10^4$ cells per well in 100 µl of media. Cells were allowed to equilibrate for 24 hours. Putative anti-OSM solid compounds are made up to a stock dilution of 20 mM in DMSO and serially diluted 1:3 in DMSO. This was then further diluted in media (DMEM, 1% heat inactivated FCS, low alkaline phosphatase activity, 1% non-essential amino acids, 2 mM Glutamine, 500 µg ml$^{-1}$ G418, (all from Life Technologies), to give a concentration response of 0.09-200 µM in a final concentration of 1% DMSO. The old media was removed from the wells and replaced with diluted compound also containing 3 ng ml$^{-1}$ TNFα (R&D Systems), cells were incubated for a further 20 hours. Each dilution was performed in triplicate. 20 µl of media was removed from each well and assayed for sPAP activity using p-Nitrophenyl phosphate (Sigma), as a substrate. Endogenous alkaline phosphatase is blocked with L-homoarginine (Sigma). Optical density of substrate is read at 405-650 nm. Concentration of compound is plotted against OD as a measure of sPAP produced and can be analysed to determine IC50 values.

EXAMPLE 7d

Cell Viability Assay

Cell viability was measured as the ability of dehydrogenase enzymes in metabolically active cells to reduce a tetrazolium compound (3-(4,5-dimethylthiazol-2-yl)-5-(3-carboxymethoxyphenyl)-2-(4-sulfophenyl)-2H-tetrazolium, inner salt; MTS to a soluble formazan product that can be directly measured at 490 nm.

A solution of 2 mg/ml MTS (Promega) containing 0.046 µg/ml of phenazine methosulphate (PMS; Sigma) was prepared in Dulbeccos PBS. Following removal of medium for assay of sPAP activity, 20 µl/well of MTS/PMS was added. Cells were then incubated for a further 45 minutes. The absorbance at 490 nm was then measured using a reference of 630 nm.

EXAMPLE 7e

Antagonists

N-(1H-pyrazolo[3,4-d]pyrimidin-4-yl)benzamide (Davoll and Kerridge, J. Chem. Soc. 2589, 1961) (GW 340442x) produced a concentration-dependent inhibition of OSM-induced sPAP release with an $IC_{50}$ of 0.3 µM (FIG. 9), but was much less potent at inhibiting TNFα-induced sPAP (approx. $IC_{50}$ value of 92 µM) (FIG. 10). Therefore this compound has greater than 100-fold selectivity for OSM over TNFα.

EXAMPLE 8a

Generation and Testing of Anti-Human OSM Antibodies

Monoclonal antibodies were raised against human OSM (R+D systems) in mice as follows; SJL female mice (Jackson Inc. Bar Harbor, Mass.) were immunized with recombinant human OSM (R&D systems) with either a combination of 1 µg of recombinant human OSM antigen emulsified in RIBI adjuvant (RIBI, Hamilton, Mont.) subcutaneously and 1 µg of antigen in Freund's complete adjuvant intraperitoneally on days 0, 3, 5, and 24 (on day 27, the mouse was given an intraperitoneal injection of 1 µg of antigen in saline); or 1 µg of antigen emulsified in RIBI adjuvant on days 0, 3, 5, 24 and 53 intraperitoneally (on day 54, the mouse was injected with 1.5 µg of antigen in saline intraperitoneally).

Twenty four hours after the last immunization, the mice were sacrificed, and splenocytes were harvested and prepared for fusion. The fusion procedure was as described in Su J-L et al: Hybridoma 1998; 17(1): 47-53.). Briefly, splenocytes and myeloma cells P3X63Bcl-2-13 (Kilpatrick K E, et al Hybridoma 1997; 16(4):387-395) at ratio of 5:1 or 1:1 were fused using polyethylene glycol 1500 (Boehringer Mannheim, Germany). Fused cells were resuspended at $1 \times 10^6$ cells/ml in hybridoma growth media that is composed of equal volume of RPMI 1640 (Life Technologies, Inc., Gaithersburg, Md.) and EXCELL-610 (JRH Biosciences, Lenexa, Kans.) supplemented with 10% fetal bovine serum (Hyclone, Logan, Utah), 1× Origen Hybridoma Cloning Factor (Igen, Gaithersburg, Md.), 2 mM L-glutamine, and penicillin/streptomycin. Cells were then plated in 24-well microtiter plates (Costar, Cambridge, Mass.) at 1 ml/well. Twenty four hours later, 1 ml of 2×HAT-selection media; 100 µM hypoxanthine, 0.4 µM aminopterin, 16 µM thymine (Life Technologies, Inc.) in hybridoma growth media was added to each well. After 2 weeks of culture at 37° C., 5% CO2, hybridoma supernatants were screened for secretion of anti-OSM antibodies by ELISA. Limiting dilution cloning was performed on selected hybridomas.

Hybridoma supernatants and diluted sera were incubated in 96 well plates containing bound human OSM. Anti-hOSM antibodies were detected by alkaline phosphatase anti-mouse antibodies. Duplicate O.D. values for antibodies giving a positive result are given in Table 2.

TABLE 2

| Hybridoma | OD 1:10 | OD 1:100 | OD 1:1000 |
|---|---|---|---|
| OM5-6.1 | 1.346 | 0.901 | 0.302 |
|  | 1.329 | 0.929 | 0.249 |
| OM5-6.10 | 1.347 | 1.017 | 0.296 |
|  | 1.434 | 1.122 | 0.352 |
| OM6-10.111 | 1.77 | 1.073 | 0.36 |
|  | 1.615 | 1.557 | .0524 |

| Mouse sera | OD 1:500 | OD 1:2500 | OD 1:5000 |
|---|---|---|---|
| M1 | 0.006 | 0 | 0.005 |
|  | 0.006 | 0.001 | 0.003 |
| M2 | 1.843 | 1.086 | 0.73 |
|  | 1.86 | 1.052 | 0.794 |
| M3 | 1.405 | 0.445 | 0.198 |
|  | 1.338 | 0.324 | 0.217 |
| M4 | 1.48 | 0.537 | 0.18 |
|  | 1.631 | 0.484 | 0.18 |

Three of the supernatants and all but one of the mouse sera gave positive results in the ELISA. Using the ELISA data a crude measure of antibody concentration was determined and the positive antibodies were then titrated against 2 ng ml-1 OSM in the HepG2 B6 sPAP assay described in Example 7b. In summary, an antibody was incubated overnight with the cytokine at 4° C. before being incubated with the HepG2 B6 cells. sPAP production was assayed as described in Example 7b. Inhibition of sPAP production by the hybridoma supernatants and the mouse sera are shown in FIG. 11.

EXAMPLE 9a

Identification of Key Binding Residues for the Receptor on OSM

The receptor binding sites on hOSM were identified initially by reference to related members of the IL6-family of cytokines. Sites 1 and 3 are thought to be involved in binding to the cytokine specific chain/s of the receptor whilst site 2 is thought to be involved in binding to the common receptor component gp130. Studies of mutations at site 2 in the IL-6 family cytokines leukaemia inhibitory factor (LIF) (Hudson et al (1996) J. Biol Chem 271, 11971-11978), interleukin-6 (IL-6) (Paonessa et al (1995) EMBO J. 14, 1942-1951 and Savino et al (1994) EMBO J. 13 1357-1367) suggest that changes to residues within site 2 can result in altered binding to gp130. In order to investigate the residues of OSM that are important for its interaction with gp130 it was necessary to identify those residues that would be exposed at the surface of OSM in the region of site 2. Using the information from nmr experiments (Hoffman et al (1996) J. Biomol. NMR 7 273-282) and the published structure of LIF (Robinson et al (1994) Cell 77 1101-16) a homology model of OSM was constructed. Residues that occupy surface positions in this model in the site 2 region were selected for mutagenesis. The structure of the complex formed between growth hormone (a homologue of OSM) and its receptor has been determined (De Vos et al (1992) Science 255 306). By superimposing the model of OSM with growth hormone further sites of potential interaction between OSM and gp130 were identified.

Based on these modelling studies, 27 sites were selected for mutation in OSM to investigate its interaction with gp130, See Table 3. At each of these sites an alanine residue was substituted for the wild type residue.

TABLE 3

| Site | Location | Comments |
|---|---|---|
| Ser 7 | N-terminal region | |
| Lys 8 | N-terminal region | |
| Glu 9 | N-terminal region | |
| Tyr 10 | Helix A | |
| Arg 11 | Helix A | |
| Leu 13 | Helix A | In the current model the exposure of these leucines is borderline. If there is a distortion in the helix below residue 17 the upper part of helix 1 might be rotated and these residues buried |
| Leu 14 | Helix A | |
| Leu 17 | Helix A | |
| Gly 15 | Helix A | |
| Gln 16 | Helix A | Residues 16-22 are an almost continuous run of hydrophilic residues if the underlying structure here is helical then some of these may be buried in the core of the protein and presumably have partnering residues to which they hydrogen bond. Alternatively the helix is distorted in this region and most of these residues are exposed. |
| Gln 18 | Helix A | |
| Lys 19 | Helix A | |
| Gln 20 | Helix A | |
| Thr 21 | Helix A | |
| Asp 22 | Helix A | |
| Gln 25 | Helix A | |
| Asp 26 | Helix A | |
| Met 113 | Helix C | |
| Pro 116 | Helix C | |
| Asn 117 | Helix C | |
| Leu 119 | Helix C | |
| Gly 120 | Helix C | No functionality in side chain but one of a quadruple mutant of human LIF affecting gp130 binding |
| Arg 122 | Helix C | |
| Asn 123 | Helix C | |
| Asn 124 | Helix C | |
| Tyr 126 | Helix C | |
| Gln 130 | Helix C | |

EXAMPLE 9b

Synthesis of Mutant OSM-GST Fusion Molecules

For each of the 27 mutations a pair of mutagenic oligonucleotides was designed. These were approximately 33 bases in length and preferably had a G or C residue at either end. These were annealed to the pGEX (Pharmacia) derived expression containing the 'wild type' OSM DNA (see SEQ ID 12) under the control of a lac (/IPTG inducible) promoter (Pharmacia) and extended using native Pfu polymerase (Stratagene). The original template DNA was digested with Dpn1 (New England Biolabs) and the newly synthesised plasmid (which was not a substrate for Dpn1) was transformed into the *E. coli* strain DH5alpha (GibcoBBL/Life Technologies). A small set (typically 4) of colonies was picked, the plasmid DNA was isolated and the DNA sequence was determined. A representative mutant clone for each mutation, along with a similarly constructed wild type were transformed into *E. coli* strain BLR (non DE3: Novagen) for expression of the recombinant proteins. 0.51 cultures were established and induced at an OD550 of approximately 0.5. After 3 hours of induction the cells were pelleted by centrifugation and lysed using a combined method of lysozyme and sonication. Since the recombinant mutant proteins were expressed as fusions with GST, glutathione sepharose columns were used to bind the fusions. The fusion proteins were then eluted from the columns using free glutathione and were then incubated in 10 mm DTT for 4 hours at room temperature to remove the glutathione adduct and stored at −80° C.

EXAMPLE 9c

Effect of Point Mutations on the Ability of OSM-GST to Compete with Wild Type OSM Binding to Gp130-Fc in an ELISA Nunc Immunoplates (F6 Maxisorp, Life Technologies) were coated overnight (4° C.) with wild type OSM (produced according to Example 7a); 50 μl/well, 1 μg/ml in carbonate/bicarbonate buffer pH 9.4). Plates were washed (×6 in PBS 0.05% tween 20, using Skatron Plate washer), tapped dry and blocked to reduce non-specific binding (200 μl/well, 1% BSA/PBS). Following 1 h incubation (room temperature on a shaking platform) the plates were tapped dry and wild type (wt) or mutant OSM-GST from Example 9b added (50 μl/well, 20-0.002 μg/ml, titrated in 1% BSA/PBS). As a positive control polyclonal anti-human OSM antibody (R&D Systems) was also tested (20-0.02 μg/ml). A complex of gp130-Fc (Produced as below 300 ng/ml) and anti-human IgG alkaline phosphatase conjugate (1:500, Sigma) in 1% BSA/PBS (50 μl/well) was added immediately after the agents under test. Following a 5 h incubation (room temperature on a shaking platform) the plates were washed (×6) and developed using ELISA Amplification System (Life Technologies) as manufacturer's instructions and the OD measured at 490 nm. On each plate the total binding was determined by gp130-Fc/conjugate and OSM in the presence of 1% BSA/PBS, and non-specific binding by gp130-Fc/conjugate in absence of OSM, or conjugate binding to OSM in absence of gp130-Fc.

DNA encoding the extracellular domain of human gp130 was amplified by Polymerase Chain Reaction (PCR) using synthetic oligonucleotide primers,

```
forward primer,
                                          SEQ ID 10
5'CATCGGATCCAAGCTTTACAGTTACTGAGCACAGGACCTCACC
     BamHI   HindIII  5'UTR sequence (SEQ ID 15)
ATGTTGACGTTGCAGACTTG
 M L   T L Q  T
and reverse primer
                                          SEQ ID 11
5'CATCCTCGAGTTTCTCCTTGAGCAAACTTTGG
      XhoI
``` designed from the GenBank database sequence (accession number M57230) for human gp130. The forward primer contained BamHI, and HindIII restriction endonuclease sites, and a consensus 5' untranslated sequence followed by DNA sequence complementary to the start of the gp130 coding sequence. The reverse primer contained a XhoI restriction endonuclease site followed by DNA sequence complementary to the 3' end of the extracellular domain of the gp130 coding sequence. This PCR fragment was purified and sub-cloned into pCR2.1 (Invitrogen) to give pCR2.1 gp 130.

The plasmid pCR2.1gp130 was digested with restriction enzymes BamHI and XhoI and the gp130 fragment was purified and sub-cloned into the BamHI and XhoI endonuclease sites in a plasmid containing a DNA sequence encoding an Fc fragment of human IgG1. The plasmid was then digested with the restriction enzyme HindIII, and the resulting gp130Fc fragment was purified and subcloned into the HindIII site of a baculovirus expression vector, pFastBac1 (Life Technologies), to generate a plasmid designated pBACgpFc.

The fusion protein gp130Fc was expressed in insect cells using the Bac-to-Bac baculovirus expression system (Life Technologies) and was then purified from the cell culture supernatant by protein A affinity column chromatography and verified by coomassie brilliant blue stained SDS-PAGE and by western blot analysis using commercially available anti-gp130 and anti-hIgG antibodies.

Mutant and wt OSM-GST were tested to obtain $IC_{50}$ in 3-6 experiments. The mean OD in the presence of OSM and gp130-Fc in the absence of competing ligand (ie total binding) was 1.157 (range 0.825-1.807) and the non specific binding was less than 0.08. The anti-OSM antibody produced a concentration-dependent inhibition in all assays (74±1% inhibition at 1 µg/ml). The wt OSM-GST competed with plate-bound OSM to give a concentration dependent inhibition (FIG. 12), with an IC50 of 0.139±0.0258 µg/ml determined in 6 independent experiments. The potency of mutant OSM-GST at competing with plate-bound wt OSM is summarised in Table 4. Mutations which resulted in a substantial decrease in the ability to compete with wt OSM for gp130 binding were L13A, Q16A, Q20A, G120A, N123A and N124A. Of these, Q20A and Q16A were the weakest: at the maximum concentration tested (10 µg/ml) Q20A produced 66±2.3% and Q16A only 15±8% inhibition (FIG. 12)

TABLE 4

Potency of wt and mutant OSM-GST at competing with plate-bound wt OSM for binding to gp130-Fc in the ELISA. $IC_{50}$ values were determined in 3-6 independent experiments.

| Mutant | IC50 [µg/ml] | | | | Mean | Std. Error |
|---|---|---|---|---|---|---|
| wild type | 0.110 | 0.120 | 0.257 | | 0.139 | 0.026 |
|  | 0.136 | 0.070 | 0.142 | | | |
| (1) S7A | 0.199 | 0.078 | 0.121 | | 0.133 | 0.035 |
| (2) K8A | 0.252 | 0.055 | 0.106 | | 0.138 | 0.059 |
| (3) E9A | 0.208 | 0.163 | 0.097 | | 0.156 | 0.032 |
| (4) Y10A | 0.320 | 0.180 | 0.168 | | 0.223 | 0.049 |
| (5) R11A | 0.181 | 0.255 | 0.280 | | 0.239 | 0.030 |
| (6) L13A | 2.960 | 1.990 | 2.640 | | 2.530 | 0.285 |
| (7) L14A | 0.660 | 0.470 | 0.412 | | 0.514 | 0.075 |
| (8) G15A | 0.090 | 0.203 | 0.171 | | 0.155 | 0.034 |
| (9) Q16A | >10 | >10 | >10 | | >10 | |
| (10) L17A | 2.210 | 1.900 | 1.350 | | 1.820 | 0.251 |
| (11) Q18A | 0.320 | 0.310 | 0.555 | | 0.395 | 0.080 |
| (12) K19A | 0.047 | 0.075 | 0.300 | 0.040 | 0.116 | 0.062 |
| (13) Q20A | 4.130 | 5.570 | 4.100 | 6.200 | 5.000 | 0.527 |
| (14) T21A | 0.108 | 0.044 | 0.101 | | 0.084 | 0.020 |
| (15) D22 | 0.040 | 0.080 | 0.092 | | 0.071 | 0.016 |
| (16) M113A | 0.511 | 0.199 | 0.252 | | 0.321 | 0.096 |
| (17) P116A | 0.232 | 0.169 | 0.197 | | 0.199 | 0.018 |
| (18) N117A | 0.983 | 0.756 | 0.617 | | 0.785 | 0.107 |
| (19) L119A | 0.272 | 0.266 | 0.227 | | 0.255 | 0.014 |
| (20) G120A | 3.650 | 2.680 | 2.950 | | 3.090 | 0.289 |
| (21) R122A | 0.140 | 0.220 | 0.167 | | 0.176 | 0.024 |
| (22) N123A | 4.750 | 1.570 | 2.560 | | 2.960 | 0.940 |
| (23) N124A | 1.630 | 1.950 | 2.380 | | 1.990 | 0.217 |
| (24) Y126A | 0.386 | 0.359 | 0.400 | | 0.382 | 0.012 |
| (25) Y130A | 0.145 | 0.180 | 0.094 | | 0.140 | 0.025 |
| (26) Q25A | 0.042 | 0.036 | 0.055 | | 0.044 | 0.006 |
| (27) D26A | 0.170 | 0.280 | 0.481 | | 0.310 | 0.091 |

EXAMPLE 9d

Effect of Point Mutations in OSM on Production of OSM Driven sPAP in a HepG2 B6 In Vitro Assay The assay described in Example 7b above was employed. OSM-GST mutants were diluted to a concentration of 100 ng ml$^{-1}$ using the known concentration of intact OSM mutants generated in Example 9b. A wild type OSM-GST was included for control purposes. Dilutions were made in HepG2 B6 media with 1% heat inactivated FCS, low alkaline phosphatase activity. Serial 1:3 dilutions were then made. (100; 33.33; 11.11; 3.7; 1.23; 0.4 ng ml$^{-1}$). $3 \times 10^4$ HepG2 B6 were dispensed into individual well of a 96 well plate in 100 µl of media. Cells were allowed to equilibrate for 48 hours. Media was then removed and replaced with 100 µl of diluted OSM-GST mutant. Cells were incubated for a further 20 hours. Each dilution was performed in triplicate. 20 µl of media was removed and assayed for sPAP using pNPP as a substrate. Endogenous ALP was blocked with L-homoarginine. O.D. was read at 405-650 nm. The experiment was repeated twice.

Most of the mutants could drive sPAP release in a similar manner to the wild type. Three mutants produced very low levels of sPAP. $EC_{50}$s were not obtained from these mutants. (FIG. 13) shows the O.D. plots obtained from mutants 9 (Q16A), 13 (Q20A) and 20 (G120A), which were less effective at driving sPAP production. The wt OSM-GST is shown for comparison. These data were used to calculate $EC_{50}$ values. Actual $EC_{50}$s for each mutant and expressed as a percentage of the wild type are shown in Table 5.

TABLE 5

| Mutant | Expt 1 % | Expt 1 EC$_{50}$ ng ml$^{-1}$ | Expt 2 % | Expt 2 EC$_{50}$ ng ml$^{-1}$ | Expt 3 % | Expt 3 EC$_{50}$ ng ml$^{-1}$ | Mean % | 'Potency' |
|---|---|---|---|---|---|---|---|---|
| WT | 100 | 24 | 100 | 32 | | | 100 | |
| 1 S7A | 50 | 12 | 69 | 22.2 | | | 59.5 | MORE |
| 2 K8A | 66 | 16 | 38 | 12.5 | | | 52 | MORE |
| 3 E9A | 98 | 23.6 | 27 | 8.9 | | | 62.5 | MORE |
| 4 Y10A | 134 | 32.4 | 256 | 82 | | | 195 | LESS |
| 5 R11A | 118 | 28.6 | 86 | 27.7 | | | 102 | EQUAL |
| 6 L13A | 269 | 65.7 | 171 | 54.9 | | | 220 | LESS |
| 7 L14A | 81 | 19.4 | 77 | 24.9 | | | 79 | MORE |
| 8 G15A | 87 | 21 | 55 | 17.8 | | | 71 | MORE |
| 9 Q16A | | NC | | NC | | | | NONE |
| 10 L17A | 301 | 72.7 | 174 | 56 | | | 237.5 | LESS |
| 11 Q18A | 84 | 20.2 | 68 | 21.7 | | | 76 | MORE |
| 12 K19A | 98 | 23.6 | 37 | 11.9 | | | 67.5 | MORE |
| 13 Q20A | | NC | | NC | | | | NONE |
| 14 T21A | 71 | 17 | 33 | 10.5 | | | 52 | MORE |
| 15 D22 | 152 | 36.7 | 50 | 16 | | | 101 | EQUAL |
| 16 M113A | 106 | 25.6 | 78 | 25 | | | 92 | EQUAL |
| 17 P116A | 104 | 25 | 47 | 15 | | | 75.5 | MORE |
| 18 N117A | 241 | 58 | 132 | 42.5 | | | 186.5 | LESS |
| 19 L119A | 115 | 27.8 | 72 | 23 | | | 93.5 | EQUAL |
| 20 G120A | | NC | | NC | | | | NONE |
| 21 R122A | 135 | 32.4 | 43 | 13.8 | 124 | 47.3 | 101 | EQUAL |
| 22 N123A | 157 | 37.9 | 154 | 49.7 | | | 155.5 | LESS |
| 23 N124A | 125 | 30.2 | 113 | 36.2 | | | 119 | EQUAL |
| 24 Y126A | 386 | 93 | 32 | 10.3 | 106.5 | 40.8 | 175 | LESS |
| 25 Q130A | 52 | 12.5 | 26 | 8.2 | | | 39 | MORE |
| 26 Q25A | 55 | 13.3 | 41 | 13 | | | 48 | MORE |
| 27 D26A | 81 | 19.5 | 79 | 25.5 | | | 80 | EQUAL |

EC$_{50}$ values expressed as a percentage of Wild Type EC$_{50}$ and actual EC$_{50}$ values are shown. <80% More potent; 80-120% Equal potency; >120% Less potent than wild type.
NC—not calculated Examination of this table shows three of those mutants which are substantially different from wt in the ELISA are also less potent in the sPAP assay, 6-L13A; 10-L17A; 22-N123A and the fourth, 23-N124A fall just into the equally potent grade by the arbitary scoring system. Thus both assay types show good concordance. Several of the mutants were less 'potent' than wild type in driving sPAP production but there was variation between the two experiments, except in those mutants (Q16A, Q20A, G120A) that didn't drive sPAP at all. The assay results indicate that G120A, Q16A and Q20A effect binding of OSM to gp130. N123A and N124A also appear to have some effect on interactions with gp130.

EXAMPLE 10

Role of OSM in Gastritis

H. pylori is a Gram negative spiral shaped bacterium that has been implicated in causing gastritis, peptic ulcer disease and gastric cancer. H. pylori Cag+ strains have a higher incidence with ulcers than H. pylori Cag− strains. H. pylori strains (more pathogenic Cag+, and Cag−) were co-cultured in-vitro with gastric epithelial cell line KATO III (ECACC) to investigate the host response to H. pylori infection by differential gene expression analysis. mRNA was isolated at time points: 45 mins, 3 hours and 24 hours, derived radioactive probes were hybridised to high density cDNA gene arrays (containing approximately 136 human genes including cytokines, cytokine receptors and adhesion molecules). Analysis of the gene expression profiles obtained revealed induction/repression of numerous genes in response to the H. pylori strains. Oncostatin M was found to be induced in cells exposed to the highly pathogenic strain of H. pylori (Cag+) compared to cells exposed to the weakly pathogenic H. pylori (Cag−) or un-treated control cells.

EXAMPLE 11

Generation of an OSM-Targeted RNA Aptamer

EXAMPLE 11a

Aptamer Generation by SELEX

Iterative rounds of selection/amplification were performed as described (Fitzwater and Polisky, Meths. in Enzymol. 1996, 267, 275-301) except that OSM-GST protein produced in accordance with Example 7a was bound to a 96 well plate for the partition phase of the SELEX process. 2'-fluoropyrimidine modified RNA containing a randomised region of 40 nucleotides was prepared by in vitro transcription from synthetic random DNA templates. Preparation of the DNA template (5'-ggaggacgaugcgg-40N-ccgcatcgtcctccc-3'), (SEQ. I.D. 21) designated 40N7, was achieved by the addition of a freshly prepared equimolar mixture of all four deoxynucleotide phosphoramidites by automated solid-phase synthesis according to manufacturers protocol on an Applied Biosystems ABI 394 instrument at a 1 μM scale. This template contains fixed 5' and 3' sequences separated by a 40 nucleotide random domain (designated 40N). Following synthesis the single stranded oligonucleotide template DNA was purified by gel electrophoresis. Conversion of the single stranded synthetic DNA template was purified by gel electrophoresis. Conversion of the single stranded synthetic DNA template to a double stranded (ds) DNA template was performed following elongation of the DNA template using the synthetic oligonucleotide primer 5'-d(taatacgactcactatagggaggacgat-gcgg)-3' (SEQ. I.D 22) using the Klenow fragment of E. coli DNA polymerase.

To generate a library of single stranded modified RNA molecules the dsDNA template was transcribed in vitro with T7 RNA polymerase using the 2' fluoro modified ribonucleotides rCTP and rUTP and 2'hydroxy rATP and rGTP. The reaction consisted of T7 RNAP buffer (20% (w/v) polyethylene glycol 8000, 200 mM Tris-HCl, pH8.0, 60 mM MgCl$_2$, 25 mM dithiothritol, 5 mM spermidine hydrochloride and 0.01% (v/v) Triton X-100) (Fitzwater and Polisky, Meths in Enzymol. 1996, 267, 275-301), 3 mM 2'F-rCTP, 3 mM 2'F-rUTP, 1 mM 2'OH-rATP, 1 mM 2'OH-rGTP, 2.5 U inorganic pyrophosphatase, 250 pmol purified dsDNA template 1750 Units T7 RNA polymerase in a total volume of 500 µl. The transcription reaction was incubated overnight at 37° C., treated with 10 Units DnaseI at 37° C. for 10 min then EDTA added to 40 µM to stop the reaction. The transcription was extracted three times with chloroform and concentrated using a Microcon™ concentrator. The RNA was purified from a 10% polyacrylamide gel containing 7M urea (Novex), eluted from the gel by the crush and soak method, ethanol precipitated and resuspended in water. Prior to incubation with 96 well plate immobilised hOSM, the RNA was heated to 95° C. for 2 min then cooled on ice.

For the SELEX experiment human OSM, obtained in accordance with Example 7a, at 3 µg/µl was diluted to the required concentration in SCHMK buffer (110 mM NaCl, 1 mM MgCl$_2$, 20 mM HEPES pH7.0, 1 mM CaCl$_2$, 5 mM KCL) and incubated in a 96 well microtitre plate (Labsystems) overnight at 4° C. to allow plate binding. The solution was removed from each well and 200 µl block buffer (0.1% I-block in SCHMK buffer) added. The plate was incubated at room temperature for 1 hour. RNA, diluted in 200 µl wash buffer (0.1% I-block, 0.05% Tween 20 in SCHMK buffer), was added to individual wells at the concentrations shown in Table 6.

TABLE 6

Protein/RNA ratios used during each round of the SELEX esperiment.

| Round of SELEX | OSM bound per well (µg) | RNA added per well (pmol) |
|---|---|---|
| 1 | 3 | 1000 |
| 2 | 3 | 500 |
| 3 | 3 | 500 |
| 4 | 3 | 500 |
| 5 | 3 | 500 |
| 6 | 0.6 | 400 |
| 7 | 0.6 | 400 |
| 8 | 0.12 | 400 |
| 9 | 0.12 | 400 |
| 10 | 0.06 | 400 |
| 11 | 0.06 | 400 |
| 12 | 0.06 | 400 |

The plate was incubated at 37° C. for 30 min after which individual wells were washed six times (200 µl each) with wash buffer at 37° C. to remove unbound RNA. To eluate specifically bound RNA 50 µl water was added to individual wells and the plate heated at 95° C. for 10 min. Reverse transcription was then carried out in individual wells, AMV Reverse Transcriptase buffer (Boehringer) 0.5 mM each dNTP, 100 pmol 3' primer, 20 Units AMV RT (Boehringer) in total volume 50 µl as described (Fitzwater and Polisky supra). After reverse transcription the oligonucleotide library was amplified by PCR was using the 5' oligonucleotide primer 5'-d(taatacgactcactataggggaggacgatgcgg)-3' (SEQ ID 22) and the 3' oligonucleotide primer 5'-d(tccggcgag tcgtctg)-3' (SEQ ID 16) for 18 cycles as described (Fitzwater and Polisky supra). PCR products were analysed on a 10% polyacrylamide gel and used for in vitro transcription to provide RNA for the next round of SELEX. The binding affinity of RNA pools for the starting protein was assessed after 7, 8, 10 and 12 rounds of SELEX and was measured in a nitrocellulose filter binding assay as described in Example 10b below (FIGS. 14 and 15).

The fully randomised starting pool of RNA did not bind to human OSM at any concentration tested. The apparent affinity dissociation constant ($K_d$) of the round 7 RNA pool for human OSM was 72 nM, this was further decreased to 20 nM after 12 rounds of SELEX as shown in Table 7.

TABLE 7

| Round of SELEX | $K_d$ (nM) |
|---|---|
| starting pool | >10 µM |
| 7 | 72 |
| 8 | 37 |
| 10 | 22 |
| 12 | 20 |

As there was little improvement in affinity between rounds 10 and 12, the round 12 pool of RNA was reverse transcribed to double stranded DNA and subcloned into the vector pCR2.1 as follows: RNA molecules were reverse transcribed to cDNA and made double stranded by PCR amplification with the primers 5'-d(ccgaagcttaatacgactcactatagg-gaggacgatgcgg)-3' (SEQ ID 17) and 5'-d(gccggatcctcgggc-gagtcgtctg)-3' (SEQ ID 18). DNA was then cloned using the TA cloning kit (Invitrogen) in the plasmid pCR2.1. Plasmid clones were sequenced according to a PCR sequencing protocol (Adams and Blakesley, 1991 Focus, 13, 56)

Following sub-cloning, 59 individual clones were sequenced. The sequence from these clones was aligned using the pileup software package of the GCG suite of molecular biology programs and is displayed in FIG. 16. Primary nucleotide sequence homologies indicated that the aptamer sequences fell into two main sequence families with 18 members (Family C) and 17 members (Family E), six minor families with between two and six members and four unique sequences which did not exhibit sequence homology with any other sequence (FIG. 16).

To further characterise individual aptamer sequences RNA was made from representative clones of each sequence family by in vitro transcription and the binding affinity for OSM determined as described in Example 10b. Representative binding curves are shown in FIG. 17, the apparent dissociation constants for all the sequences tested are summarised in Table 8.

TABLE 8

| Aptamer | Sequence Family | $K_d$ (nM) |
|---|---|---|
| ADR109 | A | >1000 |
| ADR63 | B | 38 |
| ADR58 | C | 7 |
| ADR104 | C | 8 |
| ADR120 | C | 9 |
| ADR151 | C | 752 |
| ADR152 | C | 6 |
| ADR157 | C | 228 |
| ADR163 | C | 106 |
| ADR117 | D | 600 |
| ADR70 | E | >1000 |
| ADR56 | F | >1000 |
| ADR100 | G | 35 |
| ADR159 | H | >1000 |
| ADR108 | Unique | 76 |

TABLE 8-continued

| Aptamer | Sequence Family | $K_d$ (nM) |
|---|---|---|
| ADR165 | Unique | >1000 |
| ADR66 | Unique | >1000 |
| ADR147 | Unique | >1000 |

Within the major family of eighteen members (Family C) the affinity for OSM varied from 7 nM for aptamer ADR 58 to 752 nM for ADR 151. Within this family all the sequences tested exhibited high affinity for human OSM. Within the second major family of 17 members (Family E), one sequence was tested (ADR 70). This bound weakly to human OSM with an apparent Kd of greater than 1 µM. Of the six smaller sequence families representative aptamers from family B (ADR 63) and family G (ADR 100) bound to OSM with affinities of 38 nM and 35 nM respectively. ADR 177 was examined a representative of family D. This bound to hOSM with lower affinity (Kd=600 nM). Representative aptamers from families A, E, F and H did not bind h OSM at any concentration tested. Of the three unique sequences examined only ADR 108 bound to human OSM with high affinity. Thus following 12 rounds of SELEX we have isolated a series of aptamers with high affinity for human OSM. These aptamers fall into families B, C, D and G and one unique sequence (ADR 108). As representatives of the high affinity sequence families, ADR 58, ADR 120, and ADR 152 were selected for further characterisation. However, any of the aptamers within these sequence families that exhibit high affinity binding to human OSM may be potentially used to antagonise the interaction of human OSM with the gp130 receptor. Dissociation binding in accordance with Example 10c demonstrated that of the aptamers tested ADR58 has the highest affinity for human OSM. The sequence of ADR58 is as follows:

(SEQ ID 19)
5-CCGAAGCTTAATACGACTCACTATAGGGAGGACGATGCGG--ATCGCC

CTGAACCGGCCCAGCAGACTGCTGACGGCACGAT--CAGACGACTCGCCC

GAGGATCCGGC-3'

EXAMPLE 11b

Dissociation Constant Measurements

Binding assays were carried out as described (Fitzwater and Polisky supra). Briefly nitrocellulose filter partitioning was used to determine the equilibrium dissociation constants ($K_d$s) for RNA libraries and aptamer clones after 7, 8, 10 and 12 rounds of Selex. Transcribed RNA was dephosphorylated using bacterial alkaline phosphatase for 30 min at 65° C. Dephosphorylated RNA was then 5' labelled using polynucleotide kinase and $\gamma^{33}$P ATP. Radiolabelled RNA was gel purified, and incubated at 37° C. for 30 min with a serial dilution of hOSM in SCHMK buffer (45 µl OSM plus 5 µl radiolabelled RNA at 1000 cpm/µl). OSM bound RNA was captured by filtering through nitrocellulose filter discs (0.45 µM pore, nitrocellulose/cellulose acetate mixed matrix filters, Millipore). The filters were washed immediately with 5 ml SCHMK buffer, dried and counted in a liquid scintillation counter. Equilibrium dissociation constants ($K_d$) were determined from equations described elsewhere (Jellinek et al. 1993 PNAS USA 90 11227). The data sets were fitted by the non-linear least squares method using an EXCEL software package (FIGS. 14 and 15).

EXAMPLE 11c

Binding Assays

A selection of aptamers which exhibited high binding affinity for human OSM (ADR 58, ADR 120, ADR 152) were characterised in an ELISA assay to investigate their ability to prevent the binding of human OSM to the gp130 receptor. An aptamer with low affinity for human OSM (ADR 66) and an aptamer raised against human CD95 ligand (ADR 147; 5'-TAATACGACTCACTATAGGGAGGACGATGCGGT-TATACTAAGCTGCGGTTAGCGAC AGCCCTC-CCTAGCGCCTCAGACGACTCGCCCGA-3') (SEQ ID 20) a protein unrelated to human OSM, were used as control sequences. The assay method was as follows:

ELISA experiments to examine inhibition of OSM binding to the gp130 receptor were performed as described in Example 9c except that PBS was replaced with SCHMK buffer throughout (110 mM NaCl, 1 mM, MgCl$_2$, 20 mM HEPES pH7.0, imM CaCl$_2$, 5 mM KCl). Following plate blocking to reduce non-specific binding as described, ADR58 or a pool of low affinity aptamers, generated in a SELEX experiment against human CD95 ligand, was added to the plates (50 µl/well, 0.34 nM-20 µM, titrated in SCHMK buffer) and incubated for 2 hours at room temperature prior to addition of gp130Fc/conjugate complex. The remainder of the assay was performed as described in Example 9c.

All three aptamers with high binding affinity for human OSM (ADR58, 120, 152) block binding of human OSM to the gp 130 receptor with an apparent IC$_{50}$ around 30 pmol/well RNA (FIG. 18). As might be expected the low affinity OSM aptamer ADR 66 appeared to block binding of human OSM to the gp130 receptor at high concentrations, while the non-specific ligand ADR147 appear to have little activity in this assay (FIG. 18).

To determine that the inhibition of the binding of human OSM to gp130 by sequence ADR58 was specifically due to the ability of the aptamer to bind to OSM to prevent the binding of OSM to gp130 a control ELISA experiment was performed. In this experiment we examined the ability of the aptamer to prevent binding of the primary antibody to assay plates coated with the gp130 receptor. The control assay was undertaken as follows:

Nunc Immunoplates (F6 Maxisorp, Life Technologies) were coated overnight (4° C.) with gp130 (50 µl/well, 200 ng/ml in carbonate/bicarbonate buffer pH 9.4). Plates were washed (×6 in PBS 0.05% tween 20, using Skatron Plate Washer), tapped dry and blocked to reduce non-specific binding (200 µl/well, 1% BSA/PBS). Following 1 h incubation (room temperature on a shaking platform) the plates were tapped dry and ADR58 or a pool of low affinity aptamers, previously generated in a SELEX experiment against human CD95 ligand, added (50 µl/well, 0.34 nM-20 µM, titrated in SCHMK buffer). Following a 2 h incubation (room temperature on a shaking platform) anti-human IgG alkaline phosphatase conjugate (1:500, Sigma) in 2% BSA/SCHMK buffer (50 µl/well) was added. Following a 5 h incubation (room temperature on a shaking platform) the plates were washed (×6) and developed using ELISA Amplification system (Life Technologies) as manufacturer's instructions and the OD measured at 490 nm. On each plate the total binding was determined by gp130-Fc and conjugate in the presence of BSA/SCHMK buffer, and non-specific binding of the conjugate to plate in the absence pf gp130-Fc.

As expected ADR 58 showed no activity in this assay indicating that the effects observed in the OSM/gp130 ELISA are specifically due to the binding of aptamer to human OSM (FIGS. 19A and 19B).

To determine if the high affinity aptamers generated in this study were capable of binding to human OSM to functionally antagonise the activation of the OSM receptor on HepG2 cells a reporter gene experiment was performed as described in Example 7b with the following variations. Anti-OSM aptamer (ADR 58, ADR 120 or ADR 152), or the non-specific aptamers ADR 66 or ADR 147) were serially diluted in 2 ng/ml hOSM in HepG2 B6 media containing 1% heat inactivated FCS and incubated overnight at 4° C. to allow binding of aptamer to hOSM. As described in example 7b old media was removed from the wells and replaced with 100 µl per well of aptamer/OSM cocktail. Each dilution was performed in triplicate. Cells were incubated in the presence of aptamer/OSM cocktail for 20 hours prior to collection of the culture media for sPAP assay as described in Example 7b. The three high affinity binding aptamers ADR58, ADR120, and ADR 152 blocked the ability of human OSM to activate the STAT-sPAP reporter gene in HepG2B6 cells with an $IC_{50}$ of around 10 pmol RNA/well (FIG. 20) The two aptamers that showed weak or no binding affinity for OSM and little activity in the OSM/gp130 ELISA also showed no activity in this assay.

EXAMPLE 11d

Specificity of ADR58

A number of experiments were performed to examine the specificity of aptamer ADR58 for human OSM over other homologous proteins. In the first experiment the binding specificity of ADR58 to human OSM was examined by determining the affinity dissociation constant of ADR 58 for human and mouse OSM as described in Example 10b. These two proteins are 42% homologous at the protein level. Dissociation binding experiments were using ADR 58 and human OSM generated in Example 7a, murine OSM (purchased from R&D systems), and a Glutathione-S-transferase-murine OSM fusion protein generated using similar methodology to Example 7a but based on the murine OSM sequence (GenBank Accession No D31942). While ADR58 bound to human OSM with an apparent Kd of 7 nM, the aptamer did not bind to murine OSM at any concentration tested (FIG. 21).

In a second experiment using the protocol set out below, the binding of ADR58 to the cytokine TNFα was examined. Nunc Immunoplates (F6 Maxisorp, Life Technologies) were coated overnight (4° C.) with sheep anti-human IgG (Serolabs) (50 µl/well, 1µ/ml in PBS). Plates were washed (×6 in PBS 0.05%, tween 20, using Skatron Plate washer), tapped dry and blocked to reduce non-specific binding (200 µl/well, 1% BSA/PBS). Following 1 h incubation (room temperature on a shaking platform) the plates were tapped dry and ADR58 or a pool of low affinity aptamers (as described previously) added (50 µl/well, 0.34 nM-20 µM, titrated in SCHMK buffer). As a positive control an anti-TNFR1 monoclonal antibody (R&D Systems) was included. Following a 2 h incubation (room temperature on a shaking platform) a complex of biotin-TNFα (1 ng/ml, NEN) and streptavidin alkaline phosphatase conjugate (1:1000, Amersham) in 2% BSA/SCHMK buffer (50 µl/well) was added. Following a 2 h incubation (room temperature on a shaking platform) the plates were washed (×6) and developed using ELISA Amplification System (Life Technologies) according to the manufacturer's instructions and the OD measured at 490 nm. On each plate the total binding was determined by TNFR1 and biotin-TNFα/conjugate in the presence of BSA/SCHMK buffer, and non-specific binding of biotin-TNFα in the absence of the receptor or binding of the conjugate to the receptor in the absence of biotin-TNFα. In this experiment neither the specific aptamer ADR 58, nor the pool of non specific aptamers as described previously were able to inhibit the binding of TNFα to the TNFR1 receptor (FIGS. 19C1 and C2).

The ability of aptamer ADR 58 to prevent IL-6 mediated activation of the STAT-sPAP reporter gene in HepG2 cells was examined using the protocol described in Example 7b. While the aptamer was capable of inhibiting OSM activation of the reporter gene, neither ADR 58 or the control aptamer ADR147, showed any inhibition of IL-6 mediated activation of the reporter gene (FIG. 22).

Aptamer ADR 58 represents a highly potent and selective functional antagonist of human OSM which may therefore be used as a therapeutic molecule in the treatment of OSM related disorders.

The invention claimed is:

1. A method of reducing cartilage degradation in a patient comprising administering to a patient in need thereof an effective amount of an anti-OSM antagonist antibody to the mature form of SEQ ID NO:12, wherein said antibody reduces the TNFα secretion from macrophages in said patient and interacts with at least one of the residues selected from the group consisting of: G120, Q16, Q20, N123 and N124 of the mature form of SEQ ID NO:12.

2. The method of claim 1 wherein said patient suffers from an inflammatory disorder selected from the group consisting of: rheumatoid arthritis, psoriatic arthritis, juvenile arthritis, inflammatory osteoarthritis, reactive arthritis, Crohns disease, ulcerative colitis, gastritis, asthma, chronic obstructive pulmonary disease, Alzheimer's disease, multiple sclerosis and psoriasis.

3. The method according to claim 1, wherein the anti-OSM antagonist antibody is an antibody of the receptor gp130 (type II) of human oncostatin M as set forth in the mature form of SEQ ID NO:12.

4. The method according to claim 1 wherein the antibody is humanized or chimerized.

5. The method according to claim 1, wherein the anti-OSM antagonist antibody further prevents or reduces collagen release from cartilage.

6. The method according to claim 2 wherein said disorder is rheumatoid arthritis.

7. The method of claim 1 wherein the antibody is administered alone.

8. The method of claim 1 wherein the antibody is administered in combination with an immunosuppressive agent.

9. The method of claim 1 wherein the antibody is administered subcutaneously.

* * * * *